US009512448B2

(12) United States Patent
Van Zyl et al.

(10) Patent No.: US 9,512,448 B2
(45) Date of Patent: Dec. 6, 2016

(54) METHOD FOR ENHANCING CELLOBIOSE UTILIZATION

(75) Inventors: Willem Van Zyl, Stellenbosch (ZA); Ronel Van Rooyen, Lichtenburg (ZA); Shaunita Hellouise Rose, Strand (ZA)

(73) Assignee: Stellenbosch University, Stellenbosch (ZA)

(*) Notice: Subject to any disclaimer, the term of this patent is extended or adjusted under 35 U.S.C. 154(b) by 543 days.

(21) Appl. No.: 12/599,425

(22) PCT Filed: May 9, 2008

(86) PCT No.: PCT/IB2008/002398
§ 371 (c)(1),
(2), (4) Date: Oct. 25, 2010

(87) PCT Pub. No.: WO2008/155665
PCT Pub. Date: Dec. 24, 2008

(65) Prior Publication Data
US 2011/0177542 A1 Jul. 21, 2011

(30) Foreign Application Priority Data
May 9, 2007 (ZA) .................................. 2007/03747

(51) Int. Cl.
 *C12P 7/10* (2006.01)
 *C12N 1/36* (2006.01)
 *C12N 9/42* (2006.01)

(52) U.S. Cl.
 CPC . *C12P 7/10* (2013.01); *C12N 1/36* (2013.01); *C12N 9/2445* (2013.01); *C12Y 302/01021* (2013.01); *Y02E 50/16* (2013.01); *Y02P 20/52* (2015.11)

(58) Field of Classification Search
None
See application file for complete search history.

(56) References Cited

PUBLICATIONS

Riaan Den Haan et al. Hydrolysis and fermentation of amorphous cellulose by recombinant *Saccharomyces cerevisiae*. 2007. 9: 87-94. Available online Sep. 16, 2006.*
Chang, Y et al. RecName: Full=Lactose permease. 1990. GenBank P07921.1. p. 1-2.*
Machida, M. et al. RecName: Full=Beta-glucosidase. 2006. GenBank P22506. p. 1-3.*
Sreekrishna K. et al. Construction of strains of *Saccharomyces cerevisiae* that grow on lactose. 1985. PNAS. 82:7909-7913.*
van Rooyen, R. Genetic engineering of the yeast *Saccharomyces cerevisiae* to ferment cellobiose. Mar. 2007. Dissertation at the University of Stellenbosch. p. 1-194.*
Bolotin-Fukuhara M et al. Genomic Exploration of the Hemiascomycetous Yeasts: 11. Kluyveromyces lactis. 2000. FEBS Letters. 487. p. 66-70.*
Bauer, F.F. and Pretorius, I.S., "Pseudohyphal and Invasive Growth in *Saccharomyces Cerevisiae*: Signal Transduction During Nutrient Limitation," *Focus on Biotechnoly-Applied Microbiology*, 2:109-133, Kluwer Academic Publishers, Netherlands (2001).
Bowie, J.U., et al., "Deciphering the Message in Protein Sequences: Tolerance to Amino Acid Substitutions," *Science*, 247:1306-1310, Science, United States (1990).
Brutlag, D.L., et al., "Improved Sensitivity of Biological Sequence Database Searches," *Comp. App. Biosci.*, 6:237-245, Oxford University Press, UK (1990).
Cox, P.M., et al., "Acceleration of Global Warming due to Carbon-cycle Feedbacks in a Coupled Climate Model," *Nature*, 408:184-187, Macmillan Magazines Ltd., United States (2000).
Cuningham, B.C. and Wells, J.A., "High-Resolution Epitope Mapping of hGH-Receptor Interactions by Alanine-Scanning Mutagenesis," *Science*, 244:1081-1085, American Association for the Advancement of Science, United States (1989).
Dan, S., et al., "Cloning, Expression, Characterization, and Nucleophile Identification of Family 3, *Aspergillus niger* β-Glucosidase," *J. Biol. Chem.*, 275:4973-4980, American Society for Biochemistry and Molecular Biology, United States (2000).
Freer, S.N., et al., "Transport of Glucose and Cellobiose by *Candida wickerhamii* and *Clavispora lusitaniae*," *The Journal of Biological Chemistry*, 265:12864-12868, American Society for Biochemistry and Molecular Biology, United States (1990).
Furuta, H., et al., "Production of Glucoamylase by Passively Immobilized Cells of a Flocculent Yeast, *Saccharomyces diastaticus*," *Journal of Fermentation and Bioengineering*, 84:169-171, Elsevier B.V., Holland (1997).
Gagiano, M., et al., "The Sensing of Nutritional Status and the Relationship to Filamentous Growth in *Saccharomyces cerevisiae*," *FEMS Yeast Research*, 2:433-470, Elsevier, Holland (2002).
Gödecke, A., et al., "Coregulation of the *Kluyveromyces lactis* Lactose Rermease and β-Galactoidase Genes is Achieved by Interaction of Multiple LAC9 Binding Sites in a 2.6 kbp Divergent Promoter," *Nucleic Acids Research*, 19:5351-5358, Oxford University Press, UK (1991).
Görgens, J.F., et al., "The Metabolic Burden of the PGK1 and ADH2 Promoter Systems for Heterologous Xylanase Production by *Saccharomyces cerevisiae* in Defined Medium," *Biotechnol. Bioeng.*, 73:238-245, John Wiley & Sons, Inc., United States (2001).
Halme, A., et al., "Genetic and Epigenetic Regulation of the FLO Gene Family Generates Cell-Surface Variation in Yeast," *Cell*, 116:405-415, Cell Press, United States (2004).
Higgins, D.G. and Sharp, P.M., "Fast and sensitive multiple sequence alignments on a microcomputer," *CABIOS*, 5:151-153, Oxford University Press, UK (1989).

(Continued)

*Primary Examiner* — Paul Holland
(74) *Attorney, Agent, or Firm* — Nutter McClennen & Fish LLP

(57) ABSTRACT

The present invention relates to methods for improving a host cell's ability to utilize the disaccharide cellobiose. In some embodiments, a transformed cell expresses intracellular β-glucosidase. In other embodiments, a transformed host cell is able to grow on media wherein cellobiose is the sole carbon source. In other embodiments, selection methods are provided which improve a host cell's ability to grow on cellobiose-containing media.

7 Claims, 10 Drawing Sheets

(56) References Cited

PUBLICATIONS

Iwashita, K.T. and Nagahara, T., et al., "The bglA Gene of *Aspergillus kawachii* Encodes Both Extracellular and Cell Wall-Bound β-Glucosidases," *Appl. Envir. Microbiol.*, 65:5546-5553, American Society for Microbiology, United States (1999).

Kaplan, J.G., "An Inducible System for the Hydrolysis and Transport of Beta-Glucosides in Yeast. I. Characteristics of the Beta-Glucosidase Activity of Intact and of Lysed Cells," *The Journal of General Physiology*, 48:873-886, The Rockefeller University Press, United States (1965).

Kern, L., et al., "The FUR1 Gene of *Saccharomyces cerevisiae*: Cloning, Structure and Expression of Wild-type and Mutant Alleles," *Gene*, 88:149-157, Elsevier, Holland (1990).

Kohchi, C. and Toh-E, A.,"Cloning of *Candida pelliculosa* β-*glucosidase* Gene and its Expression in *Saccharomyces cerevisiae*," *Mol. Gen. Genet.*, 203:89-94, Springer-Verlag, Berlin/Heidelberg (1986).

Kondo, A., et al., "High-level Ethanol Production from Starch by a Flocculent *Saccharomyces cerevisiae* Strain Displaying Cell-surface Glucoamylase," *Applied Microbiology and Biotechnology*, 58:291-296, Springer-Verlag, Berlin/Heidelberg (2002).

Liu, Y., et al., "Bioconversion Using Immobilized Recombinant Flocculent Yeast Cells Carrying a Fused Enzyme Gene in an 'Intelligent' Bioreactor," *Biochem. Eng. J.*, 2:229-235, Elsevier, Holland (1998).

Lynd, L.R., et al., "Microbial Cellulose Utilization: Fundamentals and Biotechnology," *Microbiol. Mol. Biol. Rev.*, 66:506-577, American Society for Microbiology, United States (2002).

Machida, M., et al., "Nucleotide Sequences of *Saccharomycopsis fibuligera* Genes for Extracellular Beta Glucosidases as Expressed in *Saccharomyces cerevisiae*," *Applied and Environmental Microbiology*, 54:3147-3155, American Society for Microbiology, United States (1988).

Mansfield, S.D. and Meder, R., "Cellulose Hydrolysis—the Role of Monocomponent Cellulases in Crystalline Cellulose Degradation," *Cellulose*, 10: 159-169, Kluwer Academic Publishers, Netherlands (2003).

Meinander, N., et al., "A Heterologous Reductase Affects the Redox Balance of Recombinant *Saccharomyces cerevisiae*," *Microbiology*, 142: 165-172, Society for General Microbiology, UK (1996).

Nakamura, Y., et al., "Codon Usage Tabulated from International DNA Sequence Databases: Status for the Year 2000," *Nucl. Acids Res.*, 28:292, Oxford University Press, UK (2000).

Nolan, T., et al., "Quantification of mRNA using real-time RT-PCR," *Nature Protocols*, 1:1559-1582, Nature Publishing Group, UK (2006).

Pan, X., et al., "Signal Transduction Cascades Regulating Pseudohyphal Differentiation of *Saccharomyces cerevisiae*," *Current Opinion in Microbiology*, 3:567-572, Elsevier Science Ltd., Holland (2000).

Raynal, A. and Guerineau, M., "Cloning and Expression of the Structural Gene for β-Glucosidase of *Kluyveromyces fragilis* in *Escherichia coli* and *Saccharomyces cerevisiae*," *Mol. Gen. Genet.*, 195:108-115, Springer Berlin/Heidelberg (1984).

Romanos, M.S., et al., "Foreign Gene Expression in Yeast: a Review," *Yeast*, 8:423-488, John Wiley & Sons, Ltd., United States (1992).

Shen, Y., et al., "Simultaneous Saccharification and Fermentation of Acid-Pretreated Corncobs with a Recombinant *Saccharomyces cerevisiae* Expressing β-Glucosidase," *Bioresource Technology*, 99:5099-5103, Elsevier, Holland (2008).

Van Rooyen, R., et al., "Construction of Cellobiose-Growing and Fermenting *Saccharomyces cerevisiae* Strains," *J. Biotechnol.*, 120:284-295, Elsevier, Holland (2005).

Yan, T., et al., "Purification and Characterization of an Extracellular β-Glucosidase II with High Hydrolysis and Transglucosylation Activities from *Aspergillus niger*," *J. Agric. Food. Chem.*, 46:431-437, American Chemical Society, United States (1998).

International Search Report for International Application No. PCT/IB08/02398, European Patent Office, Netherlands, mailed on Jun. 2, 2009.

\* cited by examiner

METHOD FOR ENHANCING CELLOBIOSE UTILIZATION

REFERENCE TO SEQUENCE LISTING SUBMITTED ELECTRONICALLY

The content of the electronically submitted substitute sequence listing, under file name: SequenceListingascii.TXT; Size: 17,299 bytes; and Date of Creation: Oct. 19, 2010, filed herewith, is incorporated by reference in its entirety.

BACKGROUND OF THE INVENTION

Field of the Invention

The present relates to a method for enhancing cellobiose utilization ability of yeast, and in particular, for enhancing intracellular cellobiose utilization of *Saccharomyces cerevisiae*.

Background Art

The potential of plant biomass as a cheap and renewable substrate for the production of fuel and chemicals has gained considerable interest in recent years. The biological saccharification of cellulose, the main component of plant biomass, is of particular interest in the field of fuel ethanol production. Four, biologically mediated process steps are involved in the current cellulose-to-ethanol technology: (i) cellulase enzyme production; (ii) enzymatic saccharification of cellulose; (iii) fermentation of hexose sugars (end-products of cellulose hydrolysis); and (iv) fermentation of pentose sugars (end-products of hemicellulose hydrolysis) to ethanol (Lynd, L. R., et al., *Microbiol. Mol. Biol. Rev.* 66:506-577 (2002)). Combining all four process steps into a one-step conversion of cellulose to fuel ethanol (called consolidated bioprocessing (CBP)) would result in a considerable reduction in processing costs (Lynd, L. R., et al., *Microbiol. Mol. Biol. Rev.* 66:506-577 (2002)).

*Saccharomyces cerevisiae* has superior ethanol formation properties, but is non-cellulolytic. The expression of cellulases in *S. cerevisiae* would be a prerequisite for cellulose conversion via CBP. *S. cerevisiae* has received a great deal of interest regarding heterologous protein expression as well as the production of ethanol and other commodity product (Lynd, L. R., et al., *Microbiol. Mol. Biol. Rev.* 66:506-577 (2002)); (Romanos, M. S, et al., *Yeast* 8:423-88 (1992)). Expression of a functional cellulase system in *S. cerevisiae* would require the co-expression of at least three groups of enzymes, namely endoglucanases (EC 3.2.1.4); exoglucanases (EC 3.2.1.91) and β-glucosidases (EC 3.2.1.21). These enzymes act synergistically to efficiently degrade cellulose (Mansfield and Meder; 2003). β-Glucosidases catalyze the hydrolysis of soluble cellodextrins and cellobiose to glucose. β-glucosidases from various origins, e.g. *Aspergillus niger* (Dan, S., et al. *J Biol Chem* 275:4973-4980 (2000)), *Aspergillus kawachii* (Van Rooyen, R., et al., *J. Biotechnol.* 120:284-295 (2005); Iwashita, K. T. Nagahara, et al., *Appl Environ Microbiol* 65:5546-5553 (1999)) *Candida pelliculosa* var. *acetaetherius* (Kohchi C. and A. Toh-e, *Mol Gen Genet* 203:89-94 (1986)), *Candida wickerhamii* (Van Rooyen, R., et al., *J Biotechnol.* 120:284-295 (2005)), *Saccharomycopsis fibuligera* and *Trichoderma reesei* (Van Rooyen, R., et al., *J. Biotechnol.* 120:284-295 (2005)) have been successfully expressed in *S. cerevisiae*. This previous work focused on secreted β-glucosidases. Raynal A. and M. Guérineau, et al., *Mol Gen Genet* 195:108-115 (1984) have genetically engineered *S. cerevisiae* to produce the *Kluyveromyces lactis* β-glucosidase intracellularly, but the recombinant strain was unable to grow on cellobiose.

Previous work of the applicant describes the construction of cellobiose-fermenting strains of *S. cerevisiae* by introduction of secreted β-glucosidases from various fungal origins (Van Rooyen, R., et al., *J. Biotechnol.* 120:284-295 (2005)). The accumulation of extracellular cellobiose has two major disadvantages: (i) it causes feedback inhibition of endoglucanases and cellobiohydrolases and therefore limits the rate and extent of cellulose hydrolysis (Yan, T., et al., *J. Agric. Food. Chem.* 46:431-437 (1998)); and (ii) the action of β-glucosidases releases glucose in the external environment that increases the risk of contamination.

There is therefore a need for a method for enhancing intracellular cellobiose utilization by a host cell such as *S. cerevisiae*, which does not have the problems described above.

BRIEF SUMMARY OF THE INVENTION

According to one embodiment of the invention, there is provided a method of modifying a yeast so as to increase intracellular cellobiose utilisation by the yeast, the method including the steps of transforming the yeast with a DNA sequence encoding mature β-glucosidase and causing the yeast to express the mature β-glucosidase wherein the β-glucosidase is maintained in the cell.

According to some embodiments of the invention, a host cell transformed as above is provided. In some embodiments, the host cell is a yeast.

According to another embodiment of the invention, there is provided a method of modifying a yeast so as to increase intracellular cellobiose utilisation by the yeast, the method including the steps of transforming the yeast with a DNA sequence encoding mature *Saccaromycospis fibuligera* β-glucosidase (BGL1) and causing the yeast to express the mature *Saccaromycospis fibuligera* β-glucosidase (BGL1).

The yeast may be selected, for example, from the genera *Saccharomyces*, *Kluyveromyces*, *Candida*, *Pichia*, *Schizosaccharomyces*, *Hansenula*, *Kloeckera*, *Schwanniomyces*, and *Yarrowia*. Yeast species as host cells include, for example, *S. cerevisiae*, *S. bulderi*, *S. barnetti*, *S. exiguus*, *S. uvarum*, *S. diastaticus*, *K. lactis*, *K. marxianus* and *K. fragilis*.

Native disaccharide (α-glucoside) transporter(s) of the yeast may be adapted, and/or heterologous disaccharide (α-glucoside) transporter(s) may be introduced into the yeast.

In some embodiments, other cellulase genes of fungal origin may be co-expressed with *S. fibuligera* β-glucosidase.

In other embodiments, other cellulase genes of fungal origin may be co-expressed with the polypeptide having β-glucosidase activity (E.C. 3.2.1.21).

According to another embodiment of the invention, there is provided an expression cassette containing a constitutive promoter and a DNA sequence encoding mature *S. fibuligera* β-glucosidase (BGL1).

The promoter may be, for example, a *S. cerevisiae* phosphoglycerate kinase 1 (PGK1) gene promoter or any other suitable promoter which can drive gene expression in the host cell of the invention.

According to a further embodiment of the invention there is provided a vector including the expression cassette.

The vector may be transformed into a yeast, such as *S. cerevisiae* SIGMA, and maintained episomally. The vector may be a plasmid, and in particular, a multicopy, episomal plasmid such as ySSFI. The vector may also be a CEN plasmid.

According to another embodiment of the invention, there is provided a yeast strain transformed with the expression vector described above.

The yeast strain may be, for example, *S. cerevisiae* SIGMA into which the expression vector has been chromosomally integrated.

The transformed yeast strain may have an increased capacity for transporting extracellular cellobiose into the intracellular space of the yeast compared to an untransformed yeast cell. Further, the transformed yeast cell may be able to hydrolyse more cellobiose than an untransformed yeast cell.

Cellobiose transport by the transformed yeast may involve adaptation of its native disaccharide (α-glucoside) transporter(s). More specifically, the AGT1 (also known as MAL21) transporter or maltose permeases (for example MAL21, MAL31, MAL41, MAL51, and MAL61) may serendipitously transport cellobiose, and elevated levels of these transporters in the presence of maltose may enhance cellobiose transport.

Cellobiose transport by the transformed host cell, such as *S. cerevisiae*, may be further enhanced by introducing heterologous disaccharide (α-glucoside) transporter(s). Examples of such transporters are di- and tri-saccharide transporters, including maltose, maltotriose and lactose transporters from other microbial hosts.

In other embodiments, lactose permease, such as from *K. lactis*, can be co-expressed with the polypeptide containing the β-glucosidase activity, and the permease can facilitate cellobiose transport into the host cell of the invention.

Further improvement of cellobiose transport, using either over-expressed natively or heterologously expressed transporters, may be facilitated in selection studies for enhanced growth (elevated growth rate) of recombinant yeasts producing β-glucosidase intracellularly on cellobiose as sole carbon source.

The transformed yeast strain may also display phenotypic characteristics such as flocculation, pseudohyphal growth and biofilm-formation.

The transformed yeast strain may also be able to adhere to cellulose.

According to a further embodiment of the invention, there is provided a method of up-regulating the α-glucoside transporter of a yeast, such as *S. cerevisiae*, the method including the step of transforming the yeast with a DNA sequence encoding mature *S. fibuligera* β-glucosidase (BGL1).

In other embodiments of the invention, methods of culturing a host cell transformed with a polynucleotide encoding a polypeptide with β-glucosidase activity is provided. In some embodiments, these methods comprise contacting the host cell with a cellobiose-containing substrate under suitable conditions to allow fermentation of the cellobiose.

In other embodiments of the invention, methods for selecting for increased utilization of cellobiose by a transformed host cell according to the invention are provided.

BRIEF DESCRIPTION OF THE DRAWINGS

FIG. 1 depicts a 2583-kb DNA fragment (SEQ ID NO: 1), containing the open reading frame that encodes for the mature *Saccharomycospis fibuligera* BGL1 enzyme protein sequence (SEQ ID NO: 2). The EcoRI and XhoI sites were used to introduce the DNA fragment into plasmid yAZ4 to yield plasmid ySSF (FIG. 2).

DETAILED DESCRIPTION OF THE INVENTION

Cellulose is the most abundant biopolymer and is found almost exclusively in plant cell walls. Plants synthesize about 30×10$^9$ tons of cellulose annually (Cox, P. M., et al., *Nature* 408:184-187 (2001)). From a biotechnological point of view, it is an attractive source for the production of fermentable sugars. However, low cost technology for overcoming the recalcitrance of cellulosic biomass has not yet been established. A promising approach to conquer this barrier involves the production of cellulolytic enzymes, hydrolysis of biomass, and fermentation of resulting sugars in a single step process via a cellulolytic microorganism (Lynd, L. R., et al., *Microbiol. Mol. Biol. Rev.* 66:506-577 (2002)).

Figure 4A:
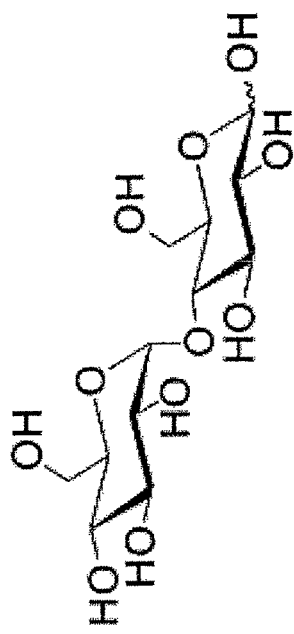
FIG. 4 depicts the stereochemistry of the disaccharides, cellobiose (A) and maltose (B).

The disaccharide cellobiose (FIG. 4a) is the end product of the breakdown of cellulose by cellulolytic enzymes such as endoglucanases, cellobiohydrolases, and exoglucanases. Despite the utility of certain yeast for efficient ethanol production on glucose substrates, these yeast are not readily able to utilize cellobiose in an industrially applicable setting to conduct fermentation.

It is widely recognized that *S. cerevisiae* does not produce a dedicated cellobiose permease/transporter. Therefore one strategy would be to produce a secretable β-glucosidase that catalyzes the hydrolysis of cellobiose to glucose extracellularly. However, extracellular cellobiose hydrolysis has disadvantages, such as feedback inhibition on cellulase activity, diffusion of the enzyme away from the cell, and high risk of microbial contamination upon hydrolysis to glucose. Engineering yeasts for efficient cellobiose utilization would be a significant step towards the development of a recombinant host that will be able to hydrolyse cellulose.

The applicants have now found that host cells, such as *S. cerevisiae*, when transformed with a DNA sequence encoding mature β-glucosidase so that it can produce functional β-glucosidase intracellularly, is better able to utilise cellobiose intracellularly. Other cellulase genes of fungal origin may be co-expressed with the β-glucosidase, such as cellulase (endoglucanase, cellobiohydrolase, and/or exoglucanase) activities. These transformed yeast strains represent a step towards the efficient degradation and utilisation of cellulosic materials by recombinant host cells, such as *S. cerevisiae*, producing a consortium of cellulolytic enzymes.

DEFINITIONS

A "vector," e.g., a "plasmid" or "YAC" (yeast artificial chromosome) refers to an extrachromosomal element often carrying one or more genes that are not part of the central metabolism of the cell, and is usually in the form of a circular double-stranded DNA molecule. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Preferably, the plasmids or vectors of the present invention are stable and self-replicating.

An "expression vector" is a vector that is capable of directing the expression of genes to which it is operably associated.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs.

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to at least about 75% identical to the amino acid sequences reported herein, at least about 80%, at least about 85%, or at least about 90% identical to the amino acid sequences reported herein, or at least about 95%, at least about 96%, at least about 97%, at least about 98%, at least about 99%, or 100% identical to the amino acid sequences reported herein. Suitable nucleic acid fragments are at least about 70%, at least about 75%, or at least about 80% identical to the nucleic acid sequences reported herein, at least about 80%, at least about 85%, or at least about 90% identical to the nucleic acid sequences reported herein, or at least about 95%, at least about 96%, at least about 97%, at least 98%, at least about 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

The term "probe" refers to a single-stranded nucleic acid molecule that can base pair with a complementary single stranded target nucleic acid to form a double-stranded molecule.

The term "complementary" is used to describe the relationship between nucleotide bases that are capable to hybridizing to one another. For example, with respect to DNA, adenine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

As used herein, the term "oligonucleotide" refers to a nucleic acid, generally of about 18 nucleotides, that is hybridizable to a genomic DNA molecule, a cDNA molecule, or an mRNA molecule. Oligonucleotides can be labeled, e.g., with 32P-nucleotides or nucleotides to which a label, such as biotin, has been covalently conjugated. An oligonucleotide can be used as a probe to detect the presence of a nucleic acid according to the invention. Similarly, oligonucleotides (one or both of which may be labeled) can be used as PCR primers, either for cloning full length or a fragment of a nucleic acid of the invention, or to detect the presence of nucleic acids according to the invention. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression may also refer to translation of mRNA into a polypeptide.

The functional expression of S. fibuligera β-glucosidase (BGL1) in the intracellular space of yeast is described herein. Additionally, any suitable enzyme with β-glucosidase activity (EC 3.2.1.21) can be used in the host cells of the present invention. Suitable enzymes with β-glucosidase activity (EC 3.2.1.21) include the enzymes listed in Table 1.

"Substantially retained in the cytoplasm" or "Substantially retained in the cell" as used herein refers to expression by a host cell of a polypeptide having a particular enzymatic activity, which is not moved into the extracellular space, for example, by secretion. Therefore, this enzymatic activity is not functionally detected in the extra-cellular space, for instance in the culture media in which the cells are grown. Rather, the enzyme activity is maintained internally in the cell. Assays for detecting enzymatic activities are known in the art. In some embodiments, the assay for enzymatic activity may comprise measuring β-glucosidase activity. In some embodiments, β-glucosidase activity is measured by incubating appropriately diluted cells or cell extracts with 5 mM of p-nitrophenyl-β-D-glucopyranoside (pNPG) in 50 mM citrate buffer at optimal pH and temperature for the specific enzyme according to the method previously described (Van Rooyen, R., et al., J. Biotechnol. 120:284-295 (2005)).

"Mature" as used herein in reference to a polypeptide, amino acid sequence or protein, refers to the completely processed and expressed form of the polypeptide, amino acid sequence or protein. Mature proteins lack a functional leader sequence, such as a secretion signal. In some embodiments, the mature proteins of the invention completely lack a leader sequence. In some embodiments of the invention, the mature protein is encoded by genes disclosed in Table 1. These polynucleotides may be modified according to the invention to lack a secretion signal, retain β-glucosidase activity, and therefore have the protein which they encode be expressed substantially only in the cytoplasm of the cell. In some embodiments of the invention the mature protein is S. fibuligera β-glucosidase (BGL1) which lacks a secretion signal.

Lack of a functional secretion signal prevents co-translational import into the secretory pathway and thus allows the nascent polypeptide to be released in the cytoplasm of the cell. The secretory signal hypothesis has been well characterized in a large range of cell types and although secretion signals vary in sequence, each has eight or more non-polar amino acids at its center (Alberts et al. Molecular Biology of the Cell. 2002. p. 667 and 694).

The "catalytic domain" is also referred to as the "active site." The structure and chemical properties of the active site allow the recognition and binding of the substrate. The active site is usually a small pocket at the surface of the enzyme that contains residues responsible for the substrate specificity (charge, hydrophobicity, steric hindrance) and catalytic residues which often act as proton donors or acceptors or are responsible for binding a cofactor such as PLP, TPP or NAD. The active site is also the site of inhibition of enzymes. In the case of β-glucosidase, the catalytic domain contains residues that allow the recognition, binding, and chemical action of the polypeptide on the cellobiose substrate.

Suitable enzymes with β-glucosidase activity (EC 3.2.1.21) can be found encoded by the genomes of the organisms listed in Table 1.

"β-glucosidase activity" or "(EC 3.2.1.21) activity" (using the IUBMB Enzyme Nomenclature) as defined herein includes the hydrolysis of terminal, non-reducing β-D-glucose residues with release of β-D-glucose. Other names for this enzyme activity include: gentiobiase; cellobiase; emulsin; elaterase; aryl-β-glucosidase; β-D-glucosidase; β-glucoside glucohydrolase; arbutinase; amygdalinase; p-nitrophenyl β-glucosidase; primeverosidase; amygdalase; limarase; salicilinase; and β-1,6-glucosidase. Suitable substrates include cellobiose and other β-D-glucosides. Some enzymes with (EC 3.2.1.21) activity also hydrolyse one or more of the following: β-D-galactosides, α-L-arabinosides, β-D-xylosides, and β-D-fucosides.

In some embodiments, the β-glucosidase is a β-glucosidase I. In other embodiments, the β-glucosidase is a β-glucosidase II.

TABLE 1

| | | | | | |
|---|---|---|---|---|---|
| | Suitable β-glucosidases. | | | | |
| Systematic Name | Accession No./SEQ ID NO. | Gene Name | Enzyme Activity | Organism | Seq. Length (A.A.) |
| BGL1_ASPAC | P48825 (SEQ ID NO: 15) | | Beta-glucosidase 1 precursor (EC 3.2.1.21) | Aspergillus aculeatus | 860 |

TABLE 1-continued

Suitable β-glucosidases.

| Systematic Name | Accession No./SEQ ID NO. | Gene Name | Enzyme Activity | Organism | Seq. Length (A.A.) |
|---|---|---|---|---|---|
| BGL1_BACSU | P40740 (SEQ ID NO: 16) | bglH, BSU39260, N17D | Beta-glucosidase (EC 3.2.1.21) | *Bacillus subtilis* | 469 |
| BGL1_SACFI | P22506 (SEQ ID NO: 17) | BGL1 | Beta-glucosidase 1 precursor (EC 3.2.1.21) | *Saccharomycopsis fibuligera* (Yeast) | 876 |
| BGL2_BACSU | P42403 (SEQ ID NO: 18) | yckE, BSU03410 | Probable beta-glucosidase (EC 3.2.1.21) | *Bacillus subtilis* | 477 |
| BGL2_SACFI | P22507 (SEQ ID NO: 19) | BGL2 | Beta-glucosidase 2 precursor (EC 3.2.1.21) | *Saccharomycopsis fibuligera* (Yeast) | 880 |
| BGL3_ASPWE | P29090 (SEQ ID NO: 20) | | Beta-glucosidase A-3 (EC 3.2.1.21) | *Aspergillus wentii* | 63 |
| BGLA_BACCI | Q03506 (SEQ ID NO: 21) | bglA | Beta-glucosidase (EC 3.2.1.21) | *Bacillus circulans* | 450 |
| BGLA_CLOTH | P26208 (SEQ ID NO: 22) | bglA, Cthe_0212 | Beta-glucosidase A (EC 3.2.1.21) | *Clostridium thermocellum* (strain ATCC 27405/ DSM 1237) | 448 |
| BGLA_ENTAG | Q59437 (SEQ ID NO: 23) | bglA | Beta-glucosidase A (EC 3.2.1.21) | *Enterobacter agglomerans* (*Erwinia herbicola*) (*Pantoea agglomerans*) | 480 |
| BGLA_PAEPO | P22073 (SEQ ID NO: 24) | bglA | Beta-glucosidase A (EC 3.2.1.21) (BGA) | *Paenibacillus polymyxa* (*Bacillus polymyxa*) | 448 |
| BGLA_THEMA | Q08638 (SEQ ID NO: 25) | bglA | Beta-glucosidase A (EC 3.2.1.21) | *Thermotoga maritima* | 446 |
| BGLA_THENE | O33843 (SEQ ID NO: 26) | bglA, gghA | Beta-glucosidase A (EC 3.2.1.21) | *Thermotoga neapolitana* | 444 |
| BGLB_CLOTH | P14002 (SEQ ID NO: 27) | bglB, Cthe_1256 | Thermostable beta-glucosidase B (EC 3.2.1.21) | *Clostridium thermocellum* (strain ATCC 27405/ DSM 1237) | 755 |
| BGLB_MICBI | P38645 (SEQ ID NO: 28) | bglB | Thermostable beta-glucosidase B (EC 3.2.1.21) | *Microbispora bispora* | 473 |
| BGLB_PAEPO | P22505 (SEQ ID NO: 29) | bglB | Beta-glucosidase B (EC 3.2.1.21) | *Paenibacillus polymyxa* (*Bacillus polymyxa*) | 448 |
| BGLC_MAIZE | P49235 (SEQ ID NO: 30) | GLU1 | Beta-glucosidase, chloroplast precursor (EC 3.2.1.21) | *Zea mays* (Maize) | 566 |
| BGLS_AGRSA | P12614 (SEQ ID NO: 31) | abg | Beta-glucosidase (EC 3.2.1.21) | *Agrobacterium* sp. (strain ATCC 21400) | 459 |
| BGLS_AGRTU | P27034 (SEQ ID NO: 32) | cbg-1 | Beta-glucosidase (EC 3.2.1.21) | *Agrobacterium tumefaciens* | 818 |
| BGLS_BUTFI | P16084 (SEQ ID NO: 33) | bglA | Beta-glucosidase A (EC 3.2.1.21) | *Butyrivibrio fibrisolvens* | 830 |
| BGLS_CALSA | P10482 (SEQ ID NO: 34) | bglA | Beta-glucosidase A (EC 3.2.1.21) | *Caldocellum saccharolyticum* (*Caldicellulosiruptor saccharolyticus*) | 455 |
| BGLS_HANAN | P06835 (SEQ ID NO: 35) | | Beta-glucosidase precursor (EC 3.2.1.21) | *Hansenula anomala* (Yeast) (*Candida pelliculosa*) | 825 |
| BGLS_KLUMA | P07337 (SEQ ID NO: 36) | | Beta-glucosidase precursor (EC 3.2.1.21) | *Kluyveromyces marxianus* (Yeast) (*Candida kefyr*) | 845 |
| BGLS_RUMAL | P15885 (SEQ ID NO: 37) | | Beta-glucosidase (EC 3.2.1.21) | *Ruminococcus albus* | 947 |

TABLE 1-continued

Suitable β-glucosidases.

| Systematic Name | Accession No./SEQ ID NO. | Gene Name | Enzyme Activity | Organism | Seq. Length (A.A.) |
|---|---|---|---|---|---|
| BGLS_SCHCO | P29091 (SEQ ID NO: 38) | | Beta-glucosidase (EC 3.2.1.21) | *Schizophyllum commune* (Bracket fungus) | 192 |
| BGLS_TRIRP | P26204 (SEQ ID NO: 39) | | Non-cyanogenic beta-glucosidase precursor (EC 3.2.1.21) | *Trifolium repens* (Creeping white clover) | 493 |
| BGLT_TRIRP | P26205 (SEQ ID NO: 40) | L1 | Cyanogenic beta-glucosidase precursor (EC 3.2.1.21) | *Trifolium repens* (Creeping white clover) | 425 |
| BGLX_ECOLI | P33363 (SEQ ID NO: 41) | bglX, yohA, b2132, JW2120 | Periplasmic beta-glucosidase precursor (EC 3.2.1.21) | *Escherichia coli* (strain K12) | 765 |
| BGLX_ERWCH | Q46684 (SEQ ID NO: 42) | bgxA | Periplasmic beta-glucosidase/ beta-xylosidase precursor [Includes: (EC 3.2.1.21) and (EC 3.2.1.37)] | *Erwinia chrysanthemi* | 654 |
| BGLX_SALTY | Q56078 (SEQ ID NO: 43) | bglX, STM2166 | Periplasmic beta-glucosidase precursor (EC 3.2.1.21) | *Salmonella typhimurium* | 765 |
| GBA3_CAVPO | P97265 (SEQ ID NO: 44) | Gba3, Cbg | Cytosolic beta-glucosidase (EC 3.2.1.21) | *Cavia porcellus* (Guinea pig) | 469 |
| GBA3_HUMAN | Q9H227 (SEQ ID NO: 43) | GBA3, CBG, CBGL1 | Cytosolic beta-glucosidase (EC 3.2.1.21) | *Homo sapiens* (Human) | 469 |
| GBA3_PONPY | Q5RF65 (SEQ ID NO: 44) | GBA3, CBG | Cytosolic beta-glucosidase (EC 3.2.1.21) | *Pongo pygmaeus* (Bornean orangutan) | 469 |

Polypeptides which have β-glucosidase activity also include fragments of the mature polypeptide, provided the fragments retain the activity. The polypeptide fragment from about amino acid 278 to about 309 of SEQ ID NO: 2 comprises the active site of the enzyme. In some embodiments, polypeptides of the invention can be defined to include the β-glucosidase activity (EC 3.2.1.21) found in polypeptides with at least 70, at least 80, at least 90, at least 95, at least 96, at least 97, at least 98, at least 99, or 100% homology with the polypeptide comprising amino acid residues 278 to 309 of SEQ ID NO: 2.

Suitable host cells of the present invention include, for example, the genera *Saccharomyces, Kluyveromyces, Candida, Pichia, Schizosaccharomyces, Hansenula, Kloeckera, Schwanniomyces*, and *Yarrowia*, and yeast species as host cells can include, for example, *S. cerevisiae, S. bulderi, S. barnetti, S. exiguus, S. uvarum, S. diastaticus, K. lactis, K. marxianus*, and *K. fragilis*.

A constitutive promoter, such as a *S. cerevisiae* phosphoglycerate kinase 1 (PGK1) gene promoter, can be used to express the *S. fibuligera* (BGL1) enzyme. However, any suitable promoter able to drive gene expression can be used in embodiments of the present invention.

The native disaccharide (α-glucoside) transporter(s) of the yeast can be adapted, and/or heterologous disaccharide (α-glucoside) transporter(s) can be introduced into the yeast to facilitate better cellobiose transport. For example, the *S. cerevisiae* AGT1 transporter (also known as Mal11) or maltose permeases (for example Mal61) may serendipitously transport cellobiose, and elevated levels of these transporters in the presence of maltose may enhance cellobiose transport.

In some embodiments, the transformed host cell has an increased capacity for transporting extracellular cellobiose into the intracellular space of the host compared to an untransformed host cell. In some embodiments, the transformed host cell is further transformed with an exogenous permease which may facilitate uptake of cellobiose in the host cell. Examples of such useful transporters are di- and tri-saccharide transporters, including maltose, maltotriose and lactose transporters from other microbial hosts such as those listed in Table 2. In some embodiments, the host cell may be transformed with a lactose permease from *K. lactis* LAC12. Other permeases suitable for various embodiments of the present invention are disclosed in Table 2.

TABLE 2

Suitable permeases.

| Microbial species | Protein product | Accession No. |
|---|---|---|
| Fungal sources: | | |
| Debaromyces hansenii | "unnamed product" | CR382139 |
| Pichia stipitis | Lac1 (lactose permease) | NC_009042 |
| Ajellomyces capsulatus | lactose permease* | XP_001544233 (SEQ ID NO: 48)/ XM_001544183 (SEQ ID NO: 47) |
| Aspergillus oryzae | "unnamed product" | NW_001884661 |
| Aspergillus clavatus | MFS Lactose permease* | NW_001517095 |
|  | MFS Lactose permease* | NW_001517095 |
| Neosartorya fischeri | Putative MFS Lactose permease* | XP_001264024 (SEQ ID NO: 50)/ XM_001264023 (SEQ ID NO: 49) |
| Neurospora crassa | Putative MFS Lactose permease* | XP_963801 (SEQ ID NO: 52)/ XM_958708 (SEQ ID NO: 51) |
| Aspergillus terreus | MFS Sugar (and other) transporter | XP_001791292 (SEQ ID NO: 54)/ XM_001218513 (SEQ ID NO: 53) |
| Aspergillus nidulans | MFS Sugar (and other) transporter | XP_660803 (SEQ ID NO: 56)/ XM_655711 (SEQ ID NO: 55) |
| Phaeosphaeria nodorum | MFS Sugar (and other) transporter | XP_001218514 (SEQ ID NO: 58)/ XM_001791240 (SEQ ID NO: 57) |
| Magnaporthe grisea | MFS Sugar (and other) transporter | XP_369159 (SEQ ID NO: 60)/ XM_369159 (SEQ ID NO: 59) |
| Chaetomium globosum | MFS Sugar (and other) transporter | XP_001220480 (SEQ ID NO: 62)/ XM_001220479 (SEQ ID NO: 61) |
| Gibberella zeae | MFS Sugar (and other) transporter | XP_383448 (SEQ ID NO: 64)/ XM_383448 (SEQ ID NO: 63) |
| Podospora anserina | MFS Sugar (and other) transporter | XP_001912722 (SEQ ID NO: 66)/ XM_001912687 (SEQ ID NO: 65) |
| Sclerotinia sclerotiorum | MFS Sugar (and other) transporter | XP_001595903 (SEQ ID NO: 68)/ XM_001595853 (SEQ ID NO: 67) |
| Cryptococcus neoformans | Sugar transporter | NC_009188 |
| Candida albicans | Glucose transporter | NW_139539. |
| Cryptococcus neoformans | Trehalose transporter | NC_006691 |
| Actinomycetes sources: | | |
| Thermobifida fusca | bglA (putative cellobiose permease) | AF086819 (SEQ ID NO: 69) |
| Thermobifida fusca | bglB | AF086819 (SEQ ID NO: 70) |
| Streptomyces avermitilis | cebF cellobiose ABC transporter permease | NP_826432 (SEQ ID NO: 71)/ NC_003155 |
| Streptomyces reticuli | cebF cellobiose ABC transporter permease | CAB46343 (SEQ ID NO: 72)/ AJ009797 (SEQ ID NO: 73) |
| Streptomyces coelicolor | cellobiose transport permease | NP_627027 (SEQ ID NO: 74)/ NC_003888 |
| Streptomyces griseus subsp. griseus | Putative cellobiose transport permease | BAG21566 (SEQ ID NO: 75)/ AP009493 |
| Saccharopolyspora erythraea | Putative cellobiose transport permease | YP_001107613 (SEQ ID NO: 76)/ NC_009142 |

*Does not have a specific name

Further improvement of cellobiose transport, using overexpressed native or heterologous transporters can be facilitated in selection for enhanced growth (increased growth rate) of recombinant yeasts producing β-glucosidase retained intracellularly grown on cellobiose as the sole carbon source. In some embodiments of the present invention, the mRNA of endogenous disaccharide transporters is expressed at least about 2 fold, at least about 4 fold, at least about 12 fold, at least about 50 fold, at least about 100 fold, at least about 1000 fold, or at least about 10,000 fold higher levels in selected cells of the invention relative to unselected cells. It is recognized in the art that higher mRNA levels often yield higher protein expression levels. mRNA levels can be measured by various known methods including quantitative Northern blotting, RNA Slot Blotting (Maniatis 4.9), and Reverse Transcriptase-PCR methods (Nolan T. et al., Nat. Protoc. 1: 1559-1582 (2006)).

The transformed yeast cell is also able to hydrolyse more cellobiose than an untransformed yeast cell, and may be able to adhere to cellulose. Phenotypic characteristics such as flocculation, pseudohyphal growth and biofilm-formation are also displayed.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the β-glucosidase polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of SEQ ID NO:1, the ORF (open reading frame) of the BGL1 DNA.

As a practical matter, whether any particular nucleic acid molecule or polypeptide is at least 80%, at least 85%, at least 90%, at least 95%, at least 96%, at least 97%, at least 98% or at least 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* (1990) 6:237-245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Of course, due to the degeneracy of the genetic code, one of ordinary skill in the art will immediately recognize that a large portion of the nucleic acid molecules having a sequence at least 90%, at least 95%, at least 96%, at least 97%, at least 98%, or at least 99% identical to the nucleic acid sequence of SEQ ID NO: 1 or fragments thereof, will encode polypeptides that have "β-glucosidase activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having β-glucosidase functional activity.

Thus, the invention further includes β-glucosidase polypeptide "variants" which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science* 244:1081-1085 (1989).) The resulting mutant molecules can then be tested for biological activity.

As Cunningham and Wells state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Derivatives of *S. fibuligera* BGL1 polypeptides of the present invention are polypeptides which have been altered so as to exhibit additional features not found on the native polypeptide. Derivatives can be covalently modified by substitution, chemical, enzymatic, or other appropriate means with a moiety other than a naturally occurring amino acid (for example, a detectable moiety such as an enzyme or radioisotope). Examples of derivatives include fusion proteins.

An analog is another form of a BGL1 polypeptide of the present invention. An "analog" also retains substantially the same biological function or activity as the polypeptide of interest, i.e., functions as a BGL1. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The present invention also relates to vectors which include polynucleotides of the present invention, host cells which are genetically engineered with vectors of the invention and the production of polypeptides of the invention by recombinant techniques.

Polynucleotides of SEQ ID NO:1 and SEQ ID NO: 11 and the translated amino acid sequences of SEQ ID NO:2 and SEQ ID NO:12 are sufficiently accurate and otherwise suitable for a variety of uses well known in the art and described herein. Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

The polynucleotide encoding for the mature polypeptides of the invention many include only the coding sequence for the mature polypeptide; the coding sequence of any domain of the mature polypeptide; and the coding sequence for the mature polypeptide (or domain-encoding sequence) together with non-coding sequence, such as introns or non-coding sequence 5' and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences.

The present invention further encompasses polypeptides which comprise, or alternatively consist of, an amino acid sequence which is at least 80%, 85%, 90%, 95%, 96%, 97%, 98%, 99% identical to, for example, the amino acid sequence shown in SEQ ID NO:2 and/or polypeptide fragments of any of these polypeptides (e.g., those fragments described herein, or domains of SEQ ID NO:2).

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The present invention also encompasses polypeptides which comprise, or alternatively consist of, an amino acid sequence which is at least 80%, 85%, 90%, 95%, 96%, 97%, 98%, 99% similar to the polypeptide of SEQ ID NO:2, and to portions of such polypeptide with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

Codon Optimization

As used herein the term "codon optimized coding region" means a nucleic acid coding region that has been adapted for expression in the cells of a given organism by replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 3. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 3

The Standard Genetic Code

| | T | C | A | G |
|---|---|---|---|---|
| T | TTT Phe(F) | TCT Ser(S) | TAT Tyr(Y) | TGT Cys(C) |
| | TTC Phe(F) | TCC Ser(S) | TAC Tyr(Y) | TGC |
| | TTA Leu(L) | TCA Ser(S) | TAA Ter | TGA Ter |
| | TTG Leu(L) | TCG Ser(S) | TAG Ter | TGG Trp(W) |
| C | CTT Leu(L) | CCT Pro(P) | CAT His(H) | CGT Arg(R) |
| | CTC Leu(L) | CCC Pro(P) | CAC His(H) | CGC Arg(R) |
| | CTA Leu(L) | CCA Pro(P) | CAA Gln(Q) | CGA Arg(R) |
| | CTG Leu(L) | CCG Pro(P) | CAG Gln(Q) | CGG Arg(R) |

TABLE 3-continued

The Standard Genetic Code

|   | T | C | A | G |
|---|---|---|---|---|
| A | ATT Ile(I) | ACT Thr(T) | AAT Asn(N) | AGT Ser(S) |
|   | ATC Ile(I) | ACC Thr(T) | AAC Asn(N) | AGC Ser(S) |
|   | ATA Ile(I) | ACA Thr(T) | AAA Lys(K) | AGA Arg(R) |
|   | ATG Met(M) | ACG Thr(T) | AAG Lys(K) | AGG Arg(R) |
| G | GTT Val(V) | GCT Ala(A) | GAT Asp(D) | GGT Gly(G) |
|   | GTC Val(V) | GCC Ala(A) | GAC Asp(D) | GGC Gly(G) |
|   | GTA Val(V) | GCA Ala(A) | GAA Glu(E) | GGA Gly(G) |
|   | GTG Val(V) | GCG Ala(A) | GAG Glu(E) | GGG Gly(G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database," and these tables can be adapted in a number of ways. See Nakamura, Y., et al. *Nucl. Acids Res.* 28:292 (2000). Codon usage tables for yeast, calculated from GenBank Release 128.0 [15 Feb. 2002], are reproduced below as Table 4. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 4

Codon Usage Table for *Saccharomyces cerevisiae* Genes

| Amino Acid | Codon | Number | Frequency per thousand |
|---|---|---|---|
| Phe | UUU | 170666 | 26.1 |
| Phe | UUC | 120510 | 18.4 |
| Total | | | |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Total | | | |
| Ile | AUU | 196893 | 30.1 |
| Ile | AUC | 112176 | 17.2 |
| Ile | AUA | 116254 | 17.8 |
| Total | | | |
| Met | AUG | 136805 | 20.9 |
| Total | | | |

TABLE 4-continued

Codon Usage Table for *Saccharomyces cerevisiae* Genes

| Amino Acid | Codon | Number | Frequency per thousand |
|---|---|---|---|
| Val | GUU | 144243 | 22.1 |
| Val | GUC | 76947 | 11.8 |
| Val | GUA | 76927 | 11.8 |
| Val | GUG | 70337 | 10.8 |
| Total | | | |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Total | | | |
| Pro | CCU | 88263 | 13.5 |
| Pro | CCC | 44309 | 6.8 |
| Pro | CCA | 119641 | 18.3 |
| Pro | CCG | 34597 | 5.3 |
| Total | | | |
| Thr | ACU | 132522 | 20.3 |
| Thr | ACC | 83207 | 12.7 |
| Thr | ACA | 116084 | 17.8 |
| Thr | ACG | 52045 | 8.0 |
| Total | | | |
| Ala | GCU | 138358 | 21.2 |
| Ala | GCC | 82357 | 12.6 |
| Ala | GCA | 105910 | 16.2 |
| Ala | GCG | 40358 | 6.2 |
| Total | | | |
| Tyr | UAU | 122728 | 18.8 |
| Tyr | UAC | 96596 | 14.8 |
| Total | | | |
| His | CAU | 89007 | 13.6 |
| His | CAC | 50785 | 7.8 |
| Total | | | |
| Gln | CAA | 178251 | 27.3 |
| Gln | CAG | 79121 | 12.1 |
| Total | | | |
| Asn | AAU | 233124 | 35.7 |
| Asn | AAC | 162199 | 24.8 |
| Total | | | |
| Lys | AAA | 273618 | 41.9 |
| Lys | AAG | 201361 | 30.8 |
| Total | | | |
| Asp | GAU | 245641 | 37.6 |
| Asp | GAC | 132048 | 20.2 |
| Total | | | |
| Glu | GAA | 297944 | 45.6 |
| Glu | GAG | 125717 | 19.2 |
| Total | | | |
| Cys | UGU | 52903 | 8.1 |
| Cys | UGC | 31095 | 4.8 |
| Total | | | |
| Trp | UGG | 67789 | 10.4 |
| Total | | | |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Total | | | |

TABLE 4-continued

Codon Usage Table for *Saccharomyces cerevisiae* Genes

| Amino Acid | Codon | Number | Frequency per thousand |
|---|---|---|---|
| Gly | GGU | 156109 | 23.9 |
| Gly | GGC | 63903 | 9.8 |
| Gly | GGA | 71216 | 10.9 |
| Gly | GGG | 39359 | 6.0 |
| Total | | | |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function of the Entelechon back translation tool. Constructing a rudimentary algorithm to assign codons based on a given frequency can also easily be accomplished with basic mathematical functions by one of ordinary skill in the art.

Codon-optimized coding regions can be designed by various methods known to those skilled in the art including software packages such as "synthetic gene designer" Wu, G., et al., *The Synthetic Gene Designer: A flexible web platform to explore sequence manipulation for heterologous expression. Protein Expr Purf.* 47(2):441-5 (2006)).

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, non-chromosomal and synthetic DNA sequences, e.g., derivatives of SV40; bacterial plasmids; and yeast plasmids. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. As representative examples of such promoters, there may be mentioned: ENO1, PGK1, TEF1, GPD1, ADH1 and the *E. coli*, lac or trp, and other promoters known to control expression of genes in prokaryotic or lower eukaryotic cells. The expression vector also contains a ribosome binding site for translation initiation and a transcription terminator. The vector may also include appropriate sequences for amplifying expression, or may include additional regulatory regions.

In addition, the expression vectors may contain one or more selectable marker genes to provide a phenotypic trait for selection of transformed host cells such as URA3, HIS3, LEU2, TRP1, LYS2 or ADE2, dihydrofolate reductase or neomycin resistance for eukaryotic cell culture, or tetracycline or ampicillin resistance in *E. coli*.

The vector containing the appropriate DNA sequence as herein, as well as an appropriate promoter or control sequence, may be employed to transform an appropriate host to permit the host to express the protein.

Thus, in certain aspects, the present invention relates to host cells containing the constructs described herein. The host cell can be a higher eukaryotic cell, such as a mammalian cell, or a lower eukaryotic cell, such as a yeast cell, e.g., *Saccharomyces cerevisiae*, or the host cell can be a prokaryotic cell, such as a bacterial cell.

Representative examples of appropriate hosts include: bacterial cells, such as *E. coli*, *Streptomyces*, *Salmonella typhimurium*; thermophilic or mesophlic bacteria; fungal cells, such as yeast; and plant cells, etc. In some embodiments, the host may be selected from the group consisting of *Saccharomyces*, *Kluyveromyces*, *Candida*, *Pichia*, *Schizosaccharomyces*, *Hansenula*, *Kloeckera*, *Schwanniomyces*, and *Yarrowia*. The selection of an appropriate host is deemed to be within the scope of those skilled in the art from the teachings herein.

In some embodiments, a method for selecting cells with improved ability to grow on cellobiose is disclosed. According to some embodiments, host cells transformed with a heterologous β-glucosidase may be cultured on cellobiose containing media and selected for ever increasing growth rate on the cellobiose containing media. In some embodiments, variant colonies displaying the fastest growth rate on the media may be selected. These "variant" colonies have undergone genetic or epigenetic changes which confer an increase in the cell's ability to grow on cellobiose relative to the average growth rate of the host cells on cellobiose. According to some embodiments, these variant colonies be selected and can be re-plated onto cellobiose containing media, allowed to grow up into colonies, and the fastest growing of these colonies can be selected and suspended in liquid and subsequently re-plated for further iterations of the method. In some embodiments, further iterations of the method can yield variants with many accumulated genetic or epigenetic changes which can contribute to the variant's ability to grow well on cellobiose-containing media.

In some embodiments of the invention, the fastest growing colonies will be easily visibly detectable by the ordinarily skilled artisan. The fastest growing colonies will have the largest diameter; therefore, these colonies will be the most useful for the next iteration of the method. In the selection process, the top 10, 5, 4, 3, 2, or 1% fastest growing of the colonies can be selected for propagation in the next iteration of the method. There may be at least 10 iterations of the method in some embodiments, but there may be as many as at least 20, at least 30, at least 50, at least 70, at least 100, or at least 1000 iterations in other embodiments. Iterations of the method will be useful until the strain produced by the method grows at least 10% faster than the original strain on cellobiose media. In other embodiments, iterations of the method can produce selected cells that are able to grow at least 20, at least 30, at least 50, at least 75, at least 100, at least 200, or at least 1000% faster than the original strain. Methods for determining the rate of growth will be apparent to the ordinarily skilled artisan and include, for example, measuring the optical density of cultures grown on the cellobiose-containing media as well as plating the cells on solid media containing cellobiose in order to observe the time required to view colonies upon incubation. The skilled artisan will be aware that the faster growing cells form visible colonies first and therefore larger colonies than other cells.

In some embodiments of the invention, methods for fermenting cellobiose are provided. In other embodiments, methods for fermenting cellobiose to ethanol are provided. In further embodiments, host cells of the invention are able to ferment cellobiose to ethanol.

In some embodiments, cells or cell cultures as described above are exposed to a lignocellulosic material. It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

The following embodiments of the invention will now be described in more detail by way of these non-limiting examples.

EXAMPLES

Example 1

Strains and Media

Table 5 summarises the genotypes and sources of the yeast and bacterial strains, as well as the plasmids that were constructed and used in the experiment.

Recombinant plasmids were constructed and amplified in *Escherichia coli* XL1-Blue cultivated at 37° C. in Luria-Bertani liquid medium or on Luria-Bertani agar (Sambrook, J., et al., *Molecular Cloning: A Laboratory Manual*, Cold Spring Harbor, N.Y. (1989)). Ampicillin for selecting and proliferating resistant bacteria was added to a final concentration of 100 µg·mL$^{-1}$.

*S. cerevisiae* SIGMA was cultivated in either YPD (1% yeast extract, 2% peptone, 2% glucose) or synthetic complete (SC) medium (0.67% yeast nitrogen base (Difco) containing amino acid supplements, 2% glucose). Recombinant *S. cerevisiae* was grown on YP medium (1% yeast extract, 2% peptone) containing either 10 g·L$^{-1}$ glucose, cellobiose or maltose as sole carbon source.

DNA Manipulations and Vector Construction

Standard protocols were followed for DNA manipulations (Sambrook, J., et al., *Molecular Cloning: A Laboratory Manual*, Cold Spring Harbor, N.Y. (1989)). The enzymes for DNA cleavage and ligation were purchased from Roche and used as recommended by the supplier. Restriction endonuclease-digested DNA was eluted from agarose gels by the method of Benson (1984).

PCR Amplification

PCR products were amplified from either plasmid DNA (15 ng) or *S. cerevisiae* genomic DNA (200 ng) with the aid of sequence specific primers (Table 6). The reaction mixture (50 µl) contained the following components: 10× reaction buffer, 500 µM of each of the nucleotide triphosphates, 0.25 µM of each primer, DNA template and 2.5 U EXPAND polymerase (Roche). DIG-labelled probes were synthesized with the aid of the "PCR DIG Probe Synthesis Kit" (Roche).

TABLE 5

Microbial strains and plasmids

| Strain or plasmid | Relevant genotype | Source of reference |
| --- | --- | --- |
| Strains | | |
| *S. cerevisiae* L5366h1 (SIGMA) | α leu2-3, 112 ura3-52 | Echard Boles, University of Duesseldorf, Germany |
| *E. coli* XL1 Blue | MRF' endA1 supE44 thi-1 recA1 gyrA96 relA1 lac (F' proAB lac$^q$ ZΔM15 Tn10 (tet)) | Strategene |
| Plasmids | | |
| pGEM-T-easy ® | bla | Promega |
| yAZ4 | bla URA3 PGK1$_{PT}$ | Van Rooyen, R., et al., *J Biotechnol.* 120: 284-295 (2005) |
| ySFI | bla URA3 PGK1$_P$-xyn2s-BGL1-PGK1$_T$ | Van Rooyen, R., et al., *J Biotechnol.* 120: 284-295 (2005) |
| ySSFI | bla URA3 PGK1$_P$-BGL1-PGK1$_T$ | This work |

TABLE 6

Summary of the PCR primers

| Primer name | Primer Sequence | Tm (product size) | Gene targeted |
|---|---|---|---|
| SSFI | L:<br>5'-<u>TCGCGA</u>ATTCATGGTCCCAATTC<br>AAAACTATACC-3'<br>(SEQ ID NO: 3)<br>R:<br>5'-CCG<u>CTCGAG</u>CGGTCAAATAGTAA<br>ACAGGACAGATG-3'<br>(SEQ ID NO: 4) | 64 (2583 bp)<br>65 | BGL1 |
| ACT | L:<br>5'-ACTGAAGCTCCAATGAACC-3'<br>(SEQ ID NO: 5)<br>R:<br>5'-CATCGACATCACACTTCATG-3'<br>(SEQ ID NO: 6) | 65 (549 bp)<br>65 | ACT1 |
| AGT | L:<br>5'-ATGATTGCTGTGGGACAA-3'<br>(SEQ ID NO: 7)<br>R:<br>5'-GTCTCGTTCTTCTTCCATTAA-3'<br>(SEQ ID NO: 8) | 64 (486 bp)<br>64 | AGT1<br>(α-Glucoside<br>transporters) |
| MAL | L:<br>5'-ATGATTGCTGTGGGACAA-3'<br>(SEQ ID NO: 9)<br>R:<br>5'-AGACAAGTAATTCTCGTTCTTCT-3'<br>(SEQ ID NO: 10) | 64 (499 bp)<br>65 | MAL61,<br>MAL11<br>(Maltose<br>transporters) |

Construction of Vector for Intracellular β-Glucosidase Production

Figure 2:
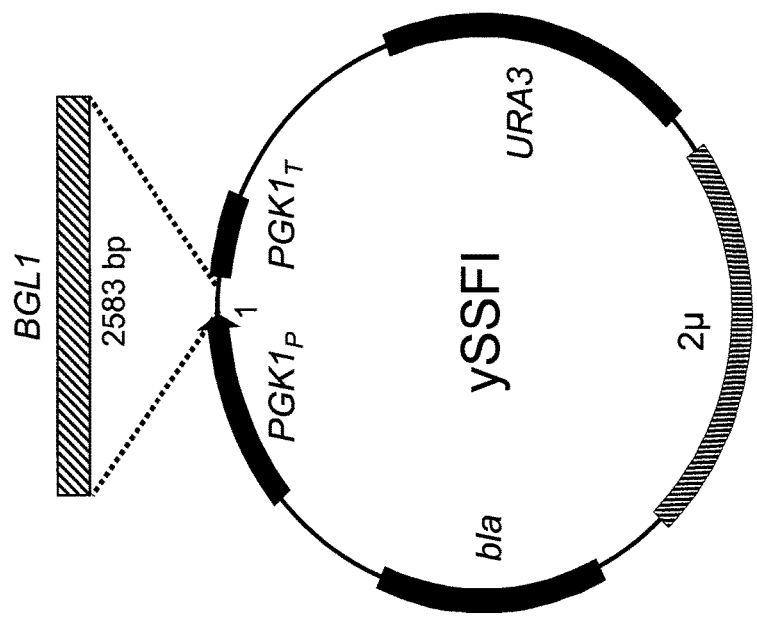
FIG. 2 is a schematic representation of plasmid ySSFI used in the invention. A *Saccharomycopsis fibuligera* BGL1 fragment encoding the mature BGL β-glucosidase was inserted between the PGK1$_P$, and PGK1$_T$, representing the *S. cerevisiae* phosphoglycerate kinase 1 gene promoter and terminator sequences. The *S. cerevisiae* 2-micron autonomous replicating sequence (ARS2) is responsible for episomal replication of the plasmid and the *S. cerevisiae* orotidine-5'-phosphate decarboxylase (URA3) is used as selectable marker.

A 2,583-kb DNA fragment containing the open reading frame (SEQ ID NO: 1) that encodes for the mature *Saccharomycospis fibuligera* BGL1 enzyme protein sequence (SEQ ID NO: 2), was amplified with primers SSFI-L (SEQ ID NO: 3) and SSFI-R (SEQ ID NO: 4) from plasmid ySFI. The PCR product was digested with EcoRI and XhoI and ligated into the corresponding sites of plasmid yAZ4 to yield ySSFI (FIG. 2).

DNA Sequencing

The nucleotide sequences of the individual constructs were determined by amplifying DNA fragments with the Big Dye Terminator cycle-sequencing reader reaction with AmpliTaq DNA polymerase F5 (Applied Biosystems kit) using fluorescently labelled nucleotides, and the reaction mixtures were subjected to electrophoresis on an Applied Biosystems automatic DNA sequencer (model ABI Prism 377). Sequence data were analyzed by using the PC/GENE software package (IntelliGenetics, Inc., Mountain View, Calif.).

Yeast Transformation

*S. cerevisiae* SIGMA was transformed with the recombinant plasmid by the dimethyl sulfoxide-lithium acetate method described by Hill, J., et al., *Nucl Acids Res* 19:5791 (1991) and the transformants were confirmed with PCR. Disruption of the uracil phosphoribosyltransferase (FUR1) gene in the plasmid-containing *S. cerevisiae* transformants was performed to ensure auto-selection of the URA3-bearing expression plasmids in non-selective medium (Kern, L., et al., *Gene* 88:149-157 (1990)). Autoselective (fur1::LEU2) transformants were screened for on SC plates deficient in uracil and leucine. The resultant BGL1-expressing yeast strain was designated SIGMA(SSFI).

Selection for Cellobiose Utilization

*S. cerevisiae* transformants expressing the BGL1 intracellularly were grown in rich medium (YPD) to mid-log phase. The cells were appropriately diluted and plated onto YPC-medium (1% yeast extract, 2% peptone, 1% cellobiose). The plates were incubated at room temperature. After 10 days, colony-forming transformants were transferred to fresh YPC-plates. The fastest-growing transformants (based on colony size) were selected, suspended in water, and subsequently plated to fresh cellobiose-containing medium and allowed to grow for 14 days. The cells from the fastest growing colonies where then selected, suspended in liquid, plated and allowed to grow as before. This procedure was repeated for 8 months.

Enzyme Assay

β-Glucosidase activity was measured by incubating appropriately diluted cells or cell extracts with 5 mM of p-nitrophenyl-β-D-glucopyranoside (pNPG) in 50 mM citrate buffer at optimal pH and temperature for the specific enzyme according to the method previously described (Van Rooyen, R., et al., *J. Biotechnol.* 120:284-295 (2005)).

Total RNA Isolation

RNA was isolated from shake flask cultures (YP-medium containing 10 g·L$^{-1}$ of either glucose, maltose or cellobiose) of *S. cerevisiae* SIGMA(SSFI) 48 h after inoculation. RNA isolations were performed as described by Sambrook et al. (1989).

Slot Blot Analysis

Slot blot hybridizations and autoradiography were performed according to Sambrook, J., et al., *Molecular Cloning: A Laboratory Manual*, Cold Spring Harbor, N.Y. (1989), using the SCR072/0 Minifold II slot blotter (Schleicher and Schuell). The DNA probes were labeled using a random primed DIG-labeling kit (Roche) in accordance with the manufacturer's recommendations.

Medium and Inoculum

Growth was measured as absorbance at 600 nm. Batch cultivation was conducted in YP-medium containing either 10 g·L$^{-1}$ cellobiose or 7 g·L$^{-1}$ cellobiose+3 g·L$^{-1}$ maltose. Approximately 2 ml of a stationary phase culture was used to inoculate the bioreactor to an OD600 of 0.05.

Fermentation

Batch cultivations were conducted in a 1.3 L computer-controlled glass bioreactor (Bioflow 110 Non-Jacketed Vessels, New Brunswick Scientific Co.) with a total volume of 900 mL. Temperature and pH were controlled at 30° C. and pH 5.0 (by the addition of 1 M potassium hydroxide), respectively. The culture broth was mechanically agitated at 500 rpm and aerated with 0.5 L·min$^{-1}$ airflow for aerobic conditions. Dow-Corning antifoam (BDH) was added to control foaming. All cultivations were performed in duplicate.

Flow Cell Experiment

S. cerevisiae SIGMA(SSFI) grown in minimal medium (0.67% yeast nitrogen base (Difco) with amino acid supplements; 1% cellobiose) for 48 hours on a rotary shaker at 30° C. was used for inoculating the flow cell. With the peristaltic pump (Watson Marlow 205S) switched off, 200 µl of the yeast inoculum was injected into the multiple channel flow cell. The cells were allowed to establish themselves in the flow cell for 12 hours, after which the flow was resumed at 3 mL·h$^{-1}$. The yeast biofilms were maintained in minimal medium containing different carbon sources ((1%): (i) glucose, (ii) maltose and (iii) cellobiose) for 7 days at room temperature.

Analytical Methods

Samples for determination of cell density, dry cell weight and substrate consumption were taken from the fermentor at 3-4 hour intervals. Cells were removed from the samples via filtration through 0.22 µm disposable filters as previously described (Görgens, J. F., et al., *Biotechnol Bioeng* 73:238-245 (2001)). The dry cell weight of each culture was determined according to the method described by Meinander, N., et al., *Microbiology* 142:165-172 (1996).

Substrate Consumption and Product Formation

Cellobiose, maltose, ethanol, glycerol and acetic acid concentrations were determined by high-performance liquid chromatography (HPLC), with a Waters 717 injector (Milford, Mass., USA) and Agilent 1100 pump (Palo Alto, Calif., USA). The compounds were separated on an Aminex HPX87-H column (Biorad, Richmond, Calif.) at 45° C., with 5 mM H$_2$SO$_4$ at 0.6 ml min$^{-1}$ as mobile phase, and detected with a Waters 410 refractive index detector.

Calculations

Specific growth rates were calculated at individual points on the growth curve (ln OD600 vs. time) by using the four surrounding points (two on each side) on the curve to determine the slope at the specific point. The maximum of these specific growth rates for the individual fermentations was selected, and an average calculated for the strain's specific performance on each carbon source. The rates of substrate consumption were calculated from the slope of the (ln(substrate concentration)/(Dry weight) vs. time) graph.

Results and Discussion

Figure 1:
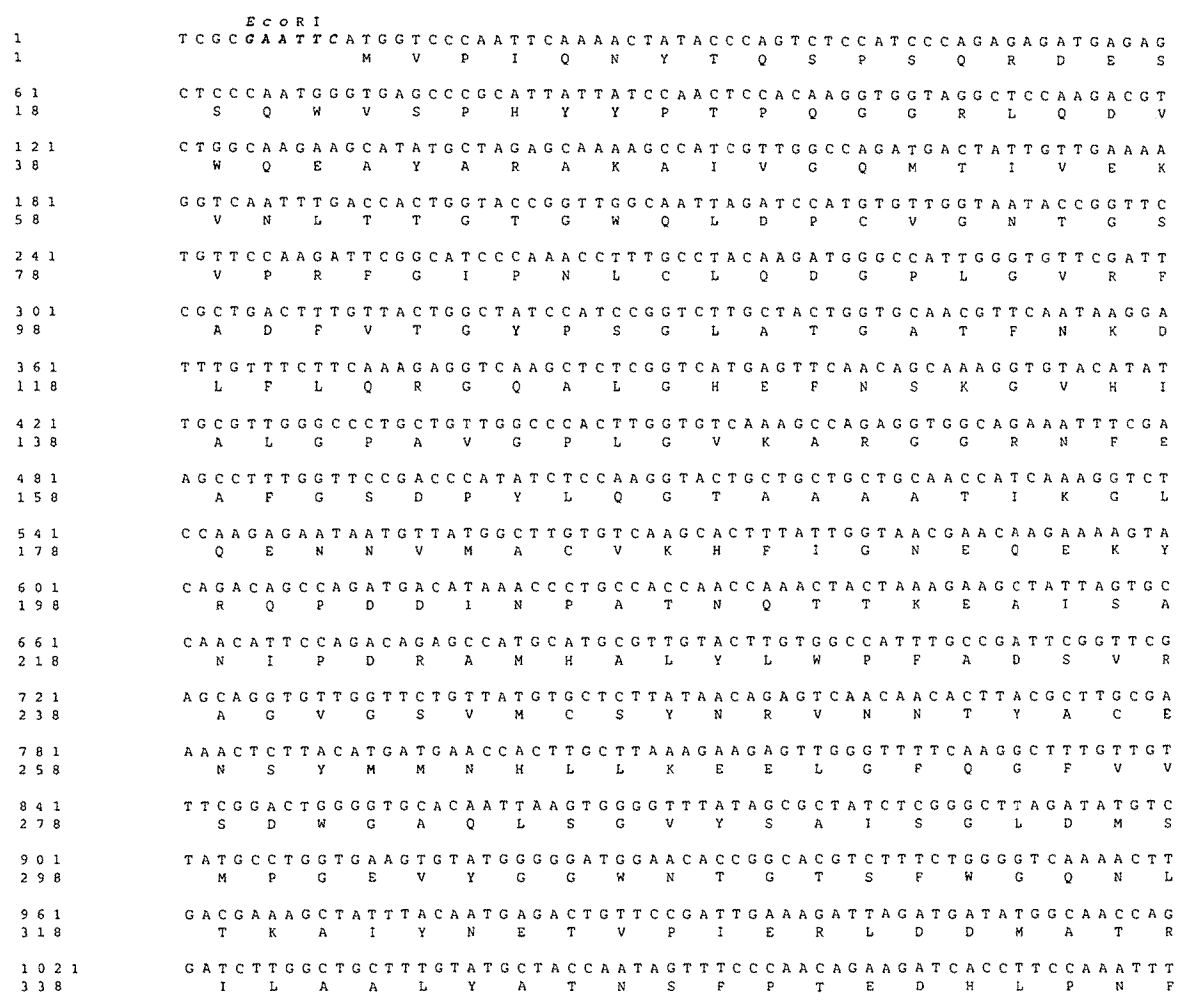
Figure 1:
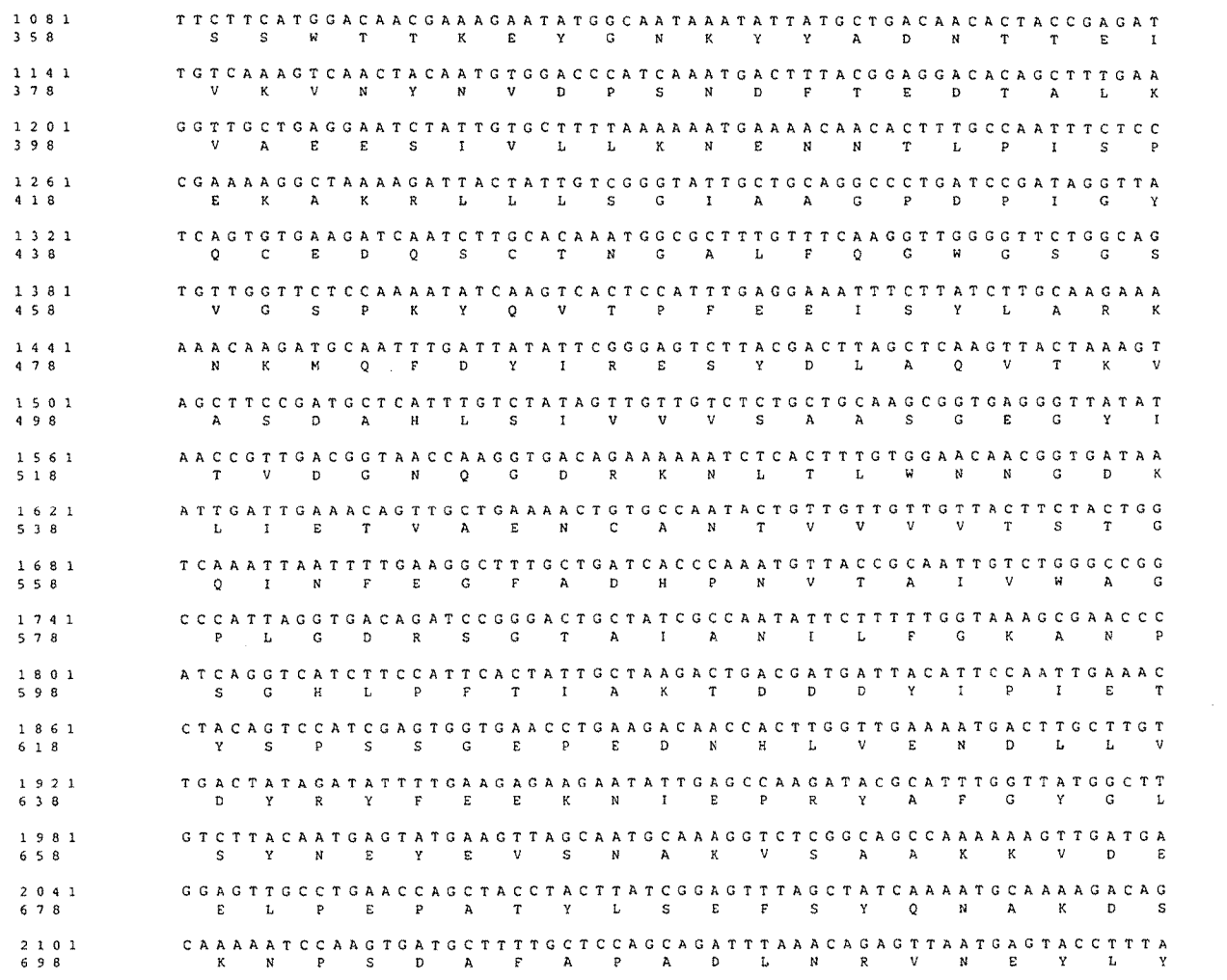

A DNA fragment (SEQ ID NO: 1) containing the mature peptide sequence of *Saccharomycopsis fibuligera* β-glucosidase (BGL1) (SEQ ID NO: 2) (FIG. 1) was cloned in an episomal yeast expression vector (FIG. 2) and transformed to *S. cerevisiae* SIGMA. Recombinant *S. fibuligera* β-glucosidase was produced in the intracellular space of the recombinant *S. cerevisiae* strain, designated SIGMA(SSFI). The SIGMA(SSFI) strain was selected on cellobiose-containing plates for uptake and subsequent utilization of cellobiose. The resulting recombinant strain was subjected to continuous selective pressure over a period of 3 months, aimed at adapting its native disaccharide transporter(s) for cellobiose uptake and subsequent hydrolysis by the intracellular β-glucosidase.

The selection was carried out by plating a dilution series of the transformed SIGMA [SSFI] stain onto YP-medium containing cellobiose as sole carbon source (50 plates). After 10 days a total of 19 colonies appeared. These colonies were each diluted in water and plated to fresh plates (every 2 weeks). After 5 months, 3 colonies grew significantly faster than the rest—they appeared after 5 days whereas the other colonies routinely appeared after 7-10 days. Therefore, they also showed significantly larger colony sizes. These 3 colonies were kept under "selective pressure" on cellobiose media for an additional 3 months. Growth of the final 3 colonies was compared with regards to OD readings.

This selection resulted in a strain with a significantly improved growth rate of 0.09 h$^{-1}$ in 10 g·L$^{-1}$ cellobiose shake-flask culture relative to the pre-selected strain which grew at rates too slow to be measured effectively in this assay.

Figure 3:
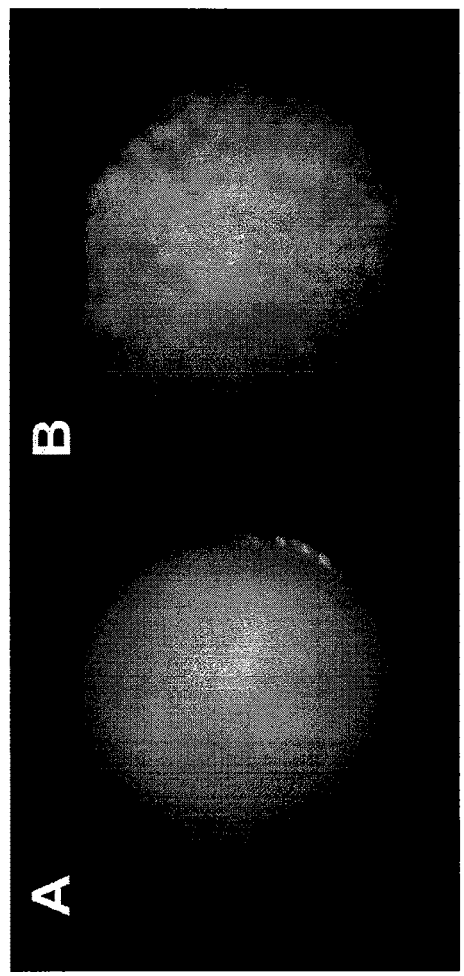
FIG. 3 depicts: (A) Wrinkled colony morphology of the enhanced cellobiose-utilizing strain after a 3 month selection procedure; and (B) the smooth colony morphology of the other is indicated at the right.

One of the 10 best cellobiose-utilizing SIGMA(SSFI) colonies displayed an unusual wrinkled colony morphology (FIG. 3). Halme et al. (2004) described a similarly wrinkled colony morphology phenotype that resulted from loss-of-function mutations in either IRA1 or IRA2, the genes encoding the yeast Ras GTPase-activating proteins. This particular cell surface alteration causes increased adhesion of *S. cerevisiae* to the agar.

Figure 4B:
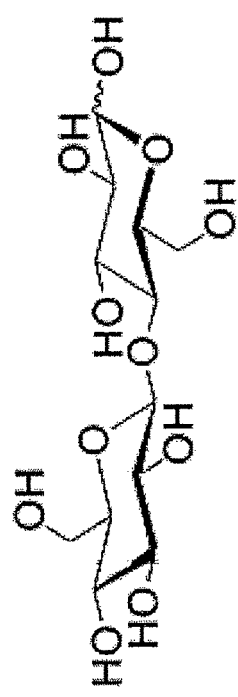
Figure 5:
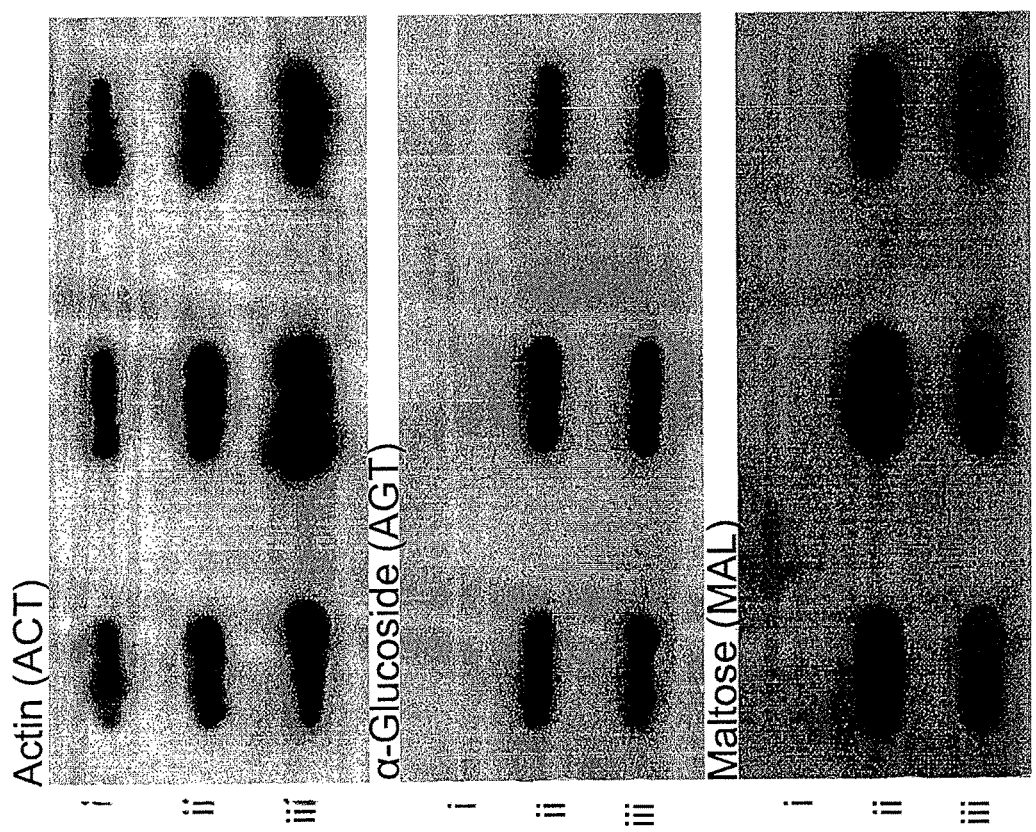
FIG. 5 depicts the RNA Bio-dot analysis of the SIGMA (SSFI) strain grown in YP-medium containing (i) glucose, (ii) maltose and (iii) cellobiose as sole carbon sources, respectively. 15 µg Total RNA from individual cultivations were loaded in each lane. DIG-labeled probes for the different transporters are indicated in the left corner of each blot.

In order to explain the mechanism by which the adapted SIGMA(SSFI) strain is able to transport and utilize cellobiose intracellularly, the inventors investigated the native disaccharide transporters of *S. cerevisiae*. Cellobiose and maltose are both disaccharides of glucose and differ only with regards to their 1,4-linkage (α- and β-linked in maltose and cellobiose, respectively). As a result, cellobiose and maltose display similar stereochemistry, as indicated in FIG. 4. Subsequent RNA Bio-Dot analysis on the total RNA from the adapted strain when grown on cellobiose and maltose as sole carbon source confirmed the induction of RNA transcripts for the native β-glucoside and maltose transporters (FIG. 5). The reference strain (before adaptation) grown in glucose-medium did not show induction of either of the transporters. These results suggest that the transport of cellobiose (presumably via the maltose permease and α-glucoside transporter) is the rate-limiting step in the utilization of cellobiose by SIGMA(SSFI). In addition, no β-glucosidase activity could be detected in the supernatant of the cellobiose-growing culture, but only in the intracellular space and therefore confirmed that the cellobiose has to be transported across the plasma membrane in order to be utilized.

The RNA Bio-Dot results obtained with the cellobiose-utilizing SIGMA(SSFI) showed that both the maltose permease and α-glucoside transporter were induced in the adapted strain (FIG. 5). Presumably, these native transporters have different affinities for cellobiose and therefore co-facilitate sugar transport at different concentrations of cellobiose, suggesting that cellobiose transport in the adapted strain is in agreement with the multi-component model described for sugar transport in *S. cerevisiae*.

Figure 6:
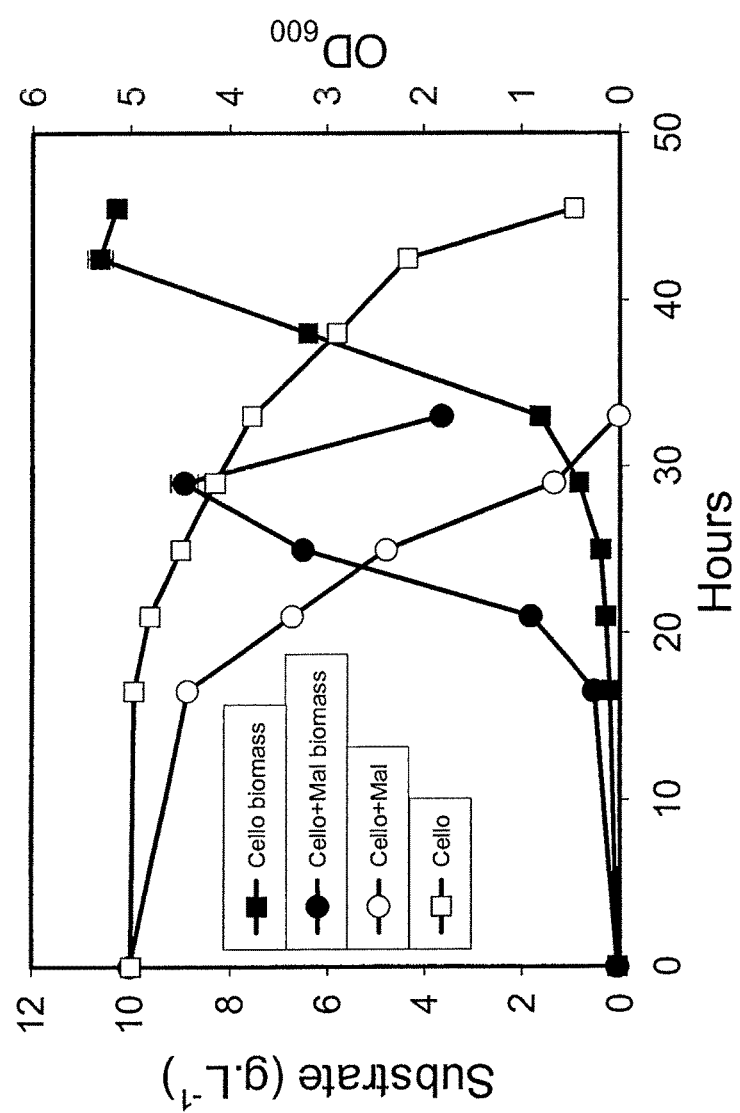
FIG. 6 depicts growth (filled symbols) and substrate consumption (open symbols) of SIGMA(SSFI) during aerobic batch cultivation in minimal medium containing (i) 10 g·L$^{-1}$ cellobiose (△) and (ii) 7 g·L$^{-1}$ cellobiose+3 g·L$^{-1}$ maltose (◇).

The adapted SIGMA(SSFI) strain was cultivated in high-performance bioreactors to determine if the rate of transport and subsequent utilization of cellobiose was sufficient to enable growth on cellobiose as sole carbon source. During aerobic cultivation, SIGMA(SSFI) was able to grow in YP-medium containing 10 g·L⁻¹ cellobiose at a maximum specific growth rate ($\mu_{max}$) of 0.17 h¹ (FIG. 6). Interestingly, when the carbon source was changed to a mixture of cellobiose and maltose (7 g·L⁻¹ cellobiose and 3 g·L⁻¹ maltose), the $\mu_{max}$ increased to 0.30 h⁻¹. The addition of maltose significantly improved the uptake of cellobiose. It was therefore presumed that the transport of cellobiose (via the combined action of the maltose permease and α-glucosidase transporter) is the rate-limiting step in the utilization of cellobiose by SIGMA(SSFI). This argument is also supported by the significantly increased substrate consumption rate of 0.37 g·g DW⁻¹·h⁻¹ when SIGMA(SSFI) was grown in the cellobiose/maltose-medium, compared to 0.25 g·g DW⁻¹·h⁻¹ when grown in cellobiose medium.

Figure 7:
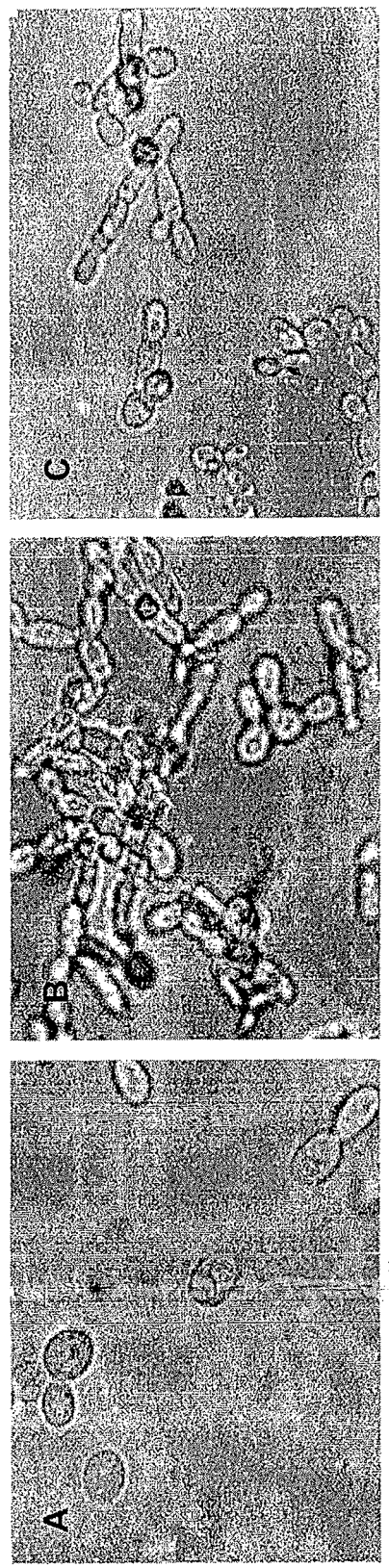
FIG. 7 depicts cell morphology of *S. cerevisiae* SIGMA (SSFI) grown in medium containing (A) glucose, (B) maltose and (C) cellobiose.
Figure 8:
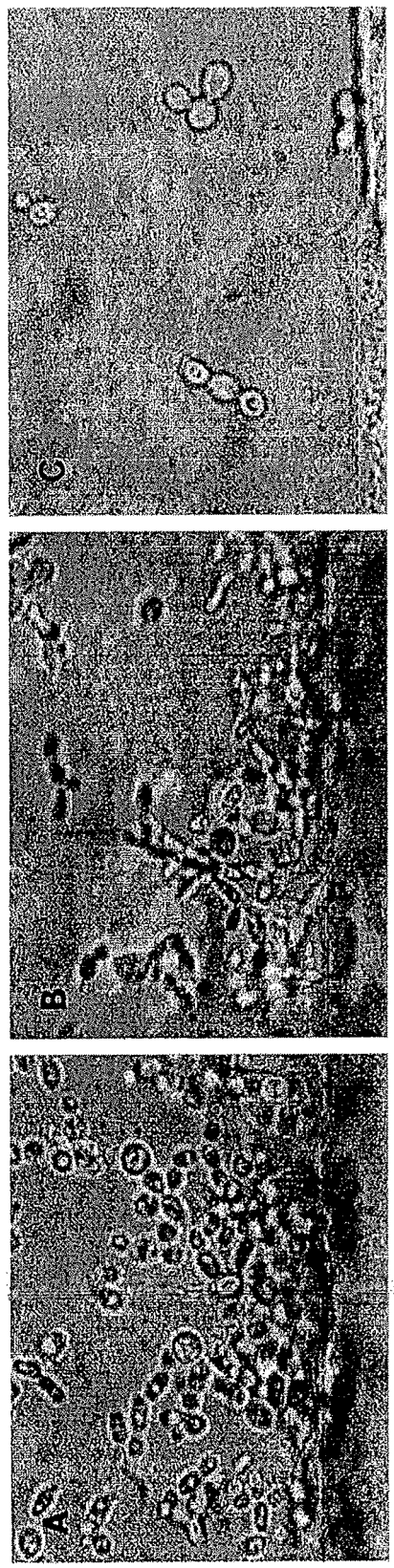
FIG. 8 depicts biofilm formation observed during growth of *S. cerevisiae* SIGMA(SSFI) after 2 days in minimal medium containing (A) maltose and (B) cellobiose. (C) is the control grown in glucose where no biofilm development took place. The surface area of the flow cell channel is highlighted with a black line in each of the photos.

The phenotypic characteristics displayed by the cellobiose-utilizing SIGMA(SSFI) strain, namely pseudohyphal growth (FIG. 7), flocculation (FIG. 5) and biofilm formation (FIG. 8), are typical adaptations that occur in S. cerevisiae in response to nutrient limitation (Gagiano, M., et al., FEMS Yeast Res 2:433-470 (2002)). A large number of genes, which are mostly involved in the signalling pathways that regulate the dimorphic switch from yeast to hyphal form, have been linked with these adaptations. It has been hypothesized that pseudohyphae grow invasively into the solid agar medium and away from the colony in order to search for nutrient-rich substrates (Bauer, F. F. and I. S. Pretorius, Focus Biotechnol—Appl Microbiol 2:109-133 (2001); Pan, X, et al., Cur Opin Microbiol 3:567-572 (2000)). Industrial processes that require easy separation of yeast cells (by sedimentation) and subsequently immobilization of the cells onto biomass support particles derive major benefit from using flocculent yeast strains (Kondo, A., et al., Appl Microbiol Biotechnol 58:291-296 (2002); Liu Y., et al., Biochem Eng J 2:229-235 (1998); Furuta, H., J Ferment Bioeng 84:169-171 (1997)).

The invention describes the adaptation of native S. cerevisiae transporters to facilitate efficient transport of cellobiose across the yeast cell membrane. This novel cellobiose-utilizing S. cerevisiae strain is an important link in the construction of a cellulolytic yeast that resembles some of the properties associated with the highly efficient cellulase enzyme systems of cellulosome-producing anaerobes. SIGMA(SSFI)'s ability to efficiently remove cellobiose from the extracellular space together with its flocculating, pseudohyphae- and biofilm-forming properties could contribute significantly to the development of S. cerevisiae that degrades cellulose.

It will be apparent to persons skilled in the art that the invention is not intended to be limited to Saccharomyces cerevisiae, and that it could also be extended to other yeasts.

Example 2

Enhanced Cellobiose Transport into S. Cerevisiae

To explore the ability of exogenous sugar transporters to facilitate cellobiose transport in S. cerevisiae, the Kllac12 gene (encoding the of the lactose permease of K. lactis) was amplified from the K. lactis genome using primers of SEQ ID NO:13 and SEQ ID NO:14, and cloned into pTZ57R (K coli cloning vector), generating pTZ-Kllac12. The DNA sequence of the K. lactis Kllac12 gene was confirmed (SEQ ID NO: 11). The Kllac12 was retrieved and cloned into expression vector YEpenoBBH, resulting in plasmid YEpenoBBH-Kllac12. The $ENO1_P$-Kllac12-$ENO1_T$ expression cassette was retrieved as a BamHI-BglII (partials) fragment and cloned onto ySSFI (containing the mature BGL). The final construct, ySSFI-Lac12, was transformed into S. cerevisiae Y294. Several transformants were tested by cultivation on cellobiose as sole carbon source. Three of the transformants were able to grow to an optical density of 2.0 to 2.4 on cellobiose medium, whereas the negative control was only able to grow to an OD of 0.4. The three transformants still displayed the his3 and trp1 phenotype (as is to be expected) and the presence of the Lac12 gene was confirmed by means of PCR.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A transformed yeast host cell comprising:
   a. a heterologous polynucleotide encoding a polypeptide comprising an amino acid sequence that is at least 95% identical to the amino acid sequence of SEQ ID NO: 2 and having β-glucosidase activity, wherein said polypeptide having β-glucosidase activity is retained in the cytoplasm of said transformed yeast host cell and is not targeted to a secretory pathway, and
   b. a heterologous polynucleotide encoding a polypeptide comprising an amino acid sequence that is at least 95% identical to the amino acid sequence of SEQ ID NO: 12 and having permease activity for transporting cellobiose into the cytoplasm of said transformed yeast host cell;
   wherein said transformed yeast host cell is able to grow on cellobiose as a sole carbon source.

2. The transformed yeast host cell of claim 1, wherein said transformed yeast host cell is a member of the genus selected from the group consisting of Saccharomyces, Kluyveromyces, Candida, Pichia, Schizosaccharomyces, Hansenula, Kloeckera, Schwanniomyces, and Yarrowia.

3. The transformed yeast host cell of claim 2, wherein said transformed yeast host cell is a member of the genus, Saccharomyces.

4. The transformed yeast host cell of claim 3, wherein said transformed yeast host cell is a member of the species, Saccharomyces cerevisiae.

5. The transformed yeast host cell of claim 1, wherein said polypeptide having β-glucosidase activity comprises the amino acid sequence of SEQ ID NO: 2.

6. The transformed yeast host cell of claim 1, wherein said transformed yeast host cell is Saccharomyces cerevisiae and wherein said polypeptide having β-glucosidase activity comprises the amino acid sequence of SEQ ID NO: 2.

7. The transformed yeast host cell of claim 1, wherein said polypeptide having permease activity comprises the amino acid sequence of SEQ ID NO: 12.

* * * * *

SEQUENCE LISTING

<160> NUMBER OF SEQ ID NOS: 76

<210> SEQ ID NO 1
<211> LENGTH: 2605
<212> TYPE: DNA
<213> ORGANISM: Saccharomycospis fibuligera

<400> SEQUENCE: 1

```
tcgcgaattc atggtcccaa ttcaaaacta tacccagtct ccatcccaga gagatgagag      60
ctcccaatgg gtgagcccgc attattatcc aactccacaa ggtggtaggc tccaagacgt     120
ctggcaagaa gcatatgcta gagcaaaagc catcgttggc cagatgacta ttgttgaaaa     180
ggtcaatttg accactggta ccggttggca attagatcca tgtgttggta ataccggttc     240
tgttccaaga ttcggcatcc caaaccttg cctacaagat gggccattgg gtgttcgatt     300
```

```
cgctgacttt gttactggct atccatccgg tcttgctact ggtgcaacgt tcaataagga    360
tttgtttctt caaagaggtc aagctctcgg tcatgagttc aacagcaaag gtgtacatat    420
tgcgttgggc cctgctgttg gcccacttgg tgtcaaagcc agaggtggca gaaatttcga    480
agcctttggt tccgacccat atctccaagg tactgctgct gctgcaacca tcaaaggtct    540
ccaagagaat aatgttatgg cttgtgtcaa gcactttatt ggtaacgaac aagaaaagta    600
cagacagcca gatgacataa accctgccac caaccaaact actaaagaag ctattagtgc    660
caacattcca gacagagcca tgcatgcgtt gtacttgtgg ccatttgccg attcggttcg    720
agcaggtgtt ggttctgtta tgtgctctta aacagagtc aacaacactt acgcttgcga    780
aaactcttac atgatgaacc acttgcttaa agaagagttg ggttttcaag ctttgttgt    840 ttcggactgg ggtgcacaat taagtggggt ttatagcgct atctcgggct tagatatgtc    900
tatgcctggt gaagtgtatg ggggatggaa caccggcacg tctttctggg gtcaaaactt    960
gacgaaagct atttacaatg agactgttcc gattgaaaga ttagatgata tggcaaccag    1020
gatcttggct gctttgtatg ctaccaatag tttcccaaca gaagatcacc ttccaaattt    1080
ttcttcatgg acaacgaaag aatatggcaa taaatattat gctgacaaca ctaccgagat    1140
tgtcaaagtc aactacaatg tggacccatc aaatgacttt acggaggaca cagctttgaa    1200
ggttgctgag gaatctattg tgcttttaaa aaatgaaaac aacactttgc caatttctcc    1260
cgaaaaggct aaaagattac tattgtcggg tattgctgca ggccctgatc cgataggtta    1320
tcagtgtgaa gatcaatctt gcacaaatgg cgctttgttt caaggttggg gttctggcag    1380
tgttggttct ccaaaaatatc aagtcactcc atttgaggaa atttcttatc ttgcaagaaa    1440
aaacaagatg caatttgatt atattcggga gtcttacgac ttagctcaag ttactaaagt    1500
agcttccgat gctcatttgt ctatagttgt tgtctctgct gcaagcggtg agggttatat    1560
aaccgttgac ggtaaccaag gtgacagaaa aaatctcact tgtgtggaaca acggtgataa    1620 attgattgaa acagttgctg aaaactgtgc caatactgtt gttgttgtta cttctactgg    1680
tcaaattaat tttgaaggct tgctgatca cccaaatgtt accgcaattg tctgggccgg    1740
cccattaggt gacagatccg ggactgctat cgccaatatt ctttttggta aagcgaaccc    1800
atcaggtcat cttccattca ctattgctaa gactgacgat gattacattc caattgaaac    1860
ctacagtcca tcgagtggtg aacctgaaga caaccacttg gttgaaaatg acttgcttgt    1920
tgactataga tattttgaag agaagaatat tgagccaaga tacgcatttg gttatggctt    1980
gtcttacaat gagtatgaag ttagcaatgc aaaggtctcg gcagccaaaa aagttgatga    2040
ggagttgcct gaaccagcta cctacttatc ggagtttagc tatcaaaatg caaaagacag    2100
caaaaatcca agtgatgctt tgctccagc agatttaaac agagttaatg agtaccttta    2160
tccatattta gatagcaatg ttaccttaaa agacggaaac tatgagtatc ctgatggcta    2220
cagcactgag caaagaacaa cacctaacca acctgggggc ggcttgggag caacgatgc    2280 tttgtgggag gtcgcttata actccactga taagtttgtt ccacagggta actccactga    2340
taagtttgtt ccacagttgt atttgaaaca ccctgaggat ggcaagtttg aaaccccctat    2400 tcaattgaga gggtttgaaa aggttgagtt gtccccgggt gagaagaaga cagttgatttt    2460 gaggcttttg agaagagatc ttagtgtgtg ggataccacc agacagtctt ggatcgttga    2520
atctggtact tatgaggcct taattggcgt tgctgttaat gatatcaaga catctgtcct    2580
gtttactatt tgaccgctcg agcgg                                           2605
```

```
<210> SEQ ID NO 2
<211> LENGTH: 860
<212> TYPE: PRT
<213> ORGANISM: Saccharomycospis fibuligera

<400> SEQUENCE: 2

Met Val Pro Ile Gln Asn Tyr Thr Gln Ser Pro Ser Gln Arg Asp Glu
 1               5                  10                  15

Ser Ser Gln Trp Val Ser Pro His Tyr Tyr Pro Thr Pro Gln Gly Gly
            20                  25                  30

Arg Leu Gln Asp Val Trp Gln Glu Ala Tyr Ala Arg Ala Lys Ala Ile
        35                  40                  45

Val Gly Gln Met Thr Ile Val Glu Lys Val Asn Leu Thr Thr Gly Thr
50                  55                  60

Gly Trp Gln Leu Asp Pro Cys Val Gly Asn Thr Gly Ser Val Pro Arg
65                  70                  75                  80

Phe Gly Ile Pro Asn Leu Cys Leu Gln Asp Gly Pro Leu Gly Val Arg
                85                  90                  95

Phe Ala Asp Phe Val Thr Gly Tyr Pro Ser Gly Leu Ala Thr Gly Ala
            100                 105                 110

Thr Phe Asn Lys Asp Leu Phe Leu Gln Arg Gly Gln Ala Leu Gly His
        115                 120                 125

Glu Phe Asn Ser Lys Gly Val His Ile Ala Leu Gly Pro Ala Val Gly
130                 135                 140

Pro Leu Gly Val Lys Ala Arg Gly Gly Arg Asn Phe Glu Ala Phe Gly
145                 150                 155                 160

Ser Asp Pro Tyr Leu Gln Gly Thr Ala Ala Ala Thr Ile Lys Gly
                165                 170                 175

Leu Gln Glu Asn Asn Val Met Ala Cys Val Lys His Phe Ile Gly Asn
            180                 185                 190

Glu Gln Glu Lys Tyr Arg Gln Pro Asp Asp Ile Asn Pro Ala Thr Asn
        195                 200                 205

Gln Thr Thr Lys Glu Ala Ile Ser Ala Asn Ile Pro Asp Arg Ala Met
210                 215                 220

His Ala Leu Tyr Leu Trp Pro Phe Ala Asp Ser Val Arg Ala Gly Val
225                 230                 235                 240

Gly Ser Val Met Cys Ser Tyr Asn Arg Val Asn Asn Thr Tyr Ala Cys
                245                 250                 255

Glu Asn Ser Tyr Met Met Asn His Leu Leu Lys Glu Glu Leu Gly Phe
            260                 265                 270

Gln Gly Phe Val Val Ser Asp Trp Gly Ala Gln Leu Ser Gly Val Tyr
        275                 280                 285

Ser Ala Ile Ser Gly Leu Asp Met Ser Met Pro Gly Glu Val Tyr Gly
290                 295                 300

Gly Trp Asn Thr Gly Thr Ser Phe Trp Gly Gln Asn Leu Thr Lys Ala
305                 310                 315                 320

Ile Tyr Asn Glu Thr Val Pro Ile Glu Arg Leu Asp Asp Met Ala Thr
                325                 330                 335

Arg Ile Leu Ala Ala Leu Tyr Ala Thr Asn Ser Phe Pro Thr Glu Asp
            340                 345                 350

His Leu Pro Asn Phe Ser Ser Trp Thr Thr Lys Glu Tyr Gly Asn Lys
        355                 360                 365

Tyr Tyr Ala Asp Asn Thr Thr Glu Ile Val Lys Val Asn Tyr Asn Val
370                 375                 380
```

```
Asp Pro Ser Asn Asp Phe Thr Glu Asp Thr Ala Leu Lys Val Ala Glu
385                 390                 395                 400

Glu Ser Ile Val Leu Leu Lys Asn Glu Asn Asn Thr Leu Pro Ile Ser
            405                 410                 415

Pro Glu Lys Ala Lys Arg Leu Leu Ser Gly Ile Ala Ala Gly Pro
        420                 425                 430

Asp Pro Ile Gly Tyr Gln Cys Glu Asp Gln Ser Cys Thr Asn Gly Ala
        435                 440                 445

Leu Phe Gln Gly Trp Gly Ser Gly Val Gly Ser Pro Lys Tyr Gln
    450                 455                 460

Val Thr Pro Phe Glu Glu Ile Ser Tyr Leu Ala Arg Lys Asn Lys Met
465                 470                 475                 480

Gln Phe Asp Tyr Ile Arg Glu Ser Tyr Asp Leu Ala Gln Val Thr Lys
            485                 490                 495

Val Ala Ser Asp Ala His Leu Ser Ile Val Val Ser Ala Ala Ser
            500                 505                 510

Gly Glu Gly Tyr Ile Thr Val Asp Gly Asn Gln Gly Asp Arg Lys Asn
        515                 520                 525

Leu Thr Leu Trp Asn Asn Gly Asp Lys Leu Ile Glu Thr Val Ala Glu
    530                 535                 540

Asn Cys Ala Asn Thr Val Val Val Thr Ser Thr Gly Gln Ile Asn
545                 550                 555                 560

Phe Glu Gly Phe Ala Asp His Pro Asn Val Thr Ala Ile Val Trp Ala
                565                 570                 575

Gly Pro Leu Gly Asp Arg Ser Gly Thr Ala Ile Ala Asn Ile Leu Phe
        580                 585                 590

Gly Lys Ala Asn Pro Ser Gly His Leu Pro Phe Thr Ile Ala Lys Thr
    595                 600                 605

Asp Asp Asp Tyr Ile Pro Ile Glu Thr Tyr Ser Pro Ser Ser Gly Glu
        610                 615                 620

Pro Glu Asp Asn His Leu Val Glu Asn Asp Leu Leu Val Asp Tyr Arg
625                 630                 635                 640

Tyr Phe Glu Glu Lys Asn Ile Glu Pro Arg Tyr Ala Phe Gly Tyr Gly
            645                 650                 655

Leu Ser Tyr Asn Glu Tyr Glu Val Ser Asn Ala Lys Val Ser Ala Ala
        660                 665                 670

Lys Lys Val Asp Glu Glu Leu Pro Glu Pro Ala Thr Tyr Leu Ser Glu
        675                 680                 685

Phe Ser Tyr Gln Asn Ala Lys Asp Ser Lys Asn Pro Ser Asp Ala Phe
    690                 695                 700

Ala Pro Ala Asp Leu Asn Arg Val Asn Glu Tyr Leu Tyr Pro Tyr Leu
705                 710                 715                 720

Asp Ser Asn Val Thr Leu Lys Asp Gly Asn Tyr Glu Tyr Pro Asp Gly
            725                 730                 735

Tyr Ser Thr Glu Gln Arg Thr Thr Pro Asn Gln Pro Gly Gly Gly Leu
        740                 745                 750

Gly Gly Asn Asp Ala Leu Trp Glu Val Ala Tyr Asn Ser Thr Asp Lys
    755                 760                 765

Phe Val Pro Gln Gly Asn Ser Thr Asp Lys Phe Val Pro Gln Leu Tyr
    770                 775                 780

Leu Lys His Pro Glu Asp Gly Lys Phe Glu Thr Pro Ile Gln Leu Arg
785                 790                 795                 800

Gly Phe Glu Lys Val Glu Leu Ser Pro Gly Glu Lys Lys Thr Val Asp
```

```
                    805                 810                 815
Leu Arg Leu Leu Arg Arg Asp Leu Ser Val Trp Asp Thr Thr Arg Gln
            820                 825                 830

Ser Trp Ile Val Glu Ser Gly Thr Tyr Glu Ala Leu Ile Gly Val Ala
        835                 840                 845

Val Asn Asp Ile Lys Thr Ser Val Leu Phe Thr Ile
    850                 855                 860
```

```
<210> SEQ ID NO 3
<211> LENGTH: 34
<212> TYPE: DNA
<213> ORGANISM: Artificial Sequence
<220> FEATURE:
<223> OTHER INFORMATION: Synthetic SSF1 Primer

<400> SEQUENCE: 3
tcgcgaattc atggtcccaa ttcaaaacta tacc                            34

<210> SEQ ID NO 4
<211> LENGTH: 35
<212> TYPE: DNA
<213> ORGANISM: Artificial Sequence
<220> FEATURE:
<223> OTHER INFORMATION: Synthetic SSF1 Primer

<400> SEQUENCE: 4
ccgctcgagc ggtcaaatag taaacaggac agatg                           35

<210> SEQ ID NO 5
<211> LENGTH: 19
<212> TYPE: DNA
<213> ORGANISM: Artificial Sequence
<220> FEATURE:
<223> OTHER INFORMATION: Synthetic ACT Primer

<400> SEQUENCE: 5
actgaagctc caatgaacc                                             19

<210> SEQ ID NO 6
<211> LENGTH: 20
<212> TYPE: DNA
<213> ORGANISM: Artificial Sequence
<220> FEATURE:
<223> OTHER INFORMATION: Synthetic ACT Primer

<400> SEQUENCE: 6
catcgacatc acacttcatg                                            20

<210> SEQ ID NO 7
<211> LENGTH: 18
<212> TYPE: DNA
<213> ORGANISM: Artificial Sequence
<220> FEATURE:
<223> OTHER INFORMATION: Synthetic AGT Primer

<400> SEQUENCE: 7
atgattgctg tgggacaa                                              18

<210> SEQ ID NO 8
<211> LENGTH: 21
<212> TYPE: DNA
<213> ORGANISM: Artificial Sequence
<220> FEATURE:
<223> OTHER INFORMATION: Synthetic AGT Primer
```

```
<400> SEQUENCE: 8
gtctcgttct tcttccatta a                                          21

<210> SEQ ID NO 9
<211> LENGTH: 18
<212> TYPE: DNA
<213> ORGANISM: Artificial Sequence
<220> FEATURE:
<223> OTHER INFORMATION: Synthetic MAL Primer

<400> SEQUENCE: 9
atgattgctg tgggacaa                                              18

<210> SEQ ID NO 10
<211> LENGTH: 23
<212> TYPE: DNA
<213> ORGANISM: Artificial Sequence
<220> FEATURE:
<223> OTHER INFORMATION: Synthetic MAL Primer

<400> SEQUENCE: 10
agacaagtaa ttctcgttct tct                                        23

<210> SEQ ID NO 11
<211> LENGTH: 1764
<212> TYPE: DNA
<213> ORGANISM: Kluyveromyces lactis

<400> SEQUENCE: 11
atggcagatc attcgagcag ctcatcttcg ctgcagaaga agccaattaa tactatcgag    60
cataaagaca ctttgggcaa tgatcgggat cacaaggaag ccttgaacag tgataatgat   120
aatacttctg gattgaaaat caatggtgtc cccatcgagg acgctagaga ggaagtgctc   180
ttaccaggtt acttgtcgaa gcaatattac aaattgtacg gtttatgttt tataacatat   240
ctgtgtgcta ctatgcaagg ttatgatggg gctttaatgg gttctatcta taccgaagat   300
gcatatttga atactacca tttggatatt aactcatcct ctggtactgg tctagtgttc   360 tctatttca cgttggtca aatttgcggt gcattctttg ttcctcttat ggattggaaa    420
ggtagaaaac ctgctatttt aattgggtgt ctgggtgttg ttattggtgc tattatttcg   480
tctttaacaa caacaaagag tgcattaatt ggtggtagat ggtcgtggc cttttcgct    540 acaatcgcta atgcagcagc tccaacatac tgtgcagaag tggctccagc tcacttaaga   600
ggtaaggttg caggtcttta taacacccct tggtctgtcg gttccattgt tgctgccttt   660
agcacttacg gtaccaacaa aaacttccct aactcctcca aggcttttaa gattccatta   720
tacttacaaa tgatgttccc aggtcttgtg tgtatatttg gttggttaat cccagaatct   780
ccaagatggt tggttggtgt tggccgtgag gaagaagctc gtgaattcat tatcaaatac   840
cacttaaatg gcgatagaac tcatccatta ttggatatgg agatggcaga ataatagaa   900 tctttccatg gtacagattt atcaaaccct ctagaaatgt tagatgtaag gagcttattc   960
agaacgagat cggataggta cagagcaatg ttggttatac ttatggcttg gttcggtcaa  1020
ttttccggta acaatgtgtg ttcgtactat ttgcctacca tgttgagaaa tgttggtatg  1080
aagagtgtct cattgaatgt gttaatgaat ggtgtttatt ccatcgtcac ttggatttct  1140
tcaatttgcg gtgcattctt tattgataag attggtagaa gggaaggttt ccttggttct  1200
atctcaggtc tgcattagc attgacaggt ctatctatct gtactgctcg ttatgagaag  1260
actaagaaga gagtgcttc caatggtgca ttggtgttca tttatctctt tggtggtatc  1320
```

-continued

```
ttttcttttg ctttcactcc aatgcaatcc atgtactcaa cagaagtgtc tacaaacttg    1380
acgagatcta aggcccaact cctcaacttt gtggtttctg gtgttgccca atttgttaat    1440
caatttgcta ctccaaaggc aatgaagaat atcaaatatt ggttctatgt gttctacgtt    1500
ttcttcgata ttttcgaatt tattgttatc tacttcttct tcgttgaaac taagggtaga    1560
agcttagaag aattagaagt tgtctttgaa gctccaaacc caagaaaggc atccgttgat    1620
caagcattct tggctcaagt cagggcaact ttggtccaac gaaatgacgt tagagttgca    1680
aatgctcaaa atttgaaaga gcaagagcct ctaaagagcg atgctgatca tgtcgaaaag    1740
ctttcagagg cagaatctgt ttaa                                           1764
```

<210> SEQ ID NO 12
<211> LENGTH: 587
<212> TYPE: PRT
<213> ORGANISM: Kluyveromyces lactis

<400> SEQUENCE: 12

```
Met Ala Asp His Ser Ser Ser Ser Ser Leu Gln Lys Lys Pro Ile
1               5                   10                  15

Asn Thr Ile Glu His Lys Asp Thr Leu Gly Asn Asp Arg Asp His Lys
            20                  25                  30

Glu Ala Leu Asn Ser Asp Asn Asp Asn Thr Ser Gly Leu Lys Ile Asn
        35                  40                  45

Gly Val Pro Ile Glu Asp Ala Arg Glu Glu Val Leu Leu Pro Gly Tyr
    50                  55                  60

Leu Ser Lys Gln Tyr Tyr Lys Leu Tyr Gly Leu Cys Phe Ile Thr Tyr
65                  70                  75                  80

Leu Cys Ala Thr Met Gln Gly Tyr Asp Gly Ala Leu Met Gly Ser Ile
                85                  90                  95

Tyr Thr Glu Asp Ala Tyr Leu Lys Tyr His Leu Asp Ile Asn Ser
            100                 105                 110

Ser Ser Gly Thr Gly Leu Val Phe Ser Ile Phe Asn Val Gly Gln Ile
        115                 120                 125

Cys Gly Ala Phe Phe Val Pro Leu Met Asp Trp Lys Gly Arg Lys Pro
    130                 135                 140

Ala Ile Leu Ile Gly Cys Leu Gly Val Val Ile Gly Ala Ile Ile Ser
145                 150                 155                 160

Ser Leu Thr Thr Thr Lys Ser Ala Leu Ile Gly Gly Arg Trp Phe Val
                165                 170                 175

Ala Phe Phe Ala Thr Ile Ala Asn Ala Ala Pro Thr Tyr Cys Ala
            180                 185                 190

Glu Val Ala Pro Ala His Leu Arg Gly Lys Val Ala Gly Leu Tyr Asn
        195                 200                 205

Thr Leu Trp Ser Val Gly Ser Ile Val Ala Ala Phe Ser Thr Tyr Gly
    210                 215                 220

Thr Asn Lys Asn Phe Pro Asn Ser Ser Lys Ala Phe Lys Ile Pro Leu
225                 230                 235                 240

Tyr Leu Gln Met Met Phe Pro Gly Leu Val Cys Ile Phe Gly Trp Leu
                245                 250                 255

Ile Pro Glu Ser Pro Arg Trp Leu Val Gly Val Gly Arg Glu Glu Glu
            260                 265                 270

Ala Arg Glu Phe Ile Ile Lys Tyr His Leu Asn Gly Asp Arg Thr His
        275                 280                 285
```

```
Pro Leu Leu Asp Met Glu Met Ala Glu Ile Ile Glu Ser Phe His Gly
        290                 295                 300
Thr Asp Leu Ser Asn Pro Leu Glu Met Leu Asp Val Arg Ser Leu Phe
305                 310                 315                 320
Arg Thr Arg Ser Asp Arg Tyr Arg Ala Met Leu Val Ile Leu Met Ala
                325                 330                 335
Trp Phe Gly Gln Phe Ser Gly Asn Asn Val Cys Ser Tyr Tyr Leu Pro
                340                 345                 350
Thr Met Leu Arg Asn Val Gly Met Lys Ser Val Ser Leu Asn Val Leu
                355                 360                 365
Met Asn Gly Val Tyr Ser Ile Val Thr Trp Ile Ser Ser Ile Cys Gly
        370                 375                 380
Ala Phe Phe Ile Asp Lys Ile Gly Arg Arg Glu Gly Phe Leu Gly Ser
385                 390                 395                 400
Ile Ser Gly Ala Ala Leu Ala Leu Thr Gly Leu Ser Ile Cys Thr Ala
                    405                 410                 415
Arg Tyr Glu Lys Thr Lys Lys Ser Ala Ser Asn Gly Ala Leu Val
                420                 425                 430
Phe Ile Tyr Leu Phe Gly Gly Ile Phe Ser Phe Ala Phe Thr Pro Met
        435                 440                 445
Gln Ser Met Tyr Ser Thr Glu Val Ser Thr Asn Leu Thr Arg Ser Lys
    450                 455                 460
Ala Gln Leu Leu Asn Phe Val Val Ser Gly Val Ala Gln Phe Val Asn
465                 470                 475                 480
Gln Phe Ala Thr Pro Lys Ala Met Lys Asn Ile Lys Tyr Trp Phe Tyr
                485                 490                 495
Val Phe Tyr Val Phe Phe Asp Ile Phe Glu Phe Ile Val Ile Tyr Phe
                500                 505                 510
Phe Phe Val Glu Thr Lys Gly Arg Ser Leu Glu Glu Leu Glu Val Val
        515                 520                 525
Phe Glu Ala Pro Asn Pro Arg Lys Ala Ser Val Asp Gln Ala Phe Leu
    530                 535                 540
Ala Gln Val Arg Ala Thr Leu Val Gln Arg Asn Asp Val Arg Val Ala
545                 550                 555                 560
Asn Ala Gln Asn Leu Lys Glu Gln Pro Leu Lys Ser Asp Ala Asp
                565                 570                 575
His Val Glu Lys Leu Ser Glu Ala Glu Ser Val
                580                 585

<210> SEQ ID NO 13
<211> LENGTH: 25
<212> TYPE: DNA
<213> ORGANISM: Artificial Sequence
<220> FEATURE:
<223> OTHER INFORMATION: Synthetic Kllac12 Primer

<400> SEQUENCE: 13
cgatatcaaa tggcagatca ttcga                                         25

<210> SEQ ID NO 14
<211> LENGTH: 26
<212> TYPE: DNA
<213> ORGANISM: Artificial Sequence
<220> FEATURE:
<223> OTHER INFORMATION: Synthetic Kllac12 Primer

<400> SEQUENCE: 14
```

```
actcgagggc tttaaacaga ttctgc                                                    26
```

<210> SEQ ID NO 15
<211> LENGTH: 860
<212> TYPE: PRT
<213> ORGANISM: Aspergillus aculeatus

<400> SEQUENCE: 15

```
Met Lys Leu Ser Trp Leu Glu Ala Ala Leu Thr Ala Ala Ser Val
1               5                   10                  15

Val Ser Ala Asp Glu Leu Ala Phe Ser Pro Pro Phe Tyr Pro Ser Pro
            20                  25                  30

Trp Ala Asn Gly Gln Gly Glu Trp Ala Glu Ala Tyr Gln Arg Ala Val
            35                  40                  45

Ala Ile Val Ser Gln Met Thr Leu Asp Glu Lys Val Asn Leu Thr Thr
    50                  55                  60

Gly Thr Gly Trp Glu Leu Glu Lys Cys Val Gly Gln Thr Gly Gly Val
65              70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ile Asp Val Gln Leu Gly Pro Ala
130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
            180                 185                 190

Leu Asn Glu Gln Glu His Phe Arg Gln Val Ala Glu Ala Ala Gly Tyr
        195                 200                 205

Gly Phe Asn Ile Ser Asp Thr Ile Ser Ser Asn Val Asp Asp Lys Thr
210                 215                 220

Ile His Glu Met Tyr Leu Trp Pro Phe Ala Asp Ala Val Arg Ala Gly
225                 230                 235                 240

Val Gly Ala Ile Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Gly Ala His His Ser Gly Val
        275                 280                 285

Gly Ser Ala Leu Ala Gly Leu Asp Met Ser Met Pro Gly Asp Ile Thr
290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Tyr Gln Pro
            340                 345                 350

Pro Asn Phe Ser Ser Trp Thr Arg Asp Glu Tyr Gly Phe Lys Tyr Phe
        355                 360                 365
```

-continued

```
Tyr Pro Gln Glu Gly Pro Tyr Glu Lys Val Asn His Phe Val Asn Val
    370                 375                 380

Gln Arg Asn His Ser Glu Val Ile Arg Lys Leu Gly Ala Asp Ser Thr
385                 390                 395                 400

Val Leu Leu Lys Asn Asn Ala Leu Pro Leu Thr Gly Lys Glu Arg
            405                 410                 415

Lys Val Ala Ile Leu Gly Glu Asp Ala Gly Ser Asn Ser Tyr Gly Ala
                420                 425                 430

Asn Gly Cys Ser Asp Arg Gly Cys Asp Asn Gly Thr Leu Ala Met Ala
        435                 440                 445

Trp Gly Ser Gly Thr Ala Glu Phe Pro Tyr Leu Val Thr Pro Glu Gln
450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
                485                 490                 495

Ser Val Ser Leu Val Phe Val Asn Ser Asp Ala Gly Glu Gly Tyr Ile
            500                 505                 510

Ser Val Asp Gly Asn Glu Gly Asp Arg Asn Asn Leu Thr Leu Trp Lys
        515                 520                 525

Asn Gly Asp Asn Leu Ile Lys Ala Ala Ala Asn Asn Cys Asn Asn Thr
530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gly
        595                 600                 605

Asp Tyr Leu Val Arg Glu Leu Asn Asn Gly Asn Gly Ala Pro Gln Asp
610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
                645                 650                 655

Phe Asn Tyr Ser Gly Leu His Ile Gln Val Leu Asn Ala Ser Ser Asn
            660                 665                 670

Ala Gln Val Ala Thr Glu Thr Gly Ala Ala Pro Thr Phe Gly Gln Val
        675                 680                 685

Gly Asn Ala Ser Asp Tyr Val Tyr Pro Glu Gly Leu Thr Arg Ile Ser
690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
770                 775                 780

Val Ser Leu Gly Gly Pro Asn Glu Pro Lys Val Val Leu Arg Lys Phe
```

```
                785                 790                 795                 800
Asp Arg Leu Thr Leu Lys Pro Ser Glu Glu Thr Val Trp Thr Thr Thr
                    805                 810                 815

Leu Thr Arg Arg Asp Leu Ser Asn Trp Asp Val Ala Ala Gln Asp Trp
                820                 825                 830

Val Ile Thr Ser Tyr Pro Lys Lys Val His Val Gly Ser Ser Ser Arg
                835                 840                 845

Gln Leu Pro Leu His Ala Ala Leu Pro Lys Val Gln
        850                 855                 860

<210> SEQ ID NO 16
<211> LENGTH: 469
<212> TYPE: PRT
<213> ORGANISM: Bacillus subtilis

<400> SEQUENCE: 16

Met Ser Ser Asn Glu Lys Arg Phe Pro Glu Gly Phe Leu Trp Gly Gly
1               5                   10                  15

Ala Val Ala Ala Asn Gln Val Glu Gly Ala Tyr Asn Glu Gly Gly Lys
                20                  25                  30

Gly Leu Ser Thr Ala Asp Val Ser Pro Asn Gly Ile Met Ser Pro Phe
            35                  40                  45

Asp Glu Ser Met Thr Ser Leu Asn Leu Tyr His Asn Gly Ile Asp Phe
        50                  55                  60

Tyr His Arg Tyr Lys Glu Asp Ile Ala Leu Phe Ala Glu Met Gly Phe
65                  70                  75                  80

Lys Ala Phe Arg Thr Ser Ile Ala Trp Thr Arg Ile Phe Pro Asn Gly
                85                  90                  95

Asp Glu Glu Pro Asn Glu Glu Gly Leu Arg Phe Tyr Asp Asp Leu
                100                 105                 110

Phe Asp Glu Leu Leu Lys His His Ile Glu Pro Val Val Thr Ile Ser
        115                 120                 125

His Tyr Glu Met Pro Leu Gly Leu Val Lys Asn Tyr Gly Gly Trp Lys
    130                 135                 140

Asn Arg Lys Val Ile Glu Phe Tyr Glu Arg Tyr Ala Lys Thr Val Phe
145                 150                 155                 160

Lys Arg Tyr Gln His Lys Val Lys Tyr Trp Met Thr Phe Asn Glu Ile
                165                 170                 175

Asn Val Val Leu His Ala Pro Phe Thr Gly Gly Gly Leu Val Phe Glu
                180                 185                 190

Glu Gly Glu Asn Lys Leu Asn Ala Met Tyr Gln Ala Ala His His Gln
            195                 200                 205

Phe Val Ala Ser Ala Leu Ala Val Lys Ala Gly His Asp Ile Ile Pro
        210                 215                 220

Asp Ser Lys Ile Gly Cys Met Ile Ala Ala Thr Thr Thr Tyr Pro Met
225                 230                 235                 240

Thr Ser Lys Pro Glu Asp Val Phe Ala Ala Met Glu Asn Glu Arg Lys
                245                 250                 255

Thr Leu Phe Phe Ser Asp Val Gln Ala Arg Gly Ala Tyr Pro Gly Tyr
                260                 265                 270

Met Lys Arg Tyr Leu Ala Glu Asn Asn Ile Glu Ile Glu Met Ala Glu
            275                 280                 285

Gly Asp Glu Glu Leu Leu Lys Glu His Thr Val Asp Tyr Ile Gly Phe
        290                 295                 300
```

```
Ser Tyr Tyr Met Ser Met Ala Ala Ser Thr Asp Pro Glu Glu Leu Ala
305                 310                 315                 320

Lys Ser Gly Gly Asn Leu Leu Gly Gly Val Lys Asn Pro Tyr Leu Lys
            325                 330                 335

Ser Ser Glu Trp Gly Trp Gln Ile Asp Pro Lys Gly Leu Arg Ile Thr
        340                 345                 350

Leu Asn Thr Leu Tyr Asp Arg Tyr Gln Lys Pro Leu Phe Ile Val Glu
    355                 360                 365

Asn Gly Leu Gly Ala Val Asp Lys Val Glu Glu Asp Gly Thr Ile Gln
370                 375                 380

Asp Asp Tyr Arg Ile Asn Tyr Leu Arg Asp His Leu Ile Glu Ala Arg
385                 390                 395                 400

Glu Ala Ile Ala Asp Gly Val Glu Leu Ile Gly Tyr Thr Ser Trp Gly
            405                 410                 415

Pro Ile Asp Leu Val Ser Ala Ser Thr Ala Glu Met Lys Lys Arg Tyr
        420                 425                 430

Gly Phe Ile Tyr Val Asp Arg Asp Asn Glu Gly Asn Gly Thr Phe Asn
    435                 440                 445

Arg Ile Lys Lys Lys Ser Phe Asn Trp Tyr Gln Gln Val Ile Ala Thr
450                 455                 460

Asn Gly Glu Ser Leu
465

<210> SEQ ID NO 17
<211> LENGTH: 876
<212> TYPE: PRT
<213> ORGANISM: Saccharomycopsis fibuligera

<400> SEQUENCE: 17

Met Leu Met Ile Val Gln Leu Leu Val Phe Ala Leu Gly Leu Ala Val
1               5                   10                  15

Ala Val Pro Ile Gln Asn Tyr Thr Gln Ser Pro Ser Gln Arg Asp Glu
            20                  25                  30

Ser Ser Gln Trp Val Ser Pro His Tyr Tyr Pro Thr Pro Gln Gly Gly
        35                  40                  45

Arg Leu Gln Asp Val Trp Gln Glu Ala Tyr Ala Arg Ala Lys Ala Ile
    50                  55                  60

Val Gly Gln Met Thr Ile Val Glu Lys Val Asn Leu Thr Thr Gly Thr
65                  70                  75                  80

Gly Trp Gln Leu Asp Pro Cys Val Gly Asn Thr Gly Ser Val Pro Arg
                85                  90                  95

Phe Gly Ile Pro Asn Leu Cys Leu Gln Asp Gly Pro Leu Gly Val Arg
            100                 105                 110

Phe Ala Asp Phe Val Thr Gly Tyr Pro Ser Gly Leu Ala Thr Gly Ala
        115                 120                 125

Thr Phe Asn Lys Asp Leu Phe Leu Gln Arg Gly Gln Ala Leu Gly His
    130                 135                 140

Glu Phe Asn Ser Lys Gly Val His Ile Ala Leu Gly Pro Ala Val Gly
145                 150                 155                 160

Pro Leu Gly Val Lys Ala Arg Gly Gly Arg Asn Phe Glu Ala Phe Gly
                165                 170                 175

Ser Asp Pro Tyr Leu Gln Gly Thr Ala Ala Ala Thr Ile Lys Gly
            180                 185                 190

Leu Gln Glu Asn Asn Val Met Ala Cys Val Lys His Phe Ile Gly Asn
    195                 200                 205
```

```
Glu Gln Glu Lys Tyr Arg Gln Pro Asp Asp Ile Asn Pro Ala Thr Asn
    210                 215                 220
Gln Thr Thr Lys Glu Ala Ile Ser Ala Asn Ile Pro Asp Arg Ala Met
225                 230                 235                 240
His Ala Leu Tyr Leu Trp Pro Phe Ala Asp Ser Val Arg Ala Gly Val
            245                 250                 255
Gly Ser Val Met Cys Ser Tyr Asn Arg Val Asn Asn Thr Tyr Ala Cys
            260                 265                 270
Glu Asn Ser Tyr Met Met Asn His Leu Leu Lys Glu Glu Leu Gly Phe
            275                 280                 285
Gln Gly Phe Val Val Ser Asp Trp Gly Ala Gln Leu Ser Gly Val Tyr
290                 295                 300
Ser Ala Ile Ser Gly Leu Asp Met Ser Met Pro Gly Glu Val Tyr Gly
305                 310                 315                 320
Gly Trp Asn Thr Gly Thr Ser Phe Trp Gly Gln Asn Leu Thr Lys Ala
                325                 330                 335
Ile Tyr Asn Glu Thr Val Pro Ile Glu Arg Leu Asp Asp Met Ala Thr
                340                 345                 350
Arg Ile Leu Ala Ala Leu Tyr Ala Thr Asn Ser Phe Pro Thr Glu Asp
            355                 360                 365
His Leu Pro Asn Phe Ser Ser Trp Thr Thr Lys Glu Tyr Gly Asn Lys
            370                 375                 380
Tyr Tyr Ala Asp Asn Thr Thr Glu Ile Val Lys Val Asn Tyr Asn Val
385                 390                 395                 400
Asp Pro Ser Asn Asp Phe Thr Glu Asp Thr Ala Leu Lys Val Ala Glu
                405                 410                 415
Glu Ser Ile Val Leu Leu Lys Asn Glu Asn Asn Thr Leu Pro Ile Ser
                420                 425                 430
Pro Glu Lys Ala Lys Arg Leu Leu Leu Ser Gly Ile Ala Ala Gly Pro
            435                 440                 445
Asp Pro Ile Gly Tyr Gln Cys Glu Asp Gln Ser Cys Thr Asn Gly Ala
            450                 455                 460
Leu Phe Gln Gly Trp Gly Ser Gly Ser Val Gly Ser Pro Lys Tyr Gln
465                 470                 475                 480
Val Thr Pro Phe Glu Glu Ile Ser Tyr Leu Ala Arg Lys Asn Lys Met
                485                 490                 495
Gln Phe Asp Tyr Ile Arg Glu Ser Tyr Asp Leu Ala Gln Val Thr Lys
            500                 505                 510
Val Ala Ser Asp Ala His Leu Ser Ile Val Val Val Ser Ala Ala Ser
            515                 520                 525
Gly Glu Gly Tyr Ile Thr Val Asp Gly Asn Gln Gly Asp Arg Lys Asn
530                 535                 540
Leu Thr Leu Trp Asn Asn Gly Asp Lys Leu Ile Glu Thr Val Ala Glu
545                 550                 555                 560
Asn Cys Ala Asn Thr Val Val Val Thr Ser Thr Gly Gln Ile Asn
                565                 570                 575
Phe Glu Gly Phe Ala Asp His Pro Asn Val Thr Ala Ile Val Trp Ala
            580                 585                 590
Gly Pro Leu Gly Asp Arg Ser Gly Thr Ala Ile Ala Asn Ile Leu Phe
            595                 600                 605
Gly Lys Ala Asn Pro Ser Gly His Leu Pro Phe Thr Ile Ala Lys Thr
            610                 615                 620
```

```
Asp Asp Asp Tyr Ile Pro Ile Glu Thr Tyr Ser Pro Ser Ser Gly Glu
625                 630                 635                 640

Pro Glu Asp Asn His Leu Val Glu Asn Asp Leu Leu Val Asp Tyr Arg
            645                 650                 655

Tyr Phe Glu Glu Lys Asn Ile Glu Pro Arg Tyr Ala Phe Gly Tyr Gly
                660                 665                 670

Leu Ser Tyr Asn Glu Tyr Glu Val Ser Asn Ala Lys Val Ser Ala Ala
            675                 680                 685

Lys Lys Val Asp Glu Glu Leu Pro Glu Pro Ala Thr Tyr Leu Ser Glu
690                 695                 700

Phe Ser Tyr Gln Asn Ala Lys Asp Ser Lys Asn Pro Ser Asp Ala Phe
705                 710                 715                 720

Ala Pro Ala Asp Leu Asn Arg Val Asn Glu Tyr Leu Tyr Pro Tyr Leu
            725                 730                 735

Asp Ser Asn Val Thr Leu Lys Asp Gly Asn Tyr Glu Tyr Pro Asp Gly
            740                 745                 750

Tyr Ser Thr Glu Gln Arg Thr Pro Asn Gln Pro Gly Gly Leu
            755                 760                 765

Gly Gly Asn Asp Ala Leu Trp Glu Val Ala Tyr Asn Ser Thr Asp Lys
770                 775                 780

Phe Val Pro Gln Gly Asn Ser Thr Asp Lys Phe Val Pro Gln Leu Tyr
785                 790                 795                 800

Leu Lys His Pro Glu Asp Gly Lys Phe Glu Thr Pro Ile Gln Leu Arg
                805                 810                 815

Gly Phe Glu Lys Val Glu Leu Ser Pro Gly Lys Lys Thr Val Asp
            820                 825                 830

Leu Arg Leu Leu Arg Arg Asp Leu Ser Val Trp Asp Thr Thr Arg Gln
            835                 840                 845

Ser Trp Ile Val Glu Ser Gly Thr Tyr Glu Ala Leu Ile Gly Val Ala
            850                 855                 860

Val Asn Asp Ile Lys Thr Ser Val Leu Phe Thr Ile
865                 870                 875

<210> SEQ ID NO 18
<211> LENGTH: 477
<212> TYPE: PRT
<213> ORGANISM: Bacillus subtilis

<400> SEQUENCE: 18

Met Ile His Gln His Pro Glu Ser Phe Pro Lys His Phe Leu Trp Gly
1               5                   10                  15

Ser Ala Ser Ala Ala Tyr Gln Ile Glu Gly Ala Trp Asn Glu Asp Gly
            20                  25                  30

Lys Gly Pro Ser Val Trp Asp Val Phe Thr Lys Ile Pro Gly Lys Thr
        35                  40                  45

Phe Lys Gly Thr Asn Gly Glu Ile Ala Val Asp His Tyr His Arg Phe
    50                  55                  60

Lys Glu Asp Val Ala Leu Met Ala Glu Met Gly Leu Lys Ala Tyr Arg
65                  70                  75                  80

Phe Ser Val Ser Trp Pro Arg Val Phe Pro Lys Gly Lys Gly Glu Ile
                85                  90                  95

Asn Glu Ala Gly Leu Ala Phe Tyr Asp Ser Leu Ile Asp Glu Leu Leu
            100                 105                 110

Ser His His Ile Glu Pro Val Leu Thr Leu Tyr His Trp Asp Leu Pro
        115                 120                 125
```

Gln Ala Leu Met Asp Glu Tyr Gly Gly Phe Glu Ser Arg Asn Ile Ile
    130                 135                 140

Glu Asp Phe Asn His Tyr Cys Ile Thr Leu Tyr Lys Arg Phe Gly Asp
145                 150                 155                 160

Arg Val Lys Tyr Trp Val Thr Leu Asn Glu Gln Asn Tyr Asn Phe Asn
                165                 170                 175

His Gly Phe Ile Thr Ala Met His Pro Pro Gly Val Lys Asp Arg Lys
            180                 185                 190

Arg Phe Tyr Glu Ala Asn His Ile Ala Phe Leu Ala Asn Ala Lys Ala
        195                 200                 205

Ile Glu Ser Phe Arg Glu Tyr Val Pro Glu Gly Lys Ile Gly Pro Ser
210                 215                 220

Phe Ala Tyr Ser Pro Ala Tyr Pro Leu Ser Ser His Pro Glu Asp Ile
225                 230                 235                 240

Leu Ala Phe Glu Asn Ala Glu Glu Phe Thr Asn Asn Trp Trp Leu Asp
                245                 250                 255

Met Tyr Cys Trp Gly Thr Tyr Pro Gln Ile Pro Phe Arg Cys Leu Glu
            260                 265                 270

Lys Gln Gly Trp Ala Pro Thr Ile Glu Ala Gly Asp Met Asp Leu Leu
        275                 280                 285

Ala Lys Gly Lys Pro Asp Phe Val Gly Val Asn Tyr Tyr Gln Thr Ile
290                 295                 300

Thr Tyr Glu Arg Asn Pro Leu Asp Gly Val Ser Glu Gly Lys Met Asn
305                 310                 315                 320

Thr Thr Gly Gln Lys Gly Thr Asn Gln Glu Thr Gly Ile Pro Gly Val
                325                 330                 335

Phe Lys Thr Lys Lys Asn Pro His Leu Thr Thr Ser Asn Trp Asp Trp
            340                 345                 350

Thr Ile Asp Pro Ile Gly Leu Arg Ile Gly Leu Arg Arg Ile Thr Ser
        355                 360                 365

Arg Tyr Gln Leu Pro Val Phe Ile Thr Glu Asn Gly Leu Gly Glu Phe
370                 375                 380

Asp Lys Val Glu Asp Gly Thr Val Gln Asp Asp Tyr Arg Ile Asp Tyr
385                 390                 395                 400

Leu Arg Ser His Leu Glu Gln Cys Arg Gln Ala Ile Ser Asp Gly Val
                405                 410                 415

Asp Leu Ile Gly Tyr Cys Ser Trp Ser Phe Thr Asp Leu Leu Ser Trp
            420                 425                 430

Leu Asn Gly Tyr Gln Lys Arg Tyr Gly Phe Val Tyr Val Asn Arg Asp
        435                 440                 445

Glu Glu Ser Thr Ser Asp Leu Lys Arg Leu Lys Lys Ser Phe Tyr
450                 455                 460

Trp Tyr Gln Asp Val Ile Lys Thr Asn Gly Glu Ser Leu
465                 470                 475

<210> SEQ ID NO 19
<211> LENGTH: 880
<212> TYPE: PRT
<213> ORGANISM: Saccharomycopsis fibuligera

<400> SEQUENCE: 19

Met Leu Leu Ile Leu Glu Leu Leu Val Leu Ile Ile Gly Leu Gly Val
1               5                   10                  15

Ala Leu Pro Val Gln Thr His Asn Leu Thr Asp Asn Gln Gly Phe Asp

-continued

```
                20                  25                  30
Glu Glu Ser Ser Gln Trp Ile Ser Pro His Tyr Tyr Pro Thr Pro Gln
             35                  40                  45
Gly Gly Arg Leu Gln Gly Val Trp Gln Asp Ala Tyr Thr Lys Ala Lys
         50                  55                  60
Ala Leu Val Ser Gln Met Thr Ile Val Glu Lys Val Asn Leu Thr Thr
 65                  70                  75                  80
Gly Thr Gly Trp Gln Leu Gly Pro Cys Val Gly Asn Thr Gly Ser Val
             85                  90                  95
Pro Arg Phe Gly Ile Pro Asn Leu Cys Leu Gln Asp Gly Pro Leu Gly
            100                 105                 110
Val Arg Leu Thr Asp Phe Ser Thr Gly Tyr Pro Ser Gly Met Ala Thr
            115                 120                 125
Gly Ala Thr Phe Asn Lys Asp Leu Phe Leu Gln Arg Gly Gln Ala Leu
        130                 135                 140
Gly His Glu Phe Asn Ser Lys Gly Val His Ile Ala Leu Gly Pro Ala
145                 150                 155                 160
Val Gly Pro Leu Gly Val Lys Ala Arg Gly Gly Arg Asn Phe Glu Ala
            165                 170                 175
Phe Gly Ser Asp Pro Tyr Leu Gln Gly Ile Ala Ala Ala Thr Ile
            180                 185                 190
Lys Gly Leu Gln Glu Asn Asn Val Met Ala Cys Val Lys His Phe Ile
        195                 200                 205
Gly Asn Glu Gln Asp Ile Tyr Arg Gln Pro Ser Asn Ser Lys Val Asp
        210                 215                 220
Pro Glu Tyr Asp Pro Ala Thr Lys Glu Ser Ile Ser Ala Asn Ile Pro
225                 230                 235                 240
Asp Arg Ala Met His Glu Leu Tyr Leu Trp Pro Phe Ala Asp Ser Ile
            245                 250                 255
Arg Ala Gly Val Gly Ser Val Met Cys Ser Tyr Asn Arg Val Asn Asn
            260                 265                 270
Thr Tyr Ser Cys Glu Asn Ser Tyr Met Ile Asn His Leu Leu Lys Glu
        275                 280                 285
Glu Leu Gly Phe Gln Gly Phe Val Ser Asp Trp Ala Ala Gln Met
        290                 295                 300
Ser Gly Ala Tyr Ser Ala Ile Ser Gly Leu Asp Met Ser Met Pro Gly
305                 310                 315                 320
Glu Leu Leu Gly Gly Trp Asn Thr Gly Lys Ser Tyr Trp Gly Gln Asn
            325                 330                 335
Leu Thr Lys Ala Val Tyr Asn Glu Thr Val Pro Ile Glu Arg Leu Asp
        340                 345                 350
Asp Met Ala Thr Arg Ile Leu Ala Ala Leu Tyr Ala Thr Asn Ser Phe
        355                 360                 365
Pro Thr Lys Asp Arg Leu Pro Asn Phe Ser Ser Phe Thr Thr Lys Glu
        370                 375                 380
Tyr Gly Asn Glu Phe Phe Val Asp Lys Thr Ser Pro Val Val Lys Val
385                 390                 395                 400
Asn His Phe Val Asp Pro Ser Asn Asp Phe Thr Glu Asp Thr Ala Leu
            405                 410                 415
Lys Val Ala Glu Glu Ser Ile Val Leu Leu Asn Glu Lys Asn Thr
        420                 425                 430
Leu Pro Ile Ser Pro Asn Lys Val Arg Lys Leu Leu Leu Ser Gly Ile
        435                 440                 445
```

```
Ala Ala Gly Pro Asp Pro Lys Gly Tyr Glu Cys Ser Asp Gln Ser Cys
        450                 455                 460

Val Asp Gly Ala Leu Phe Glu Gly Trp Gly Ser Gly Ser Val Gly Tyr
465                 470                 475                 480

Pro Lys Tyr Gln Val Thr Pro Phe Glu Ile Ser Ala Asn Ala Arg
                    485                 490                 495

Lys Asn Lys Met Gln Phe Asp Tyr Ile Arg Glu Ser Phe Asp Leu Thr
                500                 505                 510

Gln Val Ser Thr Val Ala Ser Asp Ala His Met Ser Ile Val Val Val
            515                 520                 525

Ser Ala Val Ser Gly Glu Gly Tyr Leu Ile Ile Asp Gly Asn Arg Gly
        530                 535                 540

Asp Lys Asn Asn Val Thr Leu Trp His Asn Ser Asp Asn Leu Ile Lys
545                 550                 555                 560

Ala Val Ala Glu Asn Cys Ala Asn Thr Val Val Ile Thr Ser Thr
                565                 570                 575

Gly Gln Val Asp Val Glu Ser Phe Ala Asp His Pro Asn Val Thr Ala
                580                 585                 590

Ile Val Trp Ala Gly Pro Leu Gly Asp Arg Ser Gly Thr Ala Ile Ala
        595                 600                 605

Asn Ile Leu Phe Gly Asn Ala Asn Pro Ser Gly His Leu Pro Phe Thr
        610                 615                 620

Val Ala Lys Ser Asn Asp Asp Tyr Ile Pro Ile Val Thr Tyr Asn Pro
625                 630                 635                 640

Pro Asn Gly Glu Pro Glu Asp Asn Thr Leu Ala Glu His Asp Leu Leu
                645                 650                 655

Val Asp Tyr Arg Tyr Phe Glu Glu Lys Asn Ile Glu Pro Arg Tyr Ala
                660                 665                 670

Phe Gly Tyr Gly Leu Ser Tyr Asn Glu Tyr Lys Val Ser Asn Ala Lys
            675                 680                 685

Val Ser Ala Ala Lys Lys Val Asp Glu Glu Leu Pro Gln Pro Lys Leu
        690                 695                 700

Tyr Leu Ala Glu Tyr Ser Tyr Asn Lys Thr Glu Glu Ile Asn Asn Pro
705                 710                 715                 720

Glu Asp Ala Phe Phe Pro Ser Asn Ala Arg Arg Ile Gln Glu Phe Leu
                725                 730                 735

Tyr Pro Tyr Leu Asp Ser Asn Val Thr Leu Lys Asp Gly Asn Tyr Glu
                740                 745                 750

Tyr Pro Asp Gly Tyr Ser Thr Glu Gln Arg Thr Thr Pro Ile Gln Pro
            755                 760                 765

Gly Gly Gly Leu Gly Gly Asn Asp Ala Leu Trp Glu Val Ala Tyr Lys
        770                 775                 780

Val Glu Val Asp Val Gln Asn Leu Gly Asn Ser Thr Asp Lys Phe Val
785                 790                 795                 800

Pro Gln Leu Tyr Leu Lys His Pro Glu Asp Gly Lys Phe Glu Thr Pro
                805                 810                 815

Val Gln Leu Arg Gly Phe Glu Lys Val Glu Leu Ser Pro Gly Glu Lys
                820                 825                 830

Lys Thr Val Glu Phe Glu Leu Leu Arg Arg Asp Leu Ser Val Trp Asp
            835                 840                 845

Thr Thr Arg Gln Ser Trp Ile Val Glu Ser Gly Thr Tyr Glu Ala Leu
        850                 855                 860
```

```
Ile Gly Val Ala Val Asn Asp Ile Lys Thr Ser Val Leu Phe Thr Ile
865                 870                 875                 880

<210> SEQ ID NO 20
<211> LENGTH: 63
<212> TYPE: PRT
<213> ORGANISM: Aspergillus wentii

<400> SEQUENCE: 20

Ala Glx Leu Gly Phe Glx Gly Phe Val Met Ser Asp Trp Ala Ala His
1               5                   10                  15

His Ala Gly Val Ser Gly Ala Leu Ala Gly Leu Asx Met Gly Ser Met
            20                  25                  30

Pro Gly Asx Val Asx Tyr Asx Ser Gly Thr Ser Tyr Trp Gly Thr Asn
        35                  40                  45

Leu Thr Ile Ser Leu Trp Val Asn Gly Thr Val Pro Glx Trp Arg
    50                  55                  60

<210> SEQ ID NO 21
<211> LENGTH: 450
<212> TYPE: PRT
<213> ORGANISM: Bacillus circulans

<400> SEQUENCE: 21

Met Ser Ile His Met Phe Pro Ser Asp Phe Lys Trp Gly Val Ala Thr
1               5                   10                  15

Ala Ala Tyr Gln Ile Glu Gly Ala Tyr Asn Glu Asp Gly Arg Gly Met
            20                  25                  30

Ser Ile Trp Asp Thr Phe Ala His Thr Pro Gly Lys Val Lys Asn Gly
        35                  40                  45

Asp Asn Gly Asn Val Ala Cys Asp Ser Tyr His Arg Val Glu Glu Asp
    50                  55                  60

Val Gln Leu Leu Lys Asp Leu Gly Val Lys Val Tyr Arg Phe Ser Ile
65                  70                  75                  80

Ser Trp Pro Arg Val Leu Pro Gln Gly Thr Gly Glu Val Asn Arg Ala
            85                  90                  95

Gly Leu Asp Tyr Tyr His Arg Leu Val Asp Glu Leu Leu Ala Asn Gly
        100                 105                 110

Ile Glu Pro Phe Cys Thr Leu Tyr His Trp Asp Leu Pro Gln Ala Leu
    115                 120                 125

Gln Asp Gln Gly Gly Trp Gly Ser Arg Ile Thr Ile Asp Ala Phe Ala
130                 135                 140

Glu Tyr Ala Glu Leu Met Phe Lys Glu Leu Gly Gly Lys Ile Lys Gln
145                 150                 155                 160

Trp Ile Thr Phe Asn Glu Pro Trp Cys Met Ala Phe Leu Ser Asn Tyr
            165                 170                 175

Leu Gly Val His Ala Pro Gly Asn Lys Asp Leu Gln Leu Ala Ile Asp
        180                 185                 190

Val Ser His His Leu Leu Val Ala His Gly Arg Ala Val Thr Leu Phe
    195                 200                 205

Arg Glu Leu Gly Ile Ser Gly Glu Ile Gly Ile Ala Pro Asn Thr Ser
210                 215                 220

Trp Ala Val Pro Tyr Arg Arg Thr Lys Glu Asp Met Glu Ala Cys Leu
225                 230                 235                 240

Arg Val Asn Gly Trp Ser Gly Asp Trp Tyr Leu Asp Pro Ile Tyr Phe
            245                 250                 255
```

```
Gly Glu Tyr Pro Lys Phe Met Leu Asp Trp Tyr Asn Leu Gly Tyr
            260                 265                 270

Lys Pro Pro Ile Val Asp Gly Asp Met Glu Leu Ile His Gln Pro Ile
            275                 280                 285

Asp Phe Ile Gly Ile Asn Tyr Tyr Thr Ser Ser Met Asn Arg Tyr Asn
        290                 295                 300

Pro Gly Glu Ala Gly Gly Met Leu Ser Ser Glu Ala Ile Ser Met Gly
305                 310                 315                 320

Ala Pro Lys Thr Asp Ile Gly Trp Glu Ile Tyr Ala Glu Gly Leu Tyr
                325                 330                 335

Asp Leu Leu Arg Tyr Thr Ala Asp Lys Tyr Gly Asn Pro Thr Leu Tyr
            340                 345                 350

Ile Thr Glu Asn Gly Ala Cys Tyr Asn Asp Gly Leu Ser Leu Asp Gly
        355                 360                 365

Arg Ile His Asp Gln Arg Arg Ile Asp Tyr Leu Ala Met His Leu Ile
    370                 375                 380

Gln Ala Ser Arg Ala Ile Glu Asp Gly Ile Asn Leu Lys Gly Tyr Met
385                 390                 395                 400

Glu Trp Ser Leu Met Asp Asn Phe Glu Trp Ala Glu Gly Tyr Gly Met
                405                 410                 415

Arg Phe Gly Leu Val His Val Asp Tyr Asp Thr Leu Val Arg Thr Pro
            420                 425                 430

Lys Asp Ser Phe Tyr Trp Tyr Lys Gly Val Ile Ser Arg Gly Trp Leu
        435                 440                 445

Asp Leu
    450

<210> SEQ ID NO 22
<211> LENGTH: 448
<212> TYPE: PRT
<213> ORGANISM: Clostridium thermocellum

<400> SEQUENCE: 22

Met Ser Lys Ile Thr Phe Pro Lys Asp Phe Ile Trp Gly Ser Ala Thr
1               5                   10                  15

Ala Ala Tyr Gln Ile Glu Gly Ala Tyr Asn Glu Asp Gly Lys Gly Glu
            20                  25                  30

Ser Ile Trp Asp Arg Phe Ser His Thr Pro Gly Asn Ile Ala Asp Gly
        35                  40                  45

His Thr Gly Asp Val Ala Cys Asp His Tyr His Arg Tyr Glu Glu Asp
    50                  55                  60

Ile Lys Ile Met Lys Glu Ile Gly Ile Lys Ser Tyr Arg Phe Ser Ile
65                  70                  75                  80

Ser Trp Pro Arg Ile Phe Pro Glu Gly Thr Gly Lys Leu Asn Gln Lys
                85                  90                  95

Gly Leu Asp Phe Tyr Lys Arg Leu Thr Asn Leu Leu Leu Glu Asn Gly
            100                 105                 110

Ile Met Pro Ala Ile Thr Leu Tyr His Trp Asp Leu Pro Gln Lys Leu
        115                 120                 125

Gln Asp Lys Gly Gly Trp Lys Asn Arg Asp Thr Thr Asp Tyr Phe Thr
    130                 135                 140

Glu Tyr Ser Glu Val Ile Phe Lys Asn Leu Gly Asp Ile Val Pro Ile
145                 150                 155                 160

Trp Phe Thr His Asn Glu Pro Gly Val Val Ser Leu Leu Gly His Phe
                165                 170                 175
```

Leu Gly Ile His Ala Pro Gly Ile Lys Asp Leu Arg Thr Ser Leu Glu
            180                 185                 190

Val Ser His Asn Leu Leu Ser His Gly Lys Ala Val Lys Leu Phe
        195                 200                 205

Arg Glu Met Asn Ile Asp Ala Gln Ile Gly Ile Ala Leu Asn Leu Ser
210                 215                 220

Tyr His Tyr Pro Ala Ser Glu Lys Ala Glu Asp Ile Glu Ala Ala Glu
225                 230                 235                 240

Leu Ser Phe Ser Leu Ala Gly Arg Trp Tyr Leu Asp Pro Val Leu Lys
                245                 250                 255

Gly Arg Tyr Pro Glu Asn Ala Leu Lys Leu Tyr Lys Lys Gly Ile
            260                 265                 270

Glu Leu Ser Phe Pro Glu Asp Leu Lys Leu Ile Ser Gln Pro Ile
        275                 280                 285

Asp Phe Ile Ala Phe Asn Asn Tyr Ser Ser Glu Phe Ile Lys Tyr Asp
290                 295                 300

Pro Ser Ser Glu Ser Gly Phe Ser Pro Ala Asn Ser Ile Leu Glu Lys
305                 310                 315                 320

Phe Glu Lys Thr Asp Met Gly Trp Ile Ile Tyr Pro Glu Gly Leu Tyr
                325                 330                 335

Asp Leu Leu Met Leu Leu Asp Arg Asp Tyr Gly Lys Pro Asn Ile Val
            340                 345                 350

Ile Ser Glu Asn Gly Ala Ala Phe Lys Asp Glu Ile Gly Ser Asn Gly
        355                 360                 365

Lys Ile Glu Asp Thr Lys Arg Ile Gln Tyr Leu Lys Asp Tyr Leu Thr
370                 375                 380

Gln Ala His Arg Ala Ile Gln Asp Gly Val Asn Leu Lys Ala Tyr Tyr
385                 390                 395                 400

Leu Trp Ser Leu Leu Asp Asn Phe Glu Trp Ala Tyr Gly Tyr Asn Lys
                405                 410                 415

Arg Phe Gly Ile Val His Val Asn Phe Asp Thr Leu Glu Arg Lys Ile
            420                 425                 430

Lys Asp Ser Gly Tyr Trp Tyr Lys Glu Val Ile Lys Asn Asn Gly Phe
        435                 440                 445

<210> SEQ ID NO 23
<211> LENGTH: 480
<212> TYPE: PRT
<213> ORGANISM: Enterobacter agglomerans

<400> SEQUENCE: 23

Met Lys Asn Gly Met Leu Ala Leu Gly Met Thr Ala Ala Asp Val Pro
1               5                   10                  15

Asp Asn Phe Leu Trp Gly Ala Ala Ser Ala Ala Tyr Gln Val Glu Gly
            20                  25                  30

Ala Thr Asn Lys Asp Gly Lys Gly Arg Ser Val Trp Asp Tyr Tyr Leu
        35                  40                  45

Asp Glu Lys His Leu Ala Gly Pro Gly Ile Ser Gly Ala Leu Arg Leu
50                  55                  60

Thr Phe Thr Asp Arg Asp Gln Tyr Leu Lys Asp Ile Gln Leu Phe Lys
65                  70                  75                  80

Glu Leu Gly Leu Asn Ser Tyr Arg Phe Ser His Arg Leu Asp Thr Tyr
                85                  90                  95

Tyr Pro Asp Gly Gln Gly Pro Val Asn Leu Arg Ala Val Ala His Tyr

```
                  100                 105                 110
Arg Gln Phe Ile Thr Asp Leu Glu Ala Ala Gly Ile Lys Pro Leu Val
            115                 120                 125

Thr Leu Tyr His Trp Asp Met Pro Glu Ser Leu Ser Ala Ala Gly Gly
        130                 135                 140

Trp Glu Asn Arg Glu Ser Val Glu Trp Phe Gln Arg Tyr Ala Glu Val
145                 150                 155                 160

Ile Phe Ala Asn Phe Ser Asp Gln Val Asp Gln Phe Val Leu Ile Asn
                165                 170                 175

Glu Pro Thr Val Glu Val Ala Thr Lys Ile Met Ala Glu Lys Arg Leu
            180                 185                 190

Lys Gly Glu Glu Leu Thr Leu Pro Pro Ile Val Pro Ala Gly Ser Tyr
        195                 200                 205

Leu Glu Thr Ser Leu Lys Ser Tyr Asn His Ile Leu Leu Ala Ser Ala
        210                 215                 220

Ala Ala Ala Glu Ser Phe Lys Val Lys Gly Tyr Lys Gly Arg Leu Gly
225                 230                 235                 240

Ile Ala Leu Pro Phe Phe Pro Val Leu Thr Thr Glu Asn Ala Ser Asp
                245                 250                 255

Glu Asp Lys Ala Asp Ala Arg Leu Val Asp Gly Ile Leu Asn Arg Trp
            260                 265                 270

Phe Leu Asp Ala Met Tyr Lys Gly Asn Tyr Pro Ala Asp Val Leu Lys
        275                 280                 285

Leu Ala Ala Asp Arg His Leu Asn Ile Asp Val Gln Pro Gly Asp Ala
        290                 295                 300

Glu Arg Ile His Asp Ala Gly Leu Gly Phe Leu Gly Ile Asn Tyr Tyr
305                 310                 315                 320

Ala Pro Phe Phe Ile Arg His Gln Lys Asn Ala Ser Glu Val Tyr Ser
                325                 330                 335

Pro Glu Ile Ile Phe Pro Lys Asn Glu Lys Leu Ala Phe Asn Gly Ala
            340                 345                 350

Val Arg Pro Asp Gln Phe Ser Ala Leu Leu Glu Arg Val Arg Asp Glu
        355                 360                 365

Tyr Gly Asn Pro Pro Val Ile Ile Thr Glu Asn Gly Ala Gly Phe Glu
        370                 375                 380

Gly Glu Asp Gln Leu Thr Asn Gly Lys Val Asn Asp Val Asn Arg Cys
385                 390                 395                 400

Leu Tyr Leu Val Asp His Ile His Ala Met Arg Glu Ser Ile Ala Arg
                405                 410                 415

Gly Ala Asn Val Gln Gly Tyr Tyr Val Trp Ser Ser His Asp Asn Leu
            420                 425                 430

Glu Trp Leu Ser Gly Tyr Lys Ser Arg Phe Gly Met Ile Tyr Val Asp
        435                 440                 445

Tyr Asp Thr Gln Lys Arg Thr Pro Lys Leu Ser Ala Glu Ile Tyr Gly
        450                 455                 460

Lys Ile Ile Arg Gly Glu Asn Ile Ser Asp Val Asp Cys Lys Ser Asp
465                 470                 475                 480
```

<210> SEQ ID NO 24
<211> LENGTH: 448
<212> TYPE: PRT
<213> ORGANISM: Paenibacillus polymyxa

<400> SEQUENCE: 24

-continued

```
Met Thr Ile Phe Gln Phe Pro Gln Asp Phe Met Trp Gly Thr Ala Thr
1               5                   10                  15
Ala Ala Tyr Gln Ile Glu Gly Ala Tyr Gln Glu Asp Gly Arg Gly Leu
            20                  25                  30
Ser Ile Trp Asp Thr Phe Ala His Thr Pro Gly Lys Val Phe Asn Gly
        35                  40                  45
Asp Asn Gly Asn Val Ala Cys Asp Ser Tyr His Arg Tyr Glu Glu Asp
    50                  55                  60
Ile Arg Leu Met Lys Glu Leu Gly Ile Arg Thr Tyr Arg Phe Ser Val
65                  70                  75                  80
Ser Trp Pro Arg Ile Phe Pro Asn Gly Asp Gly Glu Val Asn Gln Glu
                85                  90                  95
Gly Leu Asp Tyr Tyr His Arg Val Val Asp Leu Leu Asn Asp Asn Gly
            100                 105                 110
Ile Glu Pro Phe Cys Thr Leu Tyr His Trp Asp Leu Pro Gln Ala Leu
        115                 120                 125
Gln Asp Ala Gly Gly Trp Gly Asn Arg Arg Thr Ile Gln Ala Phe Val
    130                 135                 140
Gln Phe Ala Glu Thr Met Phe Arg Glu Phe His Gly Lys Ile Gln His
145                 150                 155                 160
Trp Leu Thr Phe Asn Glu Pro Trp Cys Ile Ala Phe Leu Ser Asn Met
                165                 170                 175
Leu Gly Val His Ala Pro Gly Leu Thr Asn Leu Gln Thr Ala Ile Asp
            180                 185                 190
Val Gly His His Leu Leu Val Ala His Gly Leu Ser Val Arg Arg Phe
        195                 200                 205
Arg Glu Leu Gly Thr Ser Gly Gln Ile Gly Ile Ala Pro Asn Val Ser
    210                 215                 220
Trp Ala Val Pro Tyr Ser Thr Ser Glu Glu Asp Lys Ala Ala Cys Ala
225                 230                 235                 240
Arg Thr Ile Ser Leu His Ser Asp Trp Phe Leu Gln Pro Ile Tyr Gln
                245                 250                 255
Gly Ser Tyr Pro Gln Phe Leu Val Asp Trp Phe Ala Glu Gln Gly Ala
            260                 265                 270
Thr Val Pro Ile Gln Asp Gly Asp Met Asp Ile Ile Gly Glu Pro Ile
        275                 280                 285
Asp Met Ile Gly Ile Asn Tyr Tyr Ser Met Ser Val Asn Arg Phe Asn
    290                 295                 300
Pro Glu Ala Gly Phe Leu Gln Ser Glu Glu Ile Asn Met Gly Leu Pro
305                 310                 315                 320
Val Thr Asp Ile Gly Trp Pro Val Glu Ser Arg Gly Leu Tyr Glu Val
                325                 330                 335
Leu His Tyr Leu Gln Lys Tyr Gly Asn Ile Asp Ile Tyr Ile Thr Glu
            340                 345                 350
Asn Gly Ala Cys Ile Asn Asp Glu Val Val Asn Gly Lys Val Gln Asp
        355                 360                 365
Asp Arg Arg Ile Ser Tyr Met Gln Gln His Leu Val Gln Val His Arg
    370                 375                 380
Thr Ile His Asp Gly Leu His Val Lys Gly Tyr Met Ala Trp Ser Leu
385                 390                 395                 400
Leu Asp Asn Phe Glu Trp Ala Glu Gly Tyr Asn Met Arg Phe Gly Met
                405                 410                 415
Ile His Val Asp Phe Arg Thr Gln Val Arg Thr Pro Lys Glu Ser Tyr
```

```
                420              425              430
Tyr Trp Tyr Arg Asn Val Val Ser Asn Asn Trp Leu Glu Thr Arg Arg
        435              440              445

<210> SEQ ID NO 25
<211> LENGTH: 446
<212> TYPE: PRT
<213> ORGANISM: Thermotoga maritima

<400> SEQUENCE: 25

Met Asn Val Lys Lys Phe Pro Glu Gly Phe Leu Trp Gly Val Ala Thr
1               5                   10                  15

Ala Ser Tyr Gln Ile Glu Gly Ser Pro Leu Ala Asp Gly Ala Gly Met
            20                  25                  30

Ser Ile Trp His Thr Phe Ser His Thr Pro Gly Asn Val Lys Asn Gly
        35                  40                  45

Asp Thr Gly Asp Val Ala Cys Asp His Tyr Asn Arg Trp Lys Glu Asp
    50                  55                  60

Ile Glu Ile Ile Glu Lys Leu Gly Val Lys Ala Tyr Arg Phe Ser Ile
65                  70                  75                  80

Ser Trp Pro Arg Ile Leu Pro Glu Gly Thr Gly Arg Val Asn Gln Lys
                85                  90                  95

Gly Leu Asp Phe Tyr Asn Arg Ile Ile Asp Thr Leu Leu Glu Lys Gly
            100                 105                 110

Ile Thr Pro Phe Val Thr Ile Tyr His Trp Asp Leu Pro Phe Ala Leu
        115                 120                 125

Gln Leu Lys Gly Gly Trp Ala Asn Arg Glu Ile Ala Asp Trp Phe Ala
    130                 135                 140

Glu Tyr Ser Arg Val Leu Phe Glu Asn Phe Gly Asp Arg Val Lys Asn
145                 150                 155                 160

Trp Ile Thr Leu Asn Glu Pro Trp Val Val Ala Ile Val Gly His Leu
                165                 170                 175

Tyr Gly Val His Ala Pro Gly Met Arg Asp Ile Tyr Val Ala Phe Arg
            180                 185                 190

Ala Val His Asn Leu Leu Arg Ala His Ala Arg Ala Val Lys Val Phe
        195                 200                 205

Arg Glu Thr Val Lys Asp Gly Lys Ile Gly Ile Val Phe Asn Asn Gly
    210                 215                 220

Tyr Phe Glu Pro Ala Ser Glu Lys Glu Glu Asp Ile Arg Ala Val Arg
225                 230                 235                 240

Phe Met His Gln Phe Asn Asn Tyr Pro Leu Phe Leu Asn Pro Ile Tyr
                245                 250                 255

Arg Gly Asp Tyr Pro Glu Leu Val Leu Glu Phe Ala Arg Glu Tyr Leu
            260                 265                 270

Pro Glu Asn Tyr Lys Asp Asp Met Ser Glu Ile Gln Glu Lys Ile Asp
        275                 280                 285

Phe Val Gly Leu Asn Tyr Tyr Ser Gly His Leu Val Lys Phe Asp Pro
    290                 295                 300

Asp Ala Pro Ala Lys Val Ser Phe Val Glu Arg Asp Leu Pro Lys Thr
305                 310                 315                 320

Ala Met Gly Trp Glu Ile Val Pro Glu Gly Ile Tyr Trp Ile Leu Lys
                325                 330                 335

Lys Val Lys Glu Glu Tyr Asn Pro Pro Glu Val Tyr Ile Thr Glu Asn
            340                 345                 350
```

```
Gly Ala Ala Phe Asp Asp Val Val Ser Glu Asp Gly Arg Val His Asp
            355                 360                 365

Gln Asn Arg Ile Asp Tyr Leu Lys Ala His Ile Gly Gln Ala Trp Lys
370                 375                 380

Ala Ile Gln Glu Gly Val Pro Leu Lys Gly Tyr Phe Val Trp Ser Leu
385                 390                 395                 400

Leu Asp Asn Phe Glu Trp Ala Glu Gly Tyr Ser Lys Arg Phe Gly Ile
                405                 410                 415

Val Tyr Val Asp Tyr Ser Thr Gln Lys Arg Ile Val Lys Asp Ser Gly
            420                 425                 430

Tyr Trp Tyr Ser Asn Val Val Lys Asn Asn Gly Leu Glu Asp
        435                 440                 445

<210> SEQ ID NO 26
<211> LENGTH: 444
<212> TYPE: PRT
<213> ORGANISM: Thermotoga neapolitana

<400> SEQUENCE: 26

Met Lys Lys Phe Pro Glu Gly Phe Leu Trp Gly Val Ala Thr Ala Ser
1               5                   10                  15

Tyr Gln Ile Glu Gly Ser Pro Leu Ala Asp Gly Ala Gly Met Ser Ile
            20                  25                  30

Trp His Thr Phe Ser His Thr Pro Gly Asn Val Lys Asn Gly Asp Thr
        35                  40                  45

Gly Asp Val Ala Cys Asp His Tyr Asn Arg Trp Lys Glu Asp Ile Glu
    50                  55                  60

Ile Ile Glu Lys Ile Gly Ala Lys Ala Tyr Arg Phe Ser Ile Ser Trp
65                  70                  75                  80

Pro Arg Ile Leu Pro Glu Gly Thr Gly Lys Val Asn Gln Lys Gly Leu
                85                  90                  95

Asp Phe Tyr Asn Arg Ile Ile Asp Thr Leu Leu Glu Lys Asn Ile Thr
            100                 105                 110

Pro Phe Ile Thr Ile Tyr His Trp Asp Leu Pro Phe Ser Leu Gln Leu
        115                 120                 125

Lys Gly Gly Trp Ala Asn Arg Asp Ile Ala Asp Trp Phe Ala Glu Tyr
130                 135                 140

Ser Arg Val Leu Phe Glu Asn Phe Gly Asp Arg Val Lys His Trp Ile
145                 150                 155                 160

Thr Leu Asn Glu Pro Trp Val Val Ala Ile Val Gly His Leu Tyr Gly
                165                 170                 175

Val His Ala Pro Gly Met Lys Asp Ile Tyr Val Ala Phe His Thr Val
            180                 185                 190

His Asn Leu Leu Arg Ala His Ala Lys Ser Val Lys Val Phe Arg Glu
        195                 200                 205

Thr Val Lys Asp Gly Lys Ile Gly Ile Val Phe Asn Asn Gly Tyr Phe
210                 215                 220

Glu Pro Ala Ser Glu Arg Glu Glu Asp Ile Arg Ala Ala Arg Phe Met
225                 230                 235                 240

His Gln Phe Asn Asn Tyr Pro Leu Phe Leu Asn Pro Ile Tyr Arg Gly
                245                 250                 255

Glu Tyr Pro Asp Leu Val Leu Glu Phe Ala Arg Glu Tyr Leu Pro Arg
            260                 265                 270

Asn Tyr Glu Asp Asp Met Glu Gly Ile Lys Gln Glu Ile Asp Phe Val
        275                 280                 285
```

```
Gly Leu Asn Tyr Tyr Ser Gly His Met Val Lys Tyr Asp Pro Asn Ser
            290                 295                 300
Pro Ala Arg Val Ser Phe Val Glu Arg Asn Leu Pro Lys Thr Ala Met
305                 310                 315                 320
Gly Trp Glu Ile Val Pro Glu Gly Ile Tyr Trp Ile Leu Lys Gly Val
                325                 330                 335
Lys Glu Glu Tyr Asn Pro Gln Glu Val Tyr Ile Thr Glu Asn Gly Ala
            340                 345                 350
Ala Phe Asp Asp Val Val Ser Glu Gly Lys Val His Asp Gln Asn
        355                 360                 365
Arg Ile Asp Tyr Leu Arg Ala His Ile Glu Gln Val Trp Arg Ala Ile
370                 375                 380
Gln Asp Gly Val Pro Leu Lys Gly Tyr Phe Val Trp Ser Leu Leu Asp
385                 390                 395                 400
Asn Phe Glu Trp Ala Glu Gly Tyr Ser Lys Arg Phe Gly Ile Val Tyr
                405                 410                 415
Val Asp Tyr Asn Thr Gln Lys Arg Ile Ile Lys Asp Ser Gly Tyr Trp
            420                 425                 430
Tyr Ser Asn Gly Ile Lys Asn Asn Gly Leu Thr Asp
        435                 440
```

<210> SEQ ID NO 27
<211> LENGTH: 755
<212> TYPE: PRT
<213> ORGANISM: Clostridium thermocellum

<400> SEQUENCE: 27

```
Met Ala Val Asp Ile Lys Lys Ile Ile Lys Gln Met Thr Leu Glu Glu
1               5                   10                  15
Lys Ala Gly Leu Cys Ser Gly Leu Asp Phe Trp His Thr Lys Pro Val
            20                  25                  30
Glu Arg Leu Gly Ile Pro Ser Ile Met Met Thr Asp Gly Pro His Gly
        35                  40                  45
Leu Arg Lys Gln Arg Glu Asp Ala Glu Ile Ala Asp Ile Asn Asn Ser
    50                  55                  60
Val Pro Ala Thr Cys Phe Pro Ser Ala Ala Gly Leu Ala Cys Ser Trp
65                  70                  75                  80
Asp Arg Glu Leu Val Glu Arg Val Gly Ala Ala Leu Gly Glu Glu Cys
                85                  90                  95
Gln Ala Glu Asn Val Ser Ile Leu Leu Gly Pro Gly Ala Asn Ile Lys
            100                 105                 110
Arg Ser Pro Leu Cys Gly Arg Asn Phe Glu Tyr Phe Ser Glu Asp Pro
        115                 120                 125
Tyr Leu Ser Ser Glu Leu Ala Ala Ser His Ile Lys Gly Val Gln Ser
    130                 135                 140
Gln Gly Val Gly Ala Cys Leu Lys His Phe Ala Ala Asn Asn Gln Glu
145                 150                 155                 160
His Arg Arg Met Thr Val Asp Thr Ile Val Asp Glu Arg Thr Leu Arg
                165                 170                 175
Glu Ile Tyr Phe Ala Ser Phe Glu Asn Ala Val Lys Lys Ala Arg Pro
            180                 185                 190
Trp Val Val Met Cys Ala Tyr Asn Lys Leu Asn Gly Glu Tyr Cys Ser
        195                 200                 205
Glu Asn Arg Tyr Leu Leu Thr Glu Val Leu Lys Asn Glu Trp Met His
```

-continued

```
                210                 215                 220
Asp Gly Phe Val Val Ser Asp Trp Gly Ala Val Asn Asp Arg Val Ser
225                 230                 235                 240

Gly Leu Asp Ala Gly Leu Asp Leu Glu Met Pro Thr Ser His Gly Ile
                245                 250                 255

Thr Asp Lys Lys Ile Val Glu Ala Val Lys Ser Gly Lys Leu Ser Glu
                260                 265                 270

Asn Ile Leu Asn Arg Ala Val Glu Arg Ile Leu Lys Val Ile Phe Met
            275                 280                 285

Ala Leu Glu Asn Lys Lys Glu Asn Ala Gln Tyr Asp Lys Asp Ala His
        290                 295                 300

His Arg Leu Ala Arg Gln Ala Ala Ala Glu Ser Met Val Leu Leu Lys
305                 310                 315                 320

Asn Glu Asp Asp Val Leu Pro Leu Lys Lys Ser Gly Thr Ile Ala Leu
                325                 330                 335

Ile Gly Ala Phe Val Lys Lys Pro Arg Tyr Gln Gly Ser Gly Ser Ser
                340                 345                 350

His Ile Thr Pro Thr Arg Leu Asp Asp Ile Tyr Glu Glu Ile Lys Lys
            355                 360                 365

Ala Gly Gly Asp Lys Val Asn Leu Val Tyr Ser Glu Gly Tyr Arg Leu
        370                 375                 380

Glu Asn Asp Gly Ile Asp Glu Glu Leu Ile Asn Glu Ala Lys Lys Ala
385                 390                 395                 400

Ala Ser Ser Ser Asp Val Ala Val Phe Ala Gly Leu Pro Asp Glu
                405                 410                 415

Tyr Glu Ser Glu Gly Phe Asp Arg Thr His Met Ser Ile Pro Glu Asn
                420                 425                 430

Gln Asn Arg Leu Ile Glu Ala Val Ala Glu Val Gln Ser Asn Ile Val
            435                 440                 445

Val Val Leu Leu Asn Gly Ser Pro Val Glu Met Pro Trp Ile Asp Lys
        450                 455                 460

Val Lys Ser Val Leu Glu Ala Tyr Leu Gly Gly Gln Ala Leu Gly Gly
465                 470                 475                 480

Ala Leu Ala Asp Val Leu Phe Gly Glu Val Asn Pro Ser Gly Lys Leu
                485                 490                 495

Ala Glu Thr Phe Pro Val Lys Leu Ser His Asn Pro Ser Tyr Leu Asn
                500                 505                 510

Phe Pro Gly Glu Asp Asp Arg Val Glu Tyr Lys Glu Gly Leu Phe Val
            515                 520                 525

Gly Tyr Arg Tyr Tyr Asp Thr Lys Gly Ile Glu Pro Leu Phe Pro Phe
        530                 535                 540

Gly His Gly Leu Ser Tyr Thr Lys Phe Glu Tyr Ser Asp Ile Ser Val
545                 550                 555                 560

Asp Lys Lys Asp Val Ser Asp Asn Ser Ile Ile Asn Val Ser Val Lys
                565                 570                 575

Val Lys Asn Val Gly Lys Met Ala Gly Lys Glu Ile Val Gln Leu Tyr
                580                 585                 590

Val Lys Asp Val Lys Ser Ser Val Arg Arg Pro Glu Lys Glu Leu Lys
            595                 600                 605

Gly Phe Glu Lys Val Phe Leu Asn Pro Gly Glu Glu Lys Thr Val Thr
        610                 615                 620

Phe Thr Leu Asp Lys Arg Ala Phe Ala Tyr Tyr Asn Thr Gln Ile Lys
625                 630                 635                 640
```

```
Asp Trp His Val Glu Ser Gly Glu Phe Leu Ile Leu Ile Gly Arg Ser
            645                 650                 655

Ser Arg Asp Ile Val Leu Lys Glu Ser Val Arg Val Asn Ser Thr Val
            660                 665                 670

Lys Ile Arg Lys Arg Phe Thr Val Asn Ser Ala Val Glu Asp Val Met
            675                 680                 685

Ser Asp Ser Ser Ala Ala Val Leu Gly Pro Val Leu Lys Glu Ile
            690                 695                 700

Thr Asp Ala Leu Gln Ile Asp Met Asp Asn Ala His Asp Met Met Ala
705                 710                 715                 720

Ala Asn Ile Lys Asn Met Pro Leu Arg Ser Leu Val Gly Tyr Ser Gln
            725                 730                 735

Gly Arg Leu Ser Glu Glu Met Leu Glu Glu Leu Val Asp Lys Ile Asn
            740                 745                 750

Asn Val Glu
        755

<210> SEQ ID NO 28
<211> LENGTH: 473
<212> TYPE: PRT
<213> ORGANISM: Microbispora bispora

<400> SEQUENCE: 28

Met Thr Glu Ser Ala Met Thr Ser Arg Ala Gly Arg Gly Arg Gly Ala
1               5                   10                  15

Asp Leu Val Ala Ala Val Val Gln Gly His Ala Ala Ser Asp Ala
            20                  25                  30

Ala Gly Asp Leu Ser Phe Pro Asp Gly Phe Ile Trp Gly Ala Ala Thr
            35                  40                  45

Ala Ala Tyr Gln Ile Glu Gly Ala Trp Arg Glu Asp Gly Arg Gly Leu
        50                  55                  60

Trp Asp Val Phe Ser His Thr Pro Gly Lys Val Ala Ser Gly His Thr
65                  70                  75                  80

Gly Asp Ile Ala Cys Asp His Tyr His Arg Tyr Ala Asp Asp Val Arg
                85                  90                  95

Leu Met Ala Gly Leu Gly Asp Arg Val Tyr Arg Phe Ser Val Ala Trp
            100                 105                 110

Pro Arg Ile Val Pro Asp Gly Ser Gly Pro Val Asn Pro Ala Gly Leu
            115                 120                 125

Asp Phe Tyr Asp Arg Leu Val Asp Glu Leu Leu Gly His Gly Ile Thr
            130                 135                 140

Pro Tyr Pro Thr Leu Tyr His Trp Asp Leu Pro Gln Thr Leu Glu Asp
145                 150                 155                 160

Arg Gly Gly Trp Ala Ala Arg Asp Thr Ala Tyr Arg Phe Ala Glu Tyr
            165                 170                 175

Ala Leu Ala Val His Arg Arg Leu Gly Asp Arg Val Arg Cys Trp Ile
            180                 185                 190

Thr Leu Asn Glu Pro Trp Val Ala Phe Leu Ala Thr His Arg Gly
            195                 200                 205

Ala Pro Gly Ala Ala Asp Val Pro Arg Phe Arg Ala Val His His Leu
            210                 215                 220

Leu Leu Gly His Gly Leu Gly Leu Arg Leu Arg Ser Ala Gly Ala Gly
225                 230                 235                 240

Gln Leu Gly Leu Thr Leu Ser Leu Ser Pro Val Ile Glu Ala Arg Pro
```

```
            245                 250                 255
Gly Val Arg Gly Gly Arg Val Asp Ala Leu Ala Asn Arg Gln
            260                 265                 270

Phe Leu Asp Pro Ala Leu Arg Gly Arg Tyr Pro Glu Glu Val Leu Lys
            275                 280                 285

Ile Met Ala Gly His Ala Arg Leu Gly His Pro Gly Arg Asp Leu Glu
            290                 295                 300

Thr Ile His Gln Pro Val Asp Leu Leu Gly Val Asn Tyr Tyr Ser His
305                 310                 315                 320

Val Arg Leu Ala Ala Glu Gly Glu Pro Ala Asn Arg Leu Pro Gly Ser
                325                 330                 335

Glu Gly Ile Arg Phe Glu Arg Pro Thr Ala Val Thr Ala Trp Pro Gly
                340                 345                 350

Asp Arg Pro Asp Gly Leu Arg Thr Leu Leu Arg Leu Ser Arg Asp
                355                 360                 365

Tyr Pro Gly Val Gly Leu Ile Ile Thr Glu Asn Gly Ala Ala Phe Asp
                370                 375                 380

Asp Arg Ala Asp Gly Asp Arg Val His Asp Pro Glu Arg Ile Arg Tyr
385                 390                 395                 400

Leu Thr Ala Thr Leu Arg Ala Val His Asp Ala Ile Met Ala Gly Ala
                405                 410                 415

Asp Leu Arg Gly Tyr Phe Val Trp Ser Val Leu Asp Asn Phe Glu Trp
                420                 425                 430

Ala Tyr Gly Tyr His Lys Arg Gly Ile Val Tyr Val Asp Tyr Thr Thr
                435                 440                 445

Met Arg Arg Ile Pro Arg Glu Ser Ala Leu Trp Tyr Arg Asp Val Val
                450                 455                 460

Arg Arg Asn Gly Leu Arg Asn Gly Glu
465                 470

<210> SEQ ID NO 29
<211> LENGTH: 448
<212> TYPE: PRT
<213> ORGANISM: Paenibacillus polymyxa

<400> SEQUENCE: 29

Met Ser Glu Asn Thr Phe Ile Phe Pro Ala Thr Phe Met Trp Gly Thr
1               5                   10                  15

Ser Thr Ser Ser Tyr Gln Ile Glu Gly Gly Thr Asp Glu Gly Gly Arg
                20                  25                  30

Thr Pro Ser Ile Trp Asp Thr Phe Cys Gln Ile Pro Gly Lys Val Ile
            35                  40                  45

Gly Gly Asp Cys Gly Asp Val Ala Cys Asp His Phe His His Phe Lys
        50                  55                  60

Glu Asp Val Gln Leu Met Lys Gln Leu Gly Phe Leu His Tyr Arg Phe
65                  70                  75                  80

Ser Val Ala Trp Pro Arg Ile Met Pro Ala Gly Ile Ile Asn Glu
                85                  90                  95

Glu Gly Leu Leu Phe Tyr Glu His Leu Leu Asp Glu Ile Glu Leu Ala
            100                 105                 110

Gly Leu Ile Pro Met Leu Thr Leu Tyr His Trp Asp Leu Pro Gln Trp
        115                 120                 125

Ile Glu Asp Glu Gly Gly Trp Thr Gln Arg Glu Thr Ile Gln His Phe
    130                 135                 140
```

Lys Thr Tyr Ala Ser Val Ile Met Asp Arg Phe Gly Glu Arg Ile Asn
145                 150                 155                 160

Trp Trp Asn Thr Ile Asn Glu Pro Tyr Cys Ala Ser Ile Leu Gly Tyr
            165                 170                 175

Gly Thr Gly Glu His Ala Pro Gly His Glu Asn Trp Arg Glu Ala Phe
            180                 185                 190

Thr Ala Ala His His Ile Leu Met Cys His Gly Ile Ala Ser Asn Leu
            195                 200                 205

His Lys Glu Lys Gly Leu Thr Gly Lys Ile Gly Ile Thr Leu Asn Met
        210                 215                 220

Glu His Val Asp Ala Ala Ser Glu Arg Pro Glu Asp Val Ala Ala Ala
225                 230                 235                 240

Ile Arg Arg Asp Gly Phe Ile Asn Arg Trp Phe Ala Glu Pro Leu Phe
                245                 250                 255

Asn Gly Lys Tyr Pro Glu Asp Met Val Glu Trp Tyr Gly Thr Tyr Leu
            260                 265                 270

Asn Gly Leu Asp Phe Val Gln Pro Gly Asp Met Glu Leu Ile Gln Gln
            275                 280                 285

Pro Gly Asp Phe Leu Gly Ile Asn Tyr Tyr Thr Arg Ser Ile Ile Arg
290                 295                 300

Ser Thr Asn Asp Ala Ser Leu Leu Gln Val Glu Gln Val His Met Glu
305                 310                 315                 320

Glu Pro Val Thr Asp Met Gly Trp Glu Ile His Pro Glu Ser Phe Tyr
                325                 330                 335

Lys Leu Leu Thr Arg Ile Glu Lys Asp Phe Ser Lys Gly Leu Pro Ile
            340                 345                 350

Leu Ile Thr Glu Asn Gly Ala Ala Met Arg Asp Glu Leu Val Asn Gly
            355                 360                 365

Gln Ile Glu Asp Thr Gly Arg His Gly Tyr Ile Glu Glu His Leu Lys
        370                 375                 380

Ala Cys His Arg Phe Ile Glu Glu Gly Gly Gln Leu Lys Gly Tyr Phe
385                 390                 395                 400

Val Trp Ser Phe Leu Asp Asn Phe Glu Trp Ala Trp Gly Tyr Ser Lys
                405                 410                 415

Arg Phe Gly Ile Val His Ile Asn Tyr Glu Thr Gln Glu Arg Thr Pro
            420                 425                 430

Lys Gln Ser Ala Leu Trp Phe Lys Gln Met Met Ala Lys Asn Gly Phe
        435                 440                 445

<210> SEQ ID NO 30
<211> LENGTH: 566
<212> TYPE: PRT
<213> ORGANISM: Zea mays

<400> SEQUENCE: 30

Met Ala Pro Leu Leu Ala Ala Met Asn His Ala Ala His Pro
1               5                   10                  15

Gly Leu Arg Ser His Leu Val Gly Pro Asn Asn Glu Ser Phe Ser Arg
            20                  25                  30

His His Leu Pro Ser Ser Ser Pro Gln Ser Ser Lys Arg Arg Cys Asn
        35                  40                  45

Leu Ser Phe Thr Thr Arg Ser Ala Arg Val Gly Ser Gln Asn Gly Val
    50                  55                  60

Gln Met Leu Ser Pro Ser Glu Ile Pro Gln Arg Asp Trp Phe Pro Ser
65                  70                  75                  80

-continued

Asp Phe Thr Phe Gly Ala Ala Thr Ser Ala Tyr Gln Ile Glu Gly Ala
                 85                  90                  95

Trp Asn Glu Asp Gly Lys Gly Glu Ser Asn Trp Asp His Phe Cys His
            100                 105                 110

Asn His Pro Glu Arg Ile Leu Asp Gly Ser Asn Ser Asp Ile Gly Ala
            115                 120                 125

Asn Ser Tyr His Met Tyr Lys Thr Asp Val Arg Leu Leu Lys Glu Met
130                 135                 140

Gly Met Asp Ala Tyr Arg Phe Ser Ile Ser Trp Pro Arg Ile Leu Pro
145                 150                 155                 160

Lys Gly Thr Lys Glu Gly Gly Ile Asn Pro Asp Gly Ile Lys Tyr Tyr
                165                 170                 175

Arg Asn Leu Ile Asn Leu Leu Leu Glu Asn Gly Ile Glu Pro Tyr Val
            180                 185                 190

Thr Ile Phe His Trp Asp Val Pro Gln Ala Leu Glu Glu Lys Tyr Gly
            195                 200                 205

Gly Phe Leu Asp Lys Ser His Lys Ser Ile Val Glu Asp Tyr Thr Tyr
210                 215                 220

Phe Ala Lys Val Cys Phe Asp Asn Phe Gly Asp Lys Val Lys Asn Trp
225                 230                 235                 240

Leu Thr Phe Asn Glu Pro Gln Thr Phe Thr Ser Phe Ser Tyr Gly Thr
                245                 250                 255

Gly Val Phe Ala Pro Gly Arg Cys Ser Pro Gly Leu Asp Cys Ala Tyr
            260                 265                 270

Pro Thr Gly Asn Ser Leu Val Glu Pro Tyr Thr Ala Gly His Asn Ile
            275                 280                 285

Leu Leu Ala His Ala Glu Ala Val Asp Leu Tyr Asn Lys His Tyr Lys
290                 295                 300

Arg Asp Asp Thr Arg Ile Gly Leu Ala Phe Asp Val Met Gly Arg Val
305                 310                 315                 320

Pro Tyr Gly Thr Ser Phe Leu Asp Lys Gln Ala Glu Glu Arg Ser Trp
                325                 330                 335

Asp Ile Asn Leu Gly Trp Phe Leu Glu Pro Val Val Arg Gly Asp Tyr
            340                 345                 350

Pro Phe Ser Met Arg Ser Leu Ala Arg Glu Arg Leu Pro Phe Phe Lys
            355                 360                 365

Asp Glu Gln Lys Glu Lys Leu Ala Gly Ser Tyr Asn Met Leu Gly Leu
370                 375                 380

Asn Tyr Tyr Thr Ser Arg Phe Ser Lys Asn Ile Asp Ile Ser Pro Asn
385                 390                 395                 400

Tyr Ser Pro Val Leu Asn Thr Asp Asp Ala Tyr Ala Ser Gln Glu Val
                405                 410                 415

Asn Gly Pro Asp Gly Lys Pro Ile Gly Pro Pro Met Gly Asn Pro Trp
            420                 425                 430

Ile Tyr Met Tyr Pro Glu Gly Leu Lys Asp Leu Leu Met Ile Met Lys
            435                 440                 445

Asn Lys Tyr Gly Asn Pro Pro Ile Tyr Ile Thr Glu Asn Gly Ile Gly
450                 455                 460

Asp Val Asp Thr Lys Glu Thr Pro Leu Pro Met Glu Ala Ala Leu Asn
465                 470                 475                 480

Asp Tyr Lys Arg Leu Asp Tyr Ile Gln Arg His Ile Ala Thr Leu Lys
                485                 490                 495

-continued

```
Glu Ser Ile Asp Leu Gly Ser Asn Val Gln Gly Tyr Phe Ala Trp Ser
                500                 505                 510

Leu Leu Asp Asn Phe Glu Trp Phe Ala Gly Phe Thr Glu Arg Tyr Gly
            515                 520                 525

Ile Val Tyr Val Asp Arg Asn Asn Cys Thr Arg Tyr Met Lys Glu
        530                 535                 540

Ser Ala Lys Trp Leu Lys Glu Phe Asn Thr Ala Lys Lys Pro Ser Lys
545                 550                 555                 560

Lys Ile Leu Thr Pro Ala
                565

<210> SEQ ID NO 31
<211> LENGTH: 459
<212> TYPE: PRT
<213> ORGANISM: Agrobacterium sp. ATCC 21400

<400> SEQUENCE: 31

Met Thr Asp Pro Asn Thr Leu Ala Ala Arg Phe Pro Gly Asp Phe Leu
1               5                   10                  15

Phe Gly Val Ala Thr Ala Ser Phe Gln Ile Glu Gly Ser Thr Lys Ala
            20                  25                  30

Asp Gly Arg Lys Pro Ser Ile Trp Asp Ala Phe Cys Asn Met Pro Gly
        35                  40                  45

His Val Phe Gly Arg His Asn Gly Asp Ile Ala Cys Asp His Tyr Asn
    50                  55                  60

Arg Trp Glu Glu Asp Leu Asp Leu Ile Lys Glu Met Gly Val Glu Ala
65                  70                  75                  80

Tyr Arg Phe Ser Leu Ala Trp Pro Arg Ile Ile Pro Asp Gly Phe Gly
                85                  90                  95

Pro Ile Asn Glu Lys Gly Leu Asp Phe Tyr Asp Arg Leu Val Asp Gly
            100                 105                 110

Cys Lys Ala Arg Gly Ile Lys Thr Tyr Ala Thr Leu Tyr His Trp Asp
        115                 120                 125

Leu Pro Leu Thr Leu Met Gly Asp Gly Gly Trp Ala Ser Arg Ser Thr
    130                 135                 140

Ala His Ala Phe Gln Arg Tyr Ala Lys Thr Val Met Ala Arg Leu Gly
145                 150                 155                 160

Asp Arg Leu Asp Ala Val Ala Thr Phe Asn Glu Pro Trp Cys Ala Val
                165                 170                 175

Trp Leu Ser His Leu Tyr Gly Val His Ala Pro Gly Glu Arg Asn Met
            180                 185                 190

Glu Ala Ala Leu Ala Ala Met His His Ile Asn Leu Ala His Gly Phe
        195                 200                 205

Gly Val Glu Ala Ser Arg His Val Ala Pro Lys Val Pro Val Gly Leu
    210                 215                 220

Val Leu Asn Ala His Ser Ala Ile Pro Ala Ser Asp Gly Glu Ala Asp
225                 230                 235                 240

Leu Lys Ala Ala Glu Arg Ala Phe Gln Phe His Asn Gly Ala Phe Phe
                245                 250                 255

Asp Pro Val Phe Lys Gly Glu Tyr Pro Ala Glu Met Met Glu Ala Leu
            260                 265                 270

Gly Asp Arg Met Pro Val Val Glu Ala Glu Asp Leu Gly Ile Ile Ser
        275                 280                 285

Gln Lys Leu Asp Trp Trp Gly Leu Asn Tyr Tyr Thr Pro Met Arg Val
    290                 295                 300
```

```
Ala Asp Asp Ala Thr Pro Gly Val Glu Phe Pro Ala Thr Met Pro Ala
305                 310                 315                 320

Pro Ala Val Ser Asp Val Lys Thr Asp Ile Gly Trp Glu Val Tyr Ala
            325                 330                 335

Pro Ala Leu His Thr Leu Val Glu Thr Leu Tyr Glu Arg Tyr Asp Leu
            340                 345                 350

Pro Glu Cys Tyr Ile Thr Glu Asn Gly Ala Cys Tyr Asn Met Gly Val
            355                 360                 365

Glu Asn Gly Gln Val Asn Asp Gln Pro Arg Leu Asp Tyr Tyr Ala Glu
        370                 375                 380

His Leu Gly Ile Val Ala Asp Leu Ile Arg Asp Gly Tyr Pro Met Arg
385                 390                 395                 400

Gly Tyr Phe Ala Trp Ser Leu Met Asp Asn Phe Glu Trp Ala Glu Gly
            405                 410                 415

Tyr Arg Met Arg Phe Gly Leu Val His Val Asp Tyr Gln Thr Gln Val
            420                 425                 430

Arg Thr Val Lys Asn Ser Gly Lys Trp Tyr Ser Ala Leu Ala Ser Gly
            435                 440                 445

Phe Pro Lys Gly Asn His Gly Val Ala Lys Gly
    450                 455

<210> SEQ ID NO 32
<211> LENGTH: 818
<212> TYPE: PRT
<213> ORGANISM: Agrobacterium tumefaciens

<400> SEQUENCE: 32

Met Ile Asp Asp Ile Leu Asp Lys Met Thr Leu Glu Glu Gln Val Ser
1               5                   10                  15

Leu Leu Ser Gly Ala Asp Phe Trp Thr Thr Val Ala Ile Glu Arg Leu
            20                  25                  30

Gly Val Pro Lys Ile Lys Val Thr Asp Gly Pro Asn Gly Ala Arg Gly
        35                  40                  45

Gly Gly Ser Leu Val Gly Gly Val Lys Ser Ala Cys Phe Pro Val Ala
    50                  55                  60

Ile Ala Leu Gly Ala Thr Trp Asp Pro Glu Leu Ile Glu Arg Ala Gly
65                  70                  75                  80

Val Ala Leu Gly Gly Gln Ala Lys Ser Lys Gly Ala Ser Val Leu Leu
                85                  90                  95

Ala Pro Thr Val Asn Ile His Arg Ser Gly Leu Asn Gly Arg Asn Phe
            100                 105                 110

Glu Cys Tyr Ser Glu Asp Pro Ala Leu Thr Ala Ala Cys Ala Val Ala
        115                 120                 125

Tyr Ile Asn Gly Val Gln Ser Gln Gly Val Ala Thr Ile Lys His
130                 135                 140

Phe Val Ala Asn Glu Ser Glu Ile Glu Arg Gln Thr Met Ser Ser Asp
145                 150                 155                 160

Val Asp Glu Arg Thr Leu Arg Glu Ile Tyr Leu Pro Pro Phe Glu Glu
            165                 170                 175

Ala Val Lys Lys Ala Gly Val Lys Ala Val Met Ser Ser Tyr Asn Lys
            180                 185                 190

Leu Asn Gly Thr Tyr Thr Ser Glu Asn Pro Trp Leu Leu Thr Lys Val
        195                 200                 205

Leu Arg Glu Glu Trp Gly Phe Asp Gly Val Val Met Ser Asp Trp Phe
```

```
             210                 215                 220
Gly Ser His Ser Thr Ala Glu Thr Ile Asn Ala Gly Leu Asp Leu Glu
225                 230                 235                 240

Met Pro Gly Pro Trp Arg Asp Arg Gly Glu Lys Leu Val Ala Ala Val
                245                 250                 255

Arg Glu Gly Lys Val Lys Ala Glu Thr Val Arg Ala Ser Ala Arg Arg
                260                 265                 270

Ile Leu Leu Leu Leu Glu Arg Val Gly Ala Phe Glu Lys Ala Pro Asp
                275                 280                 285

Leu Ala Glu His Ala Leu Asp Leu Pro Glu Asp Arg Ala Leu Ile Arg
            290                 295                 300

Gln Leu Gly Ala Glu Gly Ala Val Leu Leu Lys Asn Asp Gly Val Leu
305                 310                 315                 320

Pro Leu Ala Lys Ser Ser Phe Asp Gln Ile Ala Val Ile Gly Pro Asn
                325                 330                 335

Ala Ala Ser Ala Arg Val Met Gly Gly Gly Ser Ala Arg Ile Ala Ala
                340                 345                 350

His Tyr Thr Val Ser Pro Leu Glu Gly Ile Arg Ala Ala Leu Ser Asn
            355                 360                 365

Ala Asn Ser Leu Arg His Ala Val Gly Cys Asn Asn Asn Arg Leu Ile
370                 375                 380

Asp Val Phe Ser Gly Glu Met Thr Val Glu Tyr Phe Lys Gly Arg Gly
385                 390                 395                 400

Phe Glu Ser Arg Pro Val His Val Glu Thr Val Glu Lys Gly Glu Phe
                405                 410                 415

Phe Trp Phe Asp Leu Pro Ser Gly Asp Leu Asp Leu Ala Asp Phe Ser
                420                 425                 430

Ala Arg Met Thr Ala Thr Phe Val Pro Gln Glu Thr Gly Glu His Ile
            435                 440                 445

Phe Gly Met Thr Asn Ala Gly Leu Ala Arg Leu Phe Val Asp Gly Glu
            450                 455                 460

Leu Val Val Asp Gly Tyr Asp Gly Trp Thr Lys Gly Glu Asn Phe Phe
465                 470                 475                 480

Gly Thr Ala Asn Ser Glu Gln Arg Arg Ala Val Thr Leu Gly Ala Ala
                485                 490                 495

Arg Arg Tyr Arg Val Val Val Glu Tyr Glu Ala Pro Lys Ala Ser Leu
                500                 505                 510

Asp Gly Ile Asn Ile Cys Ala Leu Arg Phe Gly Val Glu Lys Pro Leu
            515                 520                 525

Gly Asp Ala Gly Ile Ala Glu Ala Val Glu Thr Ala Arg Lys Ser Asp
            530                 535                 540

Ile Val Leu Leu Leu Val Gly Arg Glu Gly Glu Trp Asp Thr Glu Gly
545                 550                 555                 560

Leu Asp Leu Pro Asp Met Arg Leu Pro Gly Arg Gln Glu Glu Leu Ile
                565                 570                 575

Glu Ala Val Ala Glu Thr Asn Pro Asn Val Val Val Leu Gln Thr
            580                 585                 590

Gly Gly Pro Ile Glu Met Pro Trp Leu Gly Lys Val Arg Ala Val Leu
            595                 600                 605

Gln Met Trp Tyr Pro Gly Gln Glu Leu Gly Asn Ala Leu Ala Asp Val
            610                 615                 620

Leu Phe Gly Asp Val Glu Pro Ala Gly Arg Leu Pro Gln Thr Phe Pro
625                 630                 635                 640
```

Lys Ala Leu Thr Asp Asn Ser Ala Ile Thr Asp Pro Ser Ile Tyr
            645                 650                 655

Pro Gly Gln Asp Gly His Val Arg Tyr Ala Glu Gly Ile Phe Val Gly
        660                 665                 670

Tyr Arg His His Asp Thr Arg Glu Ile Glu Pro Leu Phe Pro Phe Gly
        675                 680                 685

Phe Gly Leu Gly Tyr Thr Arg Phe Thr Trp Gly Ala Pro Gln Leu Ser
        690                 695                 700

Gly Thr Glu Met Gly Ala Asp Gly Leu Thr Val Thr Val Asp Val Thr
705                 710                 715                 720

Asn Ile Gly Asp Arg Ala Gly Ser Asp Val Val Gln Leu Tyr Val His
                725                 730                 735

Ser Pro Asn Ala Arg Val Glu Arg Pro Phe Lys Glu Leu Arg Ala Phe
            740                 745                 750

Ala Lys Leu Lys Leu Ala Pro Gly Ala Thr Gly Thr Ala Val Leu Lys
        755                 760                 765

Ile Ala Pro Arg Asp Leu Ala Tyr Phe Asp Val Glu Ala Gly Arg Phe
        770                 775                 780

Arg Ala Asp Ala Gly Lys Tyr Glu Leu Ile Val Ala Ala Ser Ala Ile
785                 790                 795                 800

Asp Ile Arg Ala Ser Val Ser Ile His Leu Pro Val Asp His Val Met
                805                 810                 815

Glu Pro

<210> SEQ ID NO 33
<211> LENGTH: 830
<212> TYPE: PRT
<213> ORGANISM: Butyrivibrio fibrisolvens

<400> SEQUENCE: 33

Met Glu Lys Trp Ala Arg Ile Lys Tyr Thr Pro Asn Leu Pro Leu Gly
1               5                   10                  15

Glu Asn Gly Glu Arg Val Thr Ala Ser Gln Lys His Ile Glu Leu Ser
            20                  25                  30

Cys Glu Ala Ala Cys Glu Gly Met Val Leu Leu Lys Asn Asp Arg Asn
        35                  40                  45

Val Leu Pro Ile Arg Lys Gly Thr Arg Val Ala Leu Phe Gly Lys Gly
    50                  55                  60

Val Phe Asp Tyr Val Lys Gly Gly Gly Ser Gly Asp Val Thr Val
65                  70                  75                  80

Pro Tyr Ile Arg Asn Leu Tyr Glu Gly Leu Ser Gln Tyr Thr Ser Asp
                85                  90                  95

Ile Ser Ile Tyr Asp Lys Ser Val Arg Phe Tyr Gln Glu Tyr Val Ala
            100                 105                 110

Asp Gln Tyr Arg Leu Gly Ile Ala Pro Gly Met Ile Lys Glu Pro Ala
        115                 120                 125

Leu Pro Glu Asp Ile Leu Ala Asp Ala Ala Tyr Ala Asp Thr Ala
    130                 135                 140

Ile Ile Ala Ile Ser Arg Phe Ser Gly Glu Gly Trp Asp Arg Lys Val
145                 150                 155                 160

Ala Gly Val Asp Arg Glu Ile Lys Cys Glu Ala Lys Asp Leu Val Glu
                165                 170                 175

Gln Gly Asn Lys Ile Phe Asp His Gly Asp Phe Tyr Leu Thr Asn Ala
            180                 185                 190

```
Glu Lys Lys Met Val Lys Met Val Lys Glu Asn Phe Ser Ser Val Ile
            195                 200                 205

Val Val Met Asn Val Gly Gly Val Val Asp Thr Thr Trp Phe Lys Lys
        210                 215                 220

Asp Asp Gln Ile Ser Ser Val Leu Met Ala Trp Gln Gly Gly Ile Glu
225                 230                 235                 240

Gly Gly Leu Ala Ala Ala Arg Ile Leu Leu Gly Lys Val Asn Pro Ser
                245                 250                 255

Gly Lys Leu Ser Asp Thr Phe Ala Ala Arg Leu Glu Asp Tyr Pro Ser
                260                 265                 270

Thr Glu Gly Phe His Glu Asp Asp Tyr Val Asp Tyr Thr Glu Asp
                275                 280                 285

Ile Tyr Val Gly Tyr Arg Tyr Phe Glu Thr Ile Pro Gly Ala Lys Glu
        290                 295                 300

Lys Val Asn Tyr Pro Phe Gly Tyr Gly Leu Ser Tyr Thr Thr Phe Leu
305                 310                 315                 320

Leu Glu Asp Tyr Lys Ala Glu Pro Phe Val Ala Ser Ala Ala Asp Glu
                325                 330                 335

Val Gly Lys Ser Asp Ser Asp Leu Ala Asp Ala Ile Val Ala Ser Val
                340                 345                 350

Thr Val Thr Asn Ile Gly Lys Ile Pro Gly Lys Glu Val Val Gln Leu
        355                 360                 365

Tyr Tyr Ser Ala Pro Gln Gly Lys Leu Gly Lys Pro Ala Lys Val Leu
        370                 375                 380

Gly Gly Tyr Ala Lys Thr Arg Leu Leu Gln Pro Gly Glu Ser Gln Arg
385                 390                 395                 400

Val Thr Ile Ala Leu Tyr Met Glu Asp Met Ala Ser Tyr Asp Asp Leu
                405                 410                 415

Gly Lys Val Lys Lys Ala Ala Trp Leu Leu Glu Lys Gly Glu Tyr His
                420                 425                 430

Phe Phe Leu Gly Thr Ser Val Arg Asp Thr Arg Leu Leu Asp Tyr Thr
        435                 440                 445

Tyr Glu Leu Ser Lys Asn Ile Ile Val Glu Gln Val Ser Asn Lys Leu
        450                 455                 460

Val Pro Thr Ser Leu Pro Lys Arg Met Leu Ala Asp Gly Thr Tyr Glu
465                 470                 475                 480

Glu Leu Pro Gln Thr Glu Pro Val Asp Thr Tyr Ala Thr Ile Phe Pro
                485                 490                 495

Arg Pro Lys Asn Trp Lys Glu Thr Ile Glu His Asp Val Leu Lys Thr
                500                 505                 510

Pro Val Val Arg Pro Gln Asp Arg Phe Gln Leu Phe Leu Pro Pro Lys
        515                 520                 525

Glu Gly Asp Pro Lys Lys Phe Ile Glu Val Ala Glu Cys Lys Val Thr
        530                 535                 540

Leu Glu Asp Phe Ile Ala Gln Leu Ser Asn Glu Gln Leu Ala Ser Leu
545                 550                 555                 560

Leu Gly Gly Gln Pro Asn Val Gly Met Ala Asn Thr Phe Gly Tyr Gly
                565                 570                 575

Asn Leu Pro Glu Val Gly Val Pro Asn Ala Gln Thr Cys Asp Gly Pro
                580                 585                 590

Ala Gly Val Arg Ile Ala Pro Glu Val Gly Val Val Thr Thr Ala Phe
        595                 600                 605
```

```
Pro Cys Ser Thr Leu Leu Ala Cys Thr Trp Asn Glu Asp Ile Cys Tyr
    610                 615                 620

Glu Val Gly Val Ala Gly Gly Glu Ala Lys Glu Cys Asn Phe Gly
625                 630                 635                 640

Ala Trp Leu Thr Pro Ala Val Asn Ile His Arg Ser Pro Leu Cys Gly
                645                 650                 655

Arg Asn Phe Glu Tyr Tyr Ser Glu Asp Pro Phe Leu Ala Gly Lys Gln
                660                 665                 670

Ala Ala Ala Met Val Arg Gly Ile Gln Ser Asn Asn Ile Ile Ala Thr
            675                 680                 685

Pro Lys His Phe Ala Leu Asn Asn Lys Glu Ser Asn Arg Lys Gly Ser
    690                 695                 700

Asp Ser Arg Ala Ser Glu Arg Ala Ile Arg Glu Ile Tyr Leu Lys Ala
705                 710                 715                 720

Phe Glu Ile Ile Val Lys Glu Gln Ser Pro Gly Ala Ser Cys Leu Gln
                725                 730                 735

Tyr Asn Ile Val Asn Gly Gln Arg Ser Ser Glu Ser His Asp Leu Leu
                740                 745                 750

Thr Gly Ile Leu Arg Asp Glu Trp Gly Phe Glu Gly Val Val Val Ser
        755                 760                 765

Asp Trp Trp Gly Phe Gly Glu His Tyr Lys Glu Val Leu Ala Gly Asn
    770                 775                 780

Asp Ile Lys Met Gly Cys Gly Tyr Thr Glu Gln Leu Leu Glu Ala Ile
785                 790                 795                 800

Asp Lys Lys Ala Leu Lys Arg Lys Asp Leu Glu Lys Arg Gln Ser Glu
                805                 810                 815

Ser Ser Arg Cys Phe Ser Asn Ser Thr Lys Leu Lys Ala Ala
                820                 825                 830

<210> SEQ ID NO 34
<211> LENGTH: 455
<212> TYPE: PRT
<213> ORGANISM: Caldocellum saccharolyticum

<400> SEQUENCE: 34

Met Asp Met Ser Phe Pro Lys Gly Phe Leu Trp Gly Ala Ala Thr Ala
1               5                   10                  15

Ser Tyr Gln Ile Glu Gly Ala Trp Asn Glu Asp Gly Lys Gly Glu Ser
                20                  25                  30

Ile Trp Asp Arg Phe Thr His Gln Lys Arg Asn Ile Leu Tyr Gly His
            35                  40                  45

Asn Gly Asp Val Ala Cys Asp His Tyr His Arg Phe Glu Glu Asp Val
    50                  55                  60

Ser Leu Met Lys Glu Leu Gly Leu Lys Ala Tyr Arg Phe Ser Ile Ala
65                  70                  75                  80

Trp Thr Arg Ile Phe Pro Asp Gly Phe Gly Thr Val Asn Gln Lys Gly
                85                  90                  95

Leu Glu Phe Tyr Asp Arg Leu Ile Asn Lys Leu Val Glu Asn Gly Ile
                100                 105                 110

Glu Pro Val Val Thr Leu Tyr His Trp Asp Leu Pro Gln Lys Leu Gln
            115                 120                 125

Asp Ile Gly Gly Trp Ala Asn Pro Glu Ile Val Asn Tyr Tyr Phe Asp
    130                 135                 140

Tyr Ala Met Leu Val Ile Asn Arg Tyr Lys Asp Lys Val Lys Lys Trp
145                 150                 155                 160
```

```
Ile Thr Phe Asn Glu Pro Tyr Cys Ile Ala Phe Leu Gly Tyr Phe His
                165                 170                 175

Gly Ile His Ala Pro Gly Ile Lys Asp Phe Lys Val Ala Met Asp Val
            180                 185                 190

Val His Ser Leu Met Leu Ser His Phe Lys Val Val Lys Ala Val Lys
        195                 200                 205

Glu Asn Asn Ile Asp Val Glu Val Gly Ile Thr Leu Asn Leu Thr Pro
    210                 215                 220

Val Tyr Leu Gln Thr Glu Arg Leu Gly Tyr Lys Val Ser Glu Ile Glu
225                 230                 235                 240

Arg Glu Met Val Ser Leu Ser Ser Gln Leu Asp Asn Gln Leu Phe Leu
                245                 250                 255

Asp Pro Val Leu Lys Gly Ser Tyr Pro Gln Lys Leu Leu Asp Tyr Leu
            260                 265                 270

Val Gln Lys Asp Leu Leu Asp Ser Gln Lys Ala Leu Ser Met Gln Gln
        275                 280                 285

Glu Val Lys Glu Asn Phe Ile Phe Pro Asp Phe Leu Gly Ile Asn Tyr
    290                 295                 300

Tyr Thr Arg Ala Val Arg Leu Tyr Asp Glu Asn Ser Ser Trp Ile Phe
305                 310                 315                 320

Pro Ile Arg Trp Glu His Pro Ala Gly Glu Tyr Thr Glu Met Gly Trp
                325                 330                 335

Glu Val Phe Pro Gln Gly Leu Phe Asp Leu Leu Ile Trp Ile Lys Glu
            340                 345                 350

Ser Tyr Pro Gln Ile Pro Ile Tyr Ile Thr Glu Asn Gly Ala Ala Tyr
        355                 360                 365

Asn Asp Ile Val Thr Glu Asp Gly Lys Val His Asp Ser Lys Arg Ile
    370                 375                 380

Glu Tyr Leu Lys Gln His Phe Glu Ala Ala Arg Lys Ala Ile Glu Asn
385                 390                 395                 400

Gly Val Asp Leu Arg Gly Tyr Phe Val Trp Ser Leu Met Asp Asn Phe
                405                 410                 415

Glu Trp Ala Met Gly Tyr Thr Lys Arg Phe Gly Ile Ile Tyr Val Asp
            420                 425                 430

Tyr Glu Thr Gln Lys Arg Ile Lys Lys Asp Ser Phe Tyr Phe Tyr Gln
        435                 440                 445

Gln Tyr Ile Lys Glu Asn Ser
    450                 455

<210> SEQ ID NO 35
<211> LENGTH: 825
<212> TYPE: PRT
<213> ORGANISM: Hansenula anomala

<400> SEQUENCE: 35

Met Leu Leu Pro Leu Tyr Gly Leu Ala Ser Phe Leu Val Leu Ser Gln
1               5                   10                  15

Ala Ala Leu Val Asn Thr Ser Ala Pro Gln Ala Ser Asn Asp Asp Pro
            20                  25                  30

Phe Asn His Ser Pro Ser Phe Tyr Pro Thr Pro Gln Gly Gly Arg Ile
        35                  40                  45

Asn Asp Gly Lys Trp Gln Ala Ala Phe Tyr Arg Ala Arg Glu Leu Val
    50                  55                  60

Asp Gln Met Ser Ile Ala Glu Lys Val Asn Leu Thr Thr Gly Val Gly
```

-continued

```
        65                  70                  75                  80
Ser Ala Ser Gly Pro Cys Ser Gly Asn Thr Gly Ser Val Pro Arg Leu
                85                  90                  95
Asn Ile Ser Ser Ile Cys Val Gln Asp Gly Pro Leu Ser Val Arg Ala
                100                 105                 110
Ala Asp Leu Thr Asp Val Phe Pro Cys Gly Met Ala Ala Ser Ser Ser
                115                 120                 125
Phe Asn Lys Gln Leu Ile Tyr Asp Arg Ala Val Ala Ile Gly Ser Glu
                130                 135                 140
Phe Lys Gly Lys Gly Ala Asp Ala Ile Leu Gly Pro Val Tyr Gly Pro
145                 150                 155                 160
Met Gly Val Lys Ala Ala Gly Gly Arg Gly Trp Glu Gly His Gly Pro
                165                 170                 175
Asp Pro Tyr Leu Glu Gly Val Ile Ala Tyr Leu Gln Thr Ile Gly Ile
                180                 185                 190
Gln Ser Gln Gly Val Val Ser Thr Ala Lys His Leu Ile Gly Asn Glu
                195                 200                 205
Gln Glu His Phe Arg Phe Ala Lys Lys Asp Lys His Ala Gly Lys Ile
                210                 215                 220
Asp Pro Gly Met Phe Asn Thr Ser Ser Ser Leu Ser Ser Glu Ile Asp
225                 230                 235                 240
Asp Arg Ala Met His Glu Ile Tyr Leu Trp Pro Phe Ala Glu Ala Val
                245                 250                 255
Arg Gly Gly Val Ser Ser Ile Met Cys Ser Tyr Asn Lys Leu Asn Gly
                260                 265                 270
Ser His Ala Cys Gln Asn Ser Tyr Leu Leu Asn Tyr Leu Leu Lys Glu
                275                 280                 285
Glu Leu Gly Phe Gln Gly Phe Val Met Thr Asp Trp Gly Ala Leu Tyr
                290                 295                 300
Ser Gly Ile Asp Ala Ala Asn Ala Gly Leu Asp Met Asp Met Pro Cys
305                 310                 315                 320
Glu Ala Gln Tyr Phe Gly Gly Asn Leu Thr Thr Ala Val Leu Asn Gly
                325                 330                 335
Thr Leu Pro Gln Asp Arg Leu Asp Asp Met Ala Thr Arg Ile Leu Ser
                340                 345                 350
Ala Leu Ile Tyr Ser Gly Val His Asn Pro Asp Gly Pro Asn Tyr Asn
                355                 360                 365
Ala Gln Thr Phe Leu Thr Glu Gly His Glu Tyr Phe Lys Gln Gln Glu
                370                 375                 380
Gly Asp Ile Val Val Leu Asn Lys His Val Asp Val Arg Ser Asp Ile
385                 390                 395                 400
Asn Arg Ala Val Ala Leu Arg Ser Ala Val Glu Gly Val Val Leu Leu
                405                 410                 415
Lys Asn Glu His Glu Thr Leu Pro Leu Gly Arg Glu Lys Val Lys Arg
                420                 425                 430
Ile Ser Ile Leu Gly Gln Ala Ala Gly Asp Asp Ser Lys Gly Thr Ser
                435                 440                 445
Cys Ser Leu Arg Gly Cys Gly Ser Gly Ala Ile Gly Thr Gly Tyr Gly
                450                 455                 460
Ser Gly Ala Gly Thr Phe Ser Tyr Phe Val Thr Pro Ala Asp Gly Ile
465                 470                 475                 480
Gly Ala Arg Ala Gln Gln Glu Lys Ile Ser Tyr Glu Phe Ile Gly Asp
                485                 490                 495
```

```
Ser Trp Asn Gln Ala Ala Met Asp Ser Ala Leu Tyr Ala Asp Ala
            500                 505                 510
Ala Ile Glu Val Ala Asn Ser Val Ala Gly Glu Ile Gly Asp Val
            515                 520                 525
Asp Gly Asn Tyr Gly Asp Leu Asn Asn Leu Thr Leu Trp His Asn Ala
            530                 535                 540
Val Pro Leu Ile Lys Asn Ile Ser Ser Ile Asn Asn Thr Ile Val
545                 550                 555                 560
Ile Val Thr Ser Gly Gln Gln Ile Asp Leu Glu Pro Phe Ile Asp Asn
                565                 570                 575
Glu Asn Val Thr Ala Val Ile Tyr Ser Ser Tyr Leu Gly Gln Asp Phe
            580                 585                 590
Gly Thr Val Leu Ala Lys Val Leu Phe Gly Asp Glu Asn Pro Ser Gly
            595                 600                 605
Lys Leu Pro Phe Thr Ile Ala Lys Asp Val Asn Asp Tyr Ile Pro Val
            610                 615                 620
Ile Glu Lys Val Asp Val Pro Asp Pro Val Asp Lys Phe Thr Glu Ser
625                 630                 635                 640
Ile Tyr Val Asp Tyr Arg Tyr Phe Asp Lys Tyr Asn Lys Pro Val Arg
                645                 650                 655
Tyr Glu Phe Gly Tyr Gly Leu Ser Tyr Ser Asn Phe Ser Leu Ser Asp
            660                 665                 670
Ile Glu Ile Gln Thr Leu Gln Pro Phe Ser Glu Asn Ala Glu Pro Ala
            675                 680                 685
Ala Asn Tyr Ser Glu Thr Tyr Gln Tyr Lys Gln Ser Asn Met Asp Pro
            690                 695                 700
Ser Glu Tyr Thr Val Pro Glu Gly Phe Lys Glu Leu Ala Asn Tyr Thr
705                 710                 715                 720
Tyr Pro Tyr Ile His Asp Ala Ser Ser Ile Lys Ala Asn Ser Ser Tyr
                725                 730                 735
Asp Tyr Pro Glu Gly Tyr Ser Thr Glu Gln Leu Asp Gly Pro Lys Ser
            740                 745                 750
Leu Ala Ala Gly Gly Leu Gly Gly Asn His Thr Cys Gly Met Leu Val
            755                 760                 765
Thr Leu Ser Leu Leu Lys Ser Gln Ile Lys Val Leu Met Leu Val Gly
770                 775                 780
Leu His Leu Asn Cys Met Leu Asp Ile Gln Ile Met Met Asn Ser Gln
785                 790                 795                 800
His Leu Gln Cys Asn Tyr Val Asp Leu Lys Arg Cys Phe Trp Ile Lys
                805                 810                 815
Ile Ile Leu Lys Leu Phe Leu Leu Asn
            820                 825

<210> SEQ ID NO 36
<211> LENGTH: 845
<212> TYPE: PRT
<213> ORGANISM: Kluyveromyces marxianus

<400> SEQUENCE: 36

Met Ser Lys Phe Asp Val Glu Gln Leu Leu Ser Glu Leu Asn Gln Asp
1               5                   10                  15
Glu Lys Ile Ser Leu Leu Ser Ala Val Asp Phe Trp His Thr Lys Lys
            20                  25                  30
Ile Glu Arg Leu Gly Ile Pro Ala Val Arg Val Ser Asp Gly Pro Asn
```

-continued

```
              35                  40                  45
Gly Ile Arg Gly Thr Lys Phe Phe Asp Gly Val Pro Ser Gly Cys Phe
 50                  55                  60

Pro Asn Gly Thr Gly Leu Ala Ser Thr Phe Asp Arg Asp Leu Leu Glu
 65                  70                  75                  80

Thr Ala Gly Lys Leu Met Ala Lys Glu Ser Ile Ala Lys Asn Ala Ala
                     85                  90                  95

Val Ile Leu Gly Pro Thr Thr Asn Met Gln Arg Gly Pro Leu Gly Gly
                100                 105                 110

Arg Gly Phe Glu Ser Phe Ser Glu Asp Pro Tyr Leu Ala Gly Met Ala
                115                 120                 125

Thr Ser Ser Val Val Lys Gly Met Gln Gly Glu Gly Ile Ala Ala Thr
130                 135                 140

Val Lys His Phe Val Cys Asn Asp Leu Glu Asp Gln Arg Phe Ser Ser
145                 150                 155                 160

Asn Ser Ile Val Ser Glu Arg Ala Leu Arg Glu Ile Tyr Leu Glu Pro
                165                 170                 175

Phe Arg Leu Ala Val Lys His Ala Asn Pro Val Cys Ile Met Thr Ala
                180                 185                 190

Tyr Asn Lys Val Asn Gly Asp His Cys Ser Gln Ser Lys Lys Leu Leu
                195                 200                 205

Ile Asp Ile Leu Arg Asp Glu Trp Lys Trp Asp Gly Met Leu Met Ser
210                 215                 220

Asp Trp Phe Gly Thr Tyr Thr Thr Ala Ala Ile Lys Asn Gly Leu
225                 230                 235                 240

Asp Ile Glu Phe Pro Gly Pro Thr Arg Trp Arg Thr Arg Ala Leu Val
                245                 250                 255

Ser His Ser Leu Asn Ser Arg Glu Gln Ile Thr Thr Glu Asp Val Asp
                260                 265                 270

Asp Arg Val Arg Gln Val Leu Lys Met Ile Lys Phe Val Val Asp Asn
                275                 280                 285

Leu Glu Lys Thr Gly Ile Val Glu Asn Gly Pro Glu Ser Thr Ser Asn
                290                 295                 300

Asn Thr Lys Glu Thr Ser Asp Leu Leu Arg Glu Ile Ala Ala Asp Ser
305                 310                 315                 320

Ile Val Leu Leu Lys Asn Lys Asn Asn Tyr Leu Thr Ser Lys Glu Arg
                325                 330                 335

Arg Gln Tyr His Val Ile Gly Pro Asn Ala Lys Ala Lys Thr Ser Ser
                340                 345                 350

Gly Gly Gly Ser Ala Ser Met Asn Ser Tyr Tyr Val Ser Pro Tyr
                355                 360                 365

Glu Gly Ile Val Asn Lys Leu Gly Lys Glu Val Asp Tyr Thr Val Gly
                370                 375                 380

Ala Tyr Ser His Lys Ser Ile Gly Gly Leu Ala Glu Ser Ser Leu Ile
385                 390                 395                 400

Asp Ala Ala Lys Pro Ala Asp Ala Glu Asn Ala Gly Leu Ile Ala Lys
                405                 410                 415

Phe Tyr Ser Asn Pro Val Glu Glu Arg Ser Glu Asp Glu Pro Phe
                420                 425                 430

His Val Thr Lys Val Asn Arg Ser Asn Val His Leu Phe Asp Phe Lys
                435                 440                 445

His Glu Lys Val Asp Pro Lys Asn Pro Tyr Phe Phe Val Thr Leu Thr
450                 455                 460
```

Gly Gln Tyr Val Pro Gln Glu Asp Gly Asp Tyr Ile Phe Ser Leu Gln
465                 470                 475                 480

Val Tyr Gly Ser Gly Leu Phe Tyr Leu Asn Asp Glu Leu Ile Ile Asp
                485                 490                 495

Gln Lys His Asn Gln Glu Arg Gly Ser Phe Cys Phe Gly Ala Gly Thr
            500                 505                 510

Lys Glu Arg Thr Lys Lys Leu Thr Leu Lys Lys Gly Gln Val Tyr Asn
        515                 520                 525

Val Arg Val Glu Tyr Gly Ser Gly Pro Thr Ser Gly Leu Val Gly Glu
    530                 535                 540

Phe Gly Ala Gly Gly Phe Gln Ala Gly Val Ile Lys Ala Ile Asp Asp
545                 550                 555                 560

Asp Glu Glu Ile Arg Asn Ala Ala Glu Leu Ala Ala Lys His Asp Lys
                565                 570                 575

Ala Val Leu Ile Ile Gly Leu Asn Gly Glu Trp Glu Thr Glu Gly Tyr
            580                 585                 590

Asp Arg Glu Asn Met Asp Leu Pro Lys Arg Thr Asn Glu Leu Val Arg
        595                 600                 605

Ala Val Leu Lys Ala Asn Pro Asn Thr Val Ile Val Asn Gln Ser Gly
    610                 615                 620

Thr Pro Val Glu Phe Pro Trp Leu Glu Ala Asn Ala Leu Val Gln
625                 630                 635                 640

Ala Trp Tyr Gly Gly Asn Glu Leu Gly Asn Ala Ile Ala Asp Val Leu
                645                 650                 655

Tyr Gly Asp Val Val Pro Asn Gly Lys Leu Ser Leu Ser Trp Pro Phe
            660                 665                 670

Lys Leu Gln Asp Asn Pro Ala Phe Leu Asn Phe Lys Thr Glu Phe Gly
        675                 680                 685

Arg Val Val Tyr Gly Glu Asp Ile Phe Val Gly Tyr Arg Tyr Tyr Glu
    690                 695                 700

Lys Leu Gln Arg Lys Val Ala Phe Pro Phe Gly Tyr Gly Leu Ser Tyr
705                 710                 715                 720

Thr Thr Phe Glu Leu Asp Ile Ser Asp Phe Lys Val Thr Asp Asp Lys
                725                 730                 735

Ile Asp Ile Ser Val Asp Val Lys Asn Thr Gly Asp Lys Phe Ala Gly
            740                 745                 750

Ser Glu Val Val Gln Val Tyr Phe Ser Ala Leu Asn Ser Lys Val Ser
        755                 760                 765

Arg Pro Val Lys Glu Leu Lys Gly Phe Glu Lys Val His Leu Glu Pro
    770                 775                 780

Gly Glu Lys Lys Thr Val Asn Ile Glu Leu Glu Leu Lys Asp Ala Ile
785                 790                 795                 800

Ser Tyr Phe Asn Glu Glu Leu Gly Lys Trp His Val Glu Ala Gly Glu
                805                 810                 815

Tyr Leu Val Ser Val Gly Thr Ser Ser Asp Asp Ile Leu Ser Val Lys
            820                 825                 830

Glu Phe Lys Val Glu Lys Asp Leu Tyr Trp Lys Gly Leu
        835                 840                 845

<210> SEQ ID NO 37
<211> LENGTH: 947
<212> TYPE: PRT
<213> ORGANISM: Ruminococcus albus

<400> SEQUENCE: 37

```
Met Ile Lys Leu Asp Trp Asn Glu Tyr Leu Glu Lys Ala Ala Glu Val
1               5                   10                  15

Asn Ala Glu Gly Ala Val Leu Leu Val Asn Asn Gly Val Leu Pro Leu
            20                  25                  30

Asp Lys Asn Ala Val Thr Gln Val Phe Gly Arg Ile Gln Leu Asp Tyr
        35                  40                  45

Tyr Lys Ser Gly Thr Gly Ser Gly Gly Met Val Asn Val Ala Lys Val
    50                  55                  60

Thr Gly Ile Thr Asp Gly Leu Ile Glu Ala Gly Ala Lys Leu Asn Glu
65                  70                  75                  80

Asp Val Leu Lys Ala Tyr Lys Asp Tyr Val Ala Glu His Pro Tyr Asp
                85                  90                  95

Tyr Gly Glu Gly Trp Gly Gly Glu Pro Trp Cys Gln Glu Glu Met Pro
            100                 105                 110

Leu Asp Asp Ser Leu Val Lys Arg Ala Ala Glu Ser Ser Asp Thr Ala
        115                 120                 125

Ile Cys Ile Ile Gly Arg Thr Ala Gly Glu Glu Gln Asp Asn Ser Cys
130                 135                 140

Lys Ala Gly Ser Tyr Leu Leu Thr Asp Gly Glu Lys Ala Ile Leu Arg
145                 150                 155                 160

Lys Val Arg Asp Asn Phe Ser Lys Met Val Ile Leu Leu Asn Val Gly
                165                 170                 175

Asn Ile Ile Asp Met Gly Phe Ile Asp Glu Phe Ser Pro Asp Ala Val
            180                 185                 190

Met Tyr Val Trp Gln Gly Gly Met Thr Gly Gly Thr Gly Thr Ala Arg
        195                 200                 205

Val Leu Leu Gly Glu Val Ser Pro Cys Gly Lys Leu Pro Asp Thr Ile
210                 215                 220

Ala Tyr Asp Ile Thr Asp Tyr Pro Ser Asp Lys Asn Phe His Asn Arg
225                 230                 235                 240

Asp Val Asp Ile Tyr Ala Glu Asp Ile Phe Val Gly Tyr Arg Tyr Phe
                245                 250                 255

Asp Thr Phe Ala Lys Asp Arg Val Arg Phe Pro Phe Gly Tyr Gly Leu
            260                 265                 270

Ser Tyr Thr Gln Phe Glu Ile Ser Ala Glu Gly Arg Lys Thr Asp Asp
        275                 280                 285

Gly Val Val Ile Thr Ala Lys Val Lys Asn Ile Gly Ser Ala Ala Gly
290                 295                 300

Lys Glu Val Val Gln Val Tyr Leu Glu Ala Pro Asn Cys Lys Leu Gly
305                 310                 315                 320

Lys Ala Ala Arg Val Leu Cys Gly Phe Glu Lys Thr Lys Val Leu Ala
                325                 330                 335

Pro Asn Glu Glu Gln Thr Leu Thr Ile Glu Val Thr Glu Arg Asp Ile
            340                 345                 350

Ala Ser Tyr Asp Asp Ser Gly Ile Thr Gly Asn Ala Phe Ala Trp Val
        355                 360                 365

Glu Glu Ala Gly Glu Tyr Thr Phe Tyr Ala Gly Ser Asp Val Arg Ser
370                 375                 380

Ala Lys Glu Cys Phe Ala Phe Thr Leu Asp Ser Thr Lys Val Ile Glu
385                 390                 395                 400

Gln Leu Glu Gln Ala Leu Ala Pro Val Thr Pro Phe Lys Arg Met Val
                405                 410                 415
```

```
Arg Thr Ala Glu Gly Leu Ser Tyr Glu Asp Thr Pro Leu Ser Lys Val
            420                 425                 430

Asp Glu Ala Ala Arg Arg Leu Gly Tyr Leu Pro Ala Glu Thr Ala Tyr
            435                 440                 445

Thr Gly Asp Lys Gly Ile Ala Leu Ser Asp Val Ala His Gly Lys Asn
            450                 455                 460

Thr Leu Asp Glu Phe Ile Ala Gln Leu Asp Asp Asn Asp Leu Asn Cys
465                 470                 475                 480

Leu Val Arg Gly Glu Gly Met Cys Ser Pro Lys Val Thr Pro Gly Thr
                485                 490                 495

Ala Ala Ala Phe Gly Gly Val Ala Lys His Leu Glu Glu Leu Gly Ile
            500                 505                 510

Pro Ala Gly Cys Cys Ser Asp Gly Pro Ser Gly Met Arg Leu Asp Val
            515                 520                 525

Gly Thr Lys Ala Phe Ser Leu Pro Asn Gly Thr Leu Ile Ala Ala Thr
            530                 535                 540

Phe Asn Lys Ser Leu Ile Thr Glu Leu Phe Thr Tyr Leu Gly Leu Glu
545                 550                 555                 560

Met Arg Ala Asn Lys Val Asp Cys Leu Leu Gly Pro Gly Met Asn Ile
                565                 570                 575

His Arg His Pro Leu Asn Gly Arg Asn Phe Glu Tyr Phe Ser Glu Asp
            580                 585                 590

Pro Phe Leu Thr Gly Thr Met Ala Ala Ala Glu Leu Glu Gly Leu His
            595                 600                 605

Ser Val Gly Val Glu Gly Thr Ile Lys His Phe Cys Ala Asn Asn Gln
            610                 615                 620

Glu Thr Asn Arg His Phe Ile Asp Ser Val Ala Ser Glu Arg Ala Leu
625                 630                 635                 640

Arg Glu Ile Tyr Leu Lys Gly Phe Glu Ile Ala Val Arg Lys Ser Lys
                645                 650                 655

Ala Arg Ser Val Met Thr Thr Tyr Gly Lys Val Asn Gly Leu Trp Thr
            660                 665                 670

Ala Gly Ser Phe Asp Leu Asn Thr Met Ile Leu Arg Lys Gln Trp Gly
            675                 680                 685

Phe Asp Gly Phe Thr Met Thr Asp Trp Trp Ala Asn Ile Asn Asp Arg
690                 695                 700

Gly Cys Ala Pro Asp Lys Asn Asn Phe Ala Ala Met Val Arg Ala Gln
705                 710                 715                 720

Asn Asp Val Tyr Met Val Cys Ala Asp Gly Glu Ser Gly Ser Asp Asn
                725                 730                 735

Val Ile Ala Ala Leu Ala Asp Gly Arg Leu Thr Arg Ala Glu Leu Gln
            740                 745                 750

Arg Ser Ala Arg Asn Ile Leu Ser Phe Met Met Ser Thr His Ala Met
            755                 760                 765

Ala Arg Lys Leu Gly Glu Asp Glu Ala Val Glu Val Ile Asn Lys Pro
            770                 775                 780

Ala Glu Thr Val Asp Asp Gly Glu Gly Asp Arg Val Phe Leu Leu Asp
785                 790                 795                 800

Gly Asp Leu Thr Ile Asp Met Ser Gly Val Lys Thr Glu Arg Asn Leu
                805                 810                 815

Asp Tyr Ser Phe Thr Val Asp Val Ala Gln Phe Gly Gln Tyr Arg Met
            820                 825                 830
```

-continued

Glu Met Thr Ala Ser Ser Thr Gln Ser Glu Leu Ala Gln Met Pro Val
835                 840                 845

Thr Val Phe Ser Met Gly Thr Ala Trp Gly Thr Phe Thr Trp Asn Gly
850                 855                 860

Thr Gly Gly Lys Pro Val Thr Phe Ala Val Glu Glu Met Pro Met Phe
865                 870                 875                 880

Ser Arg Tyr Thr Ile Phe Arg Leu His Phe Gly Leu Gly Gly Leu Asp
                885                 890                 895

Met Asp Lys Ile Val Phe Lys Lys Ile Arg Pro Ala Glu Ala Gln Val
                900                 905                 910

Cys Arg Leu Arg Ile Ser Glu Arg Trp Leu Gln Thr Gln Thr Tyr Phe
                915                 920                 925

Trp Leu Lys Ala Asn Phe Gln Ser Lys Lys Leu Leu Arg Gly Arg Arg
                930                 935                 940

Ala Tyr Arg
945

<210> SEQ ID NO 38
<211> LENGTH: 192
<212> TYPE: PRT
<213> ORGANISM: Schizophyllum commune

<400> SEQUENCE: 38

Glu Phe Pro Tyr Leu Ile Thr Pro Leu Asp Ala Ile Thr Ala Arg Ala
1               5                   10                  15

Gln Glu Asp Gly Thr Thr Val Thr Ser Ser Leu Ser Asp Ser Asp Thr
                20                  25                  30

Ala Arg Ala Ala Gln Ile Ala Ala Ala Asp Val Ala Ile Val Phe
                35                  40                  45

Ile Ser Ser Asp Ser Gly Glu Gly Tyr Leu Thr Val Glu Gly Asn Ala
50                  55                  60

Gly Asp Arg Asn Asp Leu Leu Ala Trp His Asp Gly Asp Ala Leu Val
65                  70                  75                  80

Gln Ala Val Ala Asp Ala Asn Glu Asn Thr Ile Val Ala Val Asn Thr
                85                  90                  95

Val Gly Ala Ile Ile Thr Glu Ala Trp Ile Glu His Pro Asn Val Lys
                100                 105                 110

Ala Val Val Trp Ser Gly Leu Pro Gly Gln Glu Ala Gly Asn Ser Val
                115                 120                 125

Ala Asp Ile Leu Tyr Gly Ala Tyr Asn Pro Ser Gly Arg Leu Pro Tyr
                130                 135                 140

Thr Ile Ala Lys Ser Ala Asp Asp Tyr Pro Ala Gln Val Leu Tyr Glu
145                 150                 155                 160

Ser Ser Ala Gln Val Pro Asp Ile Asp Tyr Ser Glu Gly Leu Leu Val
                165                 170                 175

Asp Tyr Arg His Phe Asp Ala Asn Gly Ile Glu Pro Arg Phe Glu Phe
                180                 185                 190

<210> SEQ ID NO 39
<211> LENGTH: 493
<212> TYPE: PRT
<213> ORGANISM: Trifolium repens

<400> SEQUENCE: 39

Met Asp Phe Ile Val Ala Ile Phe Ala Leu Phe Val Ile Ser Ser Phe
1               5                   10                  15

-continued

```
Thr Ile Thr Ser Thr Asn Ala Val Glu Ala Ser Thr Leu Leu Asp Ile
            20                  25                  30

Gly Asn Leu Ser Arg Ser Ser Phe Pro Arg Gly Phe Ile Phe Gly Ala
        35                  40                  45

Gly Ser Ser Ala Tyr Gln Phe Glu Gly Ala Val Asn Glu Gly Gly Arg
    50                  55                  60

Gly Pro Ser Ile Trp Asp Thr Phe Thr His Lys Tyr Pro Glu Lys Ile
65                  70                  75                  80

Arg Asp Gly Ser Asn Ala Asp Ile Thr Val Asp Gln Tyr His Arg Tyr
                85                  90                  95

Lys Glu Asp Val Gly Ile Met Lys Asp Gln Asn Met Asp Ser Tyr Arg
            100                 105                 110

Phe Ser Ile Ser Trp Pro Arg Ile Leu Pro Lys Gly Lys Leu Ser Gly
        115                 120                 125

Gly Ile Asn His Glu Gly Ile Lys Tyr Tyr Asn Asn Leu Ile Asn Glu
    130                 135                 140

Leu Leu Ala Asn Gly Ile Gln Pro Phe Val Thr Leu Phe His Trp Asp
145                 150                 155                 160

Leu Pro Gln Val Leu Glu Asp Glu Tyr Gly Gly Phe Leu Asn Ser Gly
                165                 170                 175

Val Ile Asn Asp Phe Arg Asp Tyr Thr Asp Leu Cys Phe Lys Glu Phe
            180                 185                 190

Gly Asp Arg Val Arg Tyr Trp Ser Thr Leu Asn Glu Pro Trp Val Phe
        195                 200                 205

Ser Asn Ser Gly Tyr Ala Leu Gly Thr Asn Ala Pro Gly Arg Cys Ser
    210                 215                 220

Ala Ser Asn Val Ala Lys Pro Gly Asp Ser Gly Thr Gly Pro Tyr Ile
225                 230                 235                 240

Val Thr His Asn Gln Ile Leu Ala His Ala Glu Ala Val His Val Tyr
                245                 250                 255

Lys Thr Lys Tyr Gln Ala Tyr Gln Lys Gly Lys Ile Gly Ile Thr Leu
            260                 265                 270

Val Ser Asn Trp Leu Met Pro Leu Asp Asp Asn Ser Ile Pro Asp Ile
        275                 280                 285

Lys Ala Ala Glu Arg Ser Leu Asp Phe Gln Phe Gly Leu Phe Met Glu
    290                 295                 300

Gln Leu Thr Thr Gly Asp Tyr Ser Lys Ser Met Arg Arg Ile Val Lys
305                 310                 315                 320

Asn Arg Leu Pro Lys Phe Ser Lys Phe Glu Ser Ser Leu Val Asn Gly
                325                 330                 335

Ser Phe Asp Phe Ile Gly Ile Asn Tyr Tyr Ser Ser Ser Tyr Ile Ser
            340                 345                 350

Asn Ala Pro Ser His Gly Asn Ala Lys Pro Ser Tyr Ser Thr Asn Pro
        355                 360                 365

Met Thr Asn Ile Ser Phe Glu Lys His Gly Ile Pro Leu Gly Pro Arg
    370                 375                 380

Ala Ala Ser Ile Trp Ile Tyr Val Tyr Pro Tyr Met Phe Ile Gln Glu
385                 390                 395                 400

Asp Phe Glu Ile Phe Cys Tyr Ile Leu Lys Ile Asn Ile Thr Ile Leu
                405                 410                 415

Gln Phe Ser Ile Thr Glu Asn Gly Met Asn Glu Phe Asn Asp Ala Thr
            420                 425                 430

Leu Pro Val Glu Glu Ala Leu Leu Asn Thr Tyr Arg Ile Asp Tyr Tyr
```

```
            435                 440                 445
Tyr Arg His Leu Tyr Tyr Ile Arg Ser Ala Ile Arg Ala Gly Ser Asn
        450                 455                 460

Val Lys Gly Phe Tyr Ala Trp Ser Phe Leu Asp Cys Asn Glu Trp Phe
465                 470                 475                 480

Ala Gly Phe Thr Val Arg Phe Gly Leu Asn Phe Val Asp
                    485                 490

<210> SEQ ID NO 40
<211> LENGTH: 425
<212> TYPE: PRT
<213> ORGANISM: Trifolium repens

<400> SEQUENCE: 40

Leu Leu Ser Ile Thr Thr Thr His Ile His Ala Phe Lys Pro Leu Pro
1               5                   10                  15

Ile Ser Phe Asp Asp Phe Ser Asp Leu Asn Arg Ser Cys Phe Ala Pro
                20                  25                  30

Gly Phe Val Phe Gly Thr Ala Ser Ser Ala Phe Gln Tyr Glu Gly Ala
            35                  40                  45

Ala Phe Glu Asp Gly Lys Gly Pro Ser Ile Trp Asp Thr Phe Thr His
    50                  55                  60

Lys Tyr Pro Glu Lys Ile Lys Asp Arg Thr Asn Gly Asp Val Ala Ile
65                  70                  75                  80

Asp Glu Tyr His Arg Tyr Lys Glu Asp Ile Gly Ile Met Lys Asp Met
                85                  90                  95

Asn Leu Asp Ala Tyr Arg Phe Ser Ile Ser Trp Pro Arg Val Leu Pro
            100                 105                 110

Lys Gly Lys Leu Ser Gly Gly Val Asn Arg Glu Gly Ile Asn Tyr Tyr
        115                 120                 125

Asn Asn Leu Ile Asn Glu Val Leu Ala Asn Gly Met Gln Pro Tyr Val
    130                 135                 140

Thr Leu Phe His Trp Asp Val Pro Gln Ala Leu Glu Asp Glu Tyr Arg
145                 150                 155                 160

Gly Phe Leu Gly Arg Asn Ile Val Asp Asp Phe Arg Asp Tyr Ala Glu
                165                 170                 175

Leu Cys Phe Lys Glu Phe Gly Asp Arg Val Lys His Trp Ile Thr Leu
            180                 185                 190

Asn Glu Pro Trp Gly Val Ser Met Asn Ala Tyr Ala Tyr Gly Thr Phe
        195                 200                 205

Ala Pro Gly Arg Cys Ser Asp Trp Leu Lys Leu Asn Cys Thr Gly Gly
    210                 215                 220

Asp Ser Gly Arg Glu Pro Tyr Leu Ala Ala His Tyr Gln Leu Leu Ala
225                 230                 235                 240

His Ala Ala Ala Ala Arg Leu Tyr Lys Thr Lys Tyr Gln Ala Ser Gln
                245                 250                 255

Asn Gly Ile Ile Gly Ile Thr Leu Val Ser His Trp Phe Glu Pro Ala
            260                 265                 270

Ser Lys Glu Lys Ala Asp Val Asp Ala Ala Lys Arg Gly Leu Asp Phe
        275                 280                 285

Met Leu Gly Trp Phe Met His Pro Leu Thr Lys Gly Arg Tyr Pro Glu
    290                 295                 300

Ser Met Arg Tyr Leu Val Arg Lys Arg Leu Pro Lys Phe Ser Thr Glu
305                 310                 315                 320
```

-continued

```
Glu Ser Lys Glu Leu Thr Gly Ser Phe Asp Phe Leu Gly Leu Asn Tyr
            325                 330                 335

Tyr Ser Ser Tyr Tyr Ala Ala Lys Ala Pro Arg Ile Pro Asn Ala Arg
            340                 345                 350

Pro Ala Ile Gln Thr Asp Ser Leu Ile Asn Ala Thr Phe Glu His Asn
            355                 360                 365

Gly Lys Pro Leu Gly Pro Met Ala Ala Ser Ser Trp Leu Cys Ile Tyr
            370                 375                 380

Pro Gln Gly Ile Arg Lys Leu Leu Leu Tyr Val Lys Asn His Tyr Asn
385                 390                 395                 400

Asn Pro Val Ile Tyr Ile Thr Glu Asn Gly Arg Asn Ser Ser Thr Ile
                405                 410                 415

Asn Thr Val Thr Ser Arg Ile Pro Phe
            420                 425

<210> SEQ ID NO 41
<211> LENGTH: 765
<212> TYPE: PRT
<213> ORGANISM: Escherichia coli

<400> SEQUENCE: 41

Met Lys Trp Leu Cys Ser Val Gly Ile Ala Val Ser Leu Ala Leu Gln
1               5                   10                  15

Pro Ala Leu Ala Asp Asp Leu Phe Gly Asn His Pro Leu Thr Pro Glu
            20                  25                  30

Ala Arg Asp Ala Phe Val Thr Glu Leu Leu Lys Lys Met Thr Val Asp
            35                  40                  45

Glu Lys Ile Gly Gln Leu Arg Leu Ile Ser Val Gly Pro Asp Asn Pro
50                  55                  60

Lys Glu Ala Ile Arg Glu Met Ile Lys Asp Gly Gln Val Gly Ala Ile
65                  70                  75                  80

Phe Asn Thr Val Thr Arg Gln Asp Ile Arg Ala Met Gln Asp Gln Val
                85                  90                  95

Met Glu Leu Ser Arg Leu Lys Ile Pro Leu Phe Phe Ala Tyr Asp Val
            100                 105                 110

Leu His Gly Gln Arg Thr Val Phe Pro Ile Ser Leu Gly Leu Ala Ser
            115                 120                 125

Ser Phe Asn Leu Asp Ala Val Lys Thr Val Gly Arg Val Ser Ala Tyr
            130                 135                 140

Glu Ala Ala Asp Asp Gly Leu Asn Met Thr Trp Ala Pro Met Val Asp
145                 150                 155                 160

Val Ser Arg Asp Pro Arg Trp Gly Arg Ala Ser Glu Gly Phe Gly Glu
                165                 170                 175

Asp Thr Tyr Leu Thr Ser Thr Met Gly Lys Thr Met Val Glu Ala Met
            180                 185                 190

Gln Gly Lys Ser Pro Ala Asp Arg Tyr Ser Val Met Thr Ser Val Lys
            195                 200                 205

His Phe Ala Ala Tyr Gly Ala Val Glu Gly Gly Lys Glu Tyr Asn Thr
            210                 215                 220

Val Asp Met Ser Pro Gln Arg Leu Phe Asn Asp Tyr Met Pro Pro Tyr
225                 230                 235                 240

Lys Ala Gly Leu Asp Ala Gly Ser Gly Ala Val Met Val Ala Leu Asn
                245                 250                 255

Ser Leu Asn Gly Thr Pro Ala Thr Ser Asp Ser Trp Leu Leu Lys Asp
            260                 265                 270
```

```
Val Leu Arg Asp Gln Trp Gly Phe Lys Gly Ile Thr Val Ser Asp His
        275                 280                 285
Gly Ala Ile Lys Glu Leu Ile Lys His Gly Thr Ala Ala Asp Pro Glu
        290                 295                 300
Asp Ala Val Arg Val Ala Leu Lys Ser Gly Ile Asn Met Ser Met Ser
305                 310                 315                 320
Asp Glu Tyr Tyr Ser Lys Tyr Leu Pro Gly Leu Ile Lys Ser Gly Lys
                325                 330                 335
Val Thr Met Ala Glu Leu Asp Asp Ala Ala Arg His Val Leu Asn Val
                    340                 345                 350
Lys Tyr Asp Met Gly Leu Phe Asn Asp Pro Tyr Ser His Leu Gly Pro
                355                 360                 365
Lys Glu Ser Asp Pro Val Asp Thr Asn Ala Glu Ser Arg Leu His Arg
            370                 375                 380
Lys Glu Ala Arg Glu Val Ala Arg Glu Ser Leu Val Leu Leu Lys Asn
385                 390                 395                 400
Arg Leu Glu Thr Leu Pro Leu Lys Lys Ser Ala Thr Ile Ala Val Val
                405                 410                 415
Gly Pro Leu Ala Asp Ser Lys Arg Asp Val Met Gly Ser Trp Ser Ala
                420                 425                 430
Ala Gly Val Ala Asp Gln Ser Val Thr Val Leu Thr Gly Ile Lys Asn
                435                 440                 445
Ala Val Gly Glu Asn Gly Lys Val Leu Tyr Ala Lys Gly Ala Asn Val
        450                 455                 460
Thr Ser Asp Lys Gly Ile Ile Asp Phe Leu Asn Gln Tyr Glu Glu Ala
465                 470                 475                 480
Val Lys Val Asp Pro Arg Ser Pro Gln Glu Met Ile Asp Glu Ala Val
                485                 490                 495
Gln Thr Ala Lys Gln Ser Asp Val Val Val Ala Val Val Gly Glu Ala
                500                 505                 510
Gln Gly Met Ala His Glu Ala Ser Ser Arg Thr Asp Ile Thr Ile Pro
            515                 520                 525
Gln Ser Gln Arg Asp Leu Ile Ala Ala Leu Lys Ala Thr Gly Lys Pro
        530                 535                 540
Leu Val Leu Val Leu Met Asn Gly Arg Pro Leu Ala Leu Val Lys Glu
545                 550                 555                 560
Asp Gln Gln Ala Asp Ala Ile Leu Glu Thr Trp Phe Ala Gly Thr Glu
                565                 570                 575
Gly Gly Asn Ala Ile Ala Asp Val Leu Phe Gly Asp Tyr Asn Pro Ser
                580                 585                 590
Gly Lys Leu Pro Met Ser Phe Pro Arg Ser Val Gly Gln Ile Pro Val
            595                 600                 605
Tyr Tyr Ser His Leu Asn Thr Gly Arg Pro Tyr Asn Ala Asp Lys Pro
        610                 615                 620
Asn Lys Tyr Thr Ser Arg Tyr Phe Asp Glu Ala Asn Gly Ala Leu Tyr
625                 630                 635                 640
Pro Phe Gly Tyr Gly Leu Ser Tyr Thr Thr Phe Thr Val Ser Asp Val
                645                 650                 655
Lys Leu Ser Ala Pro Thr Met Lys Arg Asp Gly Lys Val Thr Ala Ser
                660                 665                 670
Val Gln Val Thr Asn Thr Gly Lys Arg Glu Gly Ala Thr Val Val Gln
            675                 680                 685
```

```
Met Tyr Leu Gln Asp Val Thr Ala Ser Met Ser Arg Pro Val Lys Gln
        690                 695                 700
Leu Lys Gly Phe Glu Lys Ile Thr Leu Lys Pro Gly Glu Thr Gln Thr
705                 710                 715                 720
Val Ser Phe Pro Ile Asp Ile Glu Ala Leu Lys Phe Trp Asn Gln Gln
                    725                 730                 735
Met Lys Tyr Asp Ala Glu Pro Gly Lys Phe Asn Val Phe Ile Gly Thr
                740                 745                 750
Asp Ser Ala Arg Val Lys Lys Gly Glu Phe Glu Leu Leu
                755                 760                 765

<210> SEQ ID NO 42
<211> LENGTH: 654
<212> TYPE: PRT
<213> ORGANISM: Erwinia chrysanthemi

<400> SEQUENCE: 42

Met Glu Lys Ser Ala Thr Arg Gln Lys Ala Leu Leu Ile Ala Leu Pro
1               5                   10                  15
Leu Leu Phe Ser Pro Leu Ala Ser Ala Val Gln Gln Ala Val Leu Asp
                20                  25                  30
Thr Arg Gly Ala Pro Leu Ile Thr Val Asn Gly Leu Thr Phe Lys Asp
            35                  40                  45
Leu Asn Arg Asp Gly Lys Leu Asn Pro Tyr Glu Asp Trp Arg Leu Pro
        50                  55                  60
Ala Ala Glu Arg Ala Ala Asp Leu Val Ser Arg Met Thr Leu Ala Glu
65                  70                  75                  80
Lys Ala Gly Val Met Met His Gly Ser Ala Pro Thr Ala Gly Ser Val
                85                  90                  95
Thr Gly Ala Gly Thr Gln Tyr Asp Leu Asn Ala Ala Lys Thr Met Ile
            100                 105                 110
Ala Asp Arg Tyr Val Asn Ser Phe Ile Thr Arg Leu Ser Gly Asp Asn
        115                 120                 125
Pro Ala Gln Met Ala Glu Glu Asn Asn Lys Leu Gln Gln Leu Ala Glu
    130                 135                 140
Ala Thr Arg Leu Gly Ile Pro Leu Thr Ile Ser Thr Asp Pro Arg Ser
145                 150                 155                 160
Ser Phe Gln Ser Leu Val Gly Val Ser Val Gly Lys Phe Ser
                165                 170                 175
Lys Trp Pro Glu Thr Leu Gly Leu Ala Ala Ile Gly Asp Glu Glu Leu
            180                 185                 190
Val Arg Arg Phe Ala Asp Ile Val Arg Gln Glu Tyr Arg Ala Val Gly
        195                 200                 205
Ile Thr Glu Ala Leu Ser Pro Gln Ala Asp Leu Ala Thr Glu Pro Arg
    210                 215                 220
Trp Pro Arg Ile Asp Gly Thr Phe Gly Glu Asp Pro Asp Leu Thr Lys
225                 230                 235                 240
Lys Met Val Arg Gly Tyr Val Thr Gly Met Gln Asn Gly Lys Asn Gly
                245                 250                 255
Leu Asn Ala Gln Ser Val Ile Ser Ile Val Lys His Trp Val Gly Tyr
            260                 265                 270
Gly Ala Ala Lys Asp Gly Trp Asp Ser His Asn Val Tyr Gly Lys Tyr
        275                 280                 285
Ala Gln Phe Arg Gln Asn Asn Leu Gln Trp His Ile Asp Pro Phe Thr
    290                 295                 300
```

```
Gly Ala Phe Glu Ala His Ala Ala Gly Ile Met Pro Thr Tyr Ser Ile
305                 310                 315                 320

Leu Arg Asn Ala Ser Trp His Gly Lys Pro Ile Glu Gln Val Gly Ala
            325                 330                 335

Gly Phe Asn Arg Phe Leu Leu Thr Asp Leu Leu Arg Gly Gln Tyr Gly
            340                 345                 350

Phe Asp Gly Val Ile Leu Ser Asp Trp Leu Ile Thr Asn Asp Cys Lys
            355                 360                 365

Gly Asp Cys Leu Thr Gly Val Lys Pro Gly Glu Lys Pro Val Pro Arg
    370                 375                 380

Gly Met Pro Trp Gly Val Glu Lys Leu Thr Pro Ala Glu Arg Phe Val
385                 390                 395                 400

Lys Ala Val Asn Ala Gly Val Asp Gln Phe Gly Gly Val Thr Asp Ser
                405                 410                 415

Ala Leu Leu Val Gln Ala Val Gln Asp Gly Lys Leu Thr Glu Ala Arg
            420                 425                 430

Leu Asp Thr Ser Val Asn Arg Ile Leu Lys Gln Lys Phe Gln Thr Gly
            435                 440                 445

Leu Phe Glu Arg Pro Tyr Val Asn Ala Thr Gln Ala Asn Asp Ile Val
450                 455                 460

Gly Arg Ala Asp Trp Gln Gln Leu Ala Asp Thr Gln Ala Arg Ser
465                 470                 475                 480

Leu Val Leu Leu Gln Asn Asn Asn Leu Leu Pro Leu Arg Lys Gly Ser
            485                 490                 495

Arg Val Trp Leu His Gly Ile Ala Ala Asn Ala Ala Gln Glu Val Gly
                500                 505                 510

Phe Ile Val Val Asn Thr Pro Glu Gln Ala Asp Val Ala Leu Ile Arg
            515                 520                 525

Thr His Thr Pro Tyr Glu Gln Pro His Lys Asn Phe Phe Gly Ser
            530                 535                 540

Arg His His Glu Gly Ser Leu Ala Phe Arg Asn Asp Asn Pro Asp Tyr
545                 550                 555                 560

Gln Ala Ile Val Arg Ala Ser Ala Lys Val Pro Thr Leu Val Thr Val
                565                 570                 575

Tyr Met Glu Arg Pro Ala Ile Leu Thr Asn Val Val Asp Lys Thr Arg
            580                 585                 590

Ala Val Val Ala Asn Phe Gly Val Ser Asp Ser Val Leu Leu Asn Arg
            595                 600                 605

Leu Met Ser Gly Ala Ala Tyr Thr Ala Lys Leu Pro Phe Glu Leu Pro
            610                 615                 620

Ser Ser Met Ser Ala Val Arg Asn Gln Gln Pro Asp Leu Pro Tyr Asp
625                 630                 635                 640

Ser Ala Lys Pro Leu Phe Pro Phe Gly Tyr Gly Leu Pro His
                645                 650

<210> SEQ ID NO 43
<211> LENGTH: 765
<212> TYPE: PRT
<213> ORGANISM: Salmonella typhimurium

<400> SEQUENCE: 43

Met Lys Trp Leu Cys Ser Val Gly Val Ala Val Ser Leu Ala Met Gln
1               5                   10                  15

Pro Ala Leu Ala Glu Asn Leu Phe Gly Asn His Pro Leu Thr Pro Glu
```

-continued

```
            20                  25                  30
Ala Arg Asp Ala Phe Val Thr Asp Leu Leu Lys Lys Met Thr Val Asp
            35                  40                  45
Glu Lys Ile Gly Gln Leu Arg Leu Ile Ser Val Gly Pro Asp Asn Pro
50                  55                  60
Lys Glu Ala Ile Arg Glu Met Ile Lys Asp Gly Gln Val Gly Ala Ile
65                  70                  75                  80
Phe Asn Thr Val Thr Arg Gln Asp Ile Arg Gln Met Gln Asp Gln Val
                85                  90                  95
Met Ala Leu Ser Arg Leu Lys Ile Pro Leu Phe Phe Ala Tyr Asp Val
                100                 105                 110
Val His Gly Gln Arg Thr Val Phe Pro Ile Ser Leu Gly Leu Ala Ser
            115                 120                 125
Ser Phe Asn Leu Asp Ala Val Arg Thr Val Gly Arg Val Ser Ala Tyr
            130                 135                 140
Glu Ala Ala Asp Asp Gly Leu Asn Met Thr Trp Ala Pro Met Val Asp
145                 150                 155                 160
Val Ser Arg Asp Pro Arg Trp Gly Arg Ala Ser Glu Gly Phe Gly Glu
                165                 170                 175
Asp Thr Tyr Leu Thr Ser Ile Met Gly Glu Thr Met Val Lys Ala Met
                180                 185                 190
Gln Gly Lys Ser Pro Ala Asp Arg Tyr Ser Val Met Thr Ser Val Lys
            195                 200                 205
His Phe Ala Ala Tyr Gly Ala Val Glu Gly Gly Lys Glu Tyr Asn Thr
            210                 215                 220
Val Asp Met Ser Ser Gln Arg Leu Phe Asn Asp Tyr Met Pro Pro Tyr
225                 230                 235                 240
Lys Ala Gly Leu Asp Ala Gly Ser Gly Ala Val Met Val Ala Leu Asn
                245                 250                 255
Ser Leu Asn Gly Thr Pro Ala Thr Ser Asp Ser Trp Leu Leu Lys Asp
                260                 265                 270
Val Leu Arg Asp Glu Trp Gly Phe Lys Gly Ile Thr Val Ser Asp His
            275                 280                 285
Gly Ala Ile Lys Glu Leu Ile Lys His Gly Thr Ala Ala Asp Pro Glu
            290                 295                 300
Asp Ala Val Arg Val Ala Leu Lys Ala Gly Val Asp Met Ser Met Ala
305                 310                 315                 320
Asp Glu Tyr Tyr Ser Lys Tyr Leu Pro Gly Leu Ile Lys Ser Gly Lys
                325                 330                 335
Val Thr Met Ala Glu Leu Asp Asp Ala Thr Arg His Val Leu Asn Val
                340                 345                 350
Lys Tyr Asp Met Gly Leu Phe Asn Asp Pro Tyr Ser His Leu Gly Pro
            355                 360                 365
Lys Glu Ser Asp Pro Val Asp Thr Asn Ala Glu Ser Arg Leu His Arg
            370                 375                 380
Lys Glu Ala Arg Glu Val Ala Arg Glu Ser Val Val Leu Leu Lys Asn
385                 390                 395                 400
Arg Leu Glu Thr Leu Pro Leu Lys Lys Ser Gly Thr Ile Ala Val Val
                405                 410                 415
Gly Pro Leu Ala Asp Ser Gln Arg Asp Val Met Gly Ser Trp Ser Ala
                420                 425                 430
Ala Gly Val Ala Asn Gln Ser Val Thr Val Leu Ala Gly Ile Gln Asn
            435                 440                 445
```

```
Ala Val Gly Asp Gly Ala Lys Ile Leu Tyr Ala Lys Gly Ala Asn Ile
        450                 455                 460
Thr Asn Asp Lys Gly Ile Val Asp Phe Leu Asn Leu Tyr Glu Glu Ala
465                 470                 475                 480
Val Lys Ile Asp Pro Arg Ser Pro Gln Ala Met Ile Asp Glu Ala Val
                485                 490                 495
Gln Ala Ala Lys Gln Ala Asp Val Val Ala Val Val Gly Glu Ser
            500                 505                 510
Gln Gly Met Ala His Glu Ala Ser Ser Arg Thr Asn Ile Thr Ile Pro
        515                 520                 525
Gln Ser Gln Arg Asp Leu Ile Thr Ala Leu Lys Ala Thr Gly Lys Pro
        530                 535                 540
Leu Val Leu Val Leu Met Asn Gly Arg Pro Leu Ala Leu Val Lys Glu
545                 550                 555                 560
Asp Gln Gln Ala Asp Ala Ile Leu Glu Thr Trp Phe Ala Gly Thr Glu
                565                 570                 575
Gly Gly Asn Ala Ile Ala Asp Val Leu Phe Gly Asp Tyr Asn Pro Ser
            580                 585                 590
Gly Lys Leu Pro Ile Ser Phe Pro Arg Ser Val Gly Gln Ile Pro Val
            595                 600                 605
Tyr Tyr Ser His Leu Asn Thr Gly Arg Pro Tyr Asn Pro Glu Lys Pro
        610                 615                 620
Asn Lys Tyr Thr Ser Arg Tyr Phe Asp Glu Ala Asn Gly Pro Leu Tyr
625                 630                 635                 640
Pro Phe Gly Tyr Gly Leu Ser Tyr Thr Thr Phe Thr Val Ser Asp Val
                645                 650                 655
Thr Leu Ser Ser Pro Thr Met Gln Arg Asp Gly Lys Val Thr Ala Ser
            660                 665                 670
Val Glu Val Thr Asn Thr Gly Lys Arg Glu Gly Ala Thr Val Ile Gln
            675                 680                 685
Met Tyr Leu Gln Asp Val Thr Ala Ser Met Ser Arg Pro Val Lys Gln
        690                 695                 700
Leu Lys Gly Phe Glu Lys Ile Thr Leu Lys Pro Gly Glu Arg Lys Thr
705                 710                 715                 720
Val Ser Phe Pro Ile Asp Ile Glu Ala Leu Lys Phe Trp Asn Gln Gln
                725                 730                 735
Met Lys Tyr Asp Ala Glu Pro Gly Lys Phe Asn Val Phe Ile Gly Val
            740                 745                 750
Asp Ser Ala Arg Val Lys Gln Gly Ser Phe Glu Leu Leu
        755                 760                 765

<210> SEQ ID NO 44
<211> LENGTH: 469
<212> TYPE: PRT
<213> ORGANISM: Cavia porcellus

<400> SEQUENCE: 44

Met Ala Phe Pro Ala Asp Leu Val Gly Gly Leu Pro Thr Ala Ala Tyr
1               5                   10                  15
Gln Val Glu Gly Gly Trp Asp Ala Asp Gly Arg Gly Pro Cys Val Trp
            20                  25                  30
Asp Thr Phe Thr His Gln Gly Gly Glu Arg Val Phe Lys Asn Gln Thr
        35                  40                  45
Gly Asp Val Ala Cys Gly Ser Tyr Thr Leu Trp Glu Glu Asp Leu Lys
```

```
                50                  55                  60
Cys Ile Lys Gln Leu Gly Leu Thr His Tyr Arg Phe Ser Ile Ser Trp
 65                  70                  75                  80

Ser Arg Leu Leu Pro Asp Gly Thr Thr Gly Phe Ile Asn Gln Lys Gly
                 85                  90                  95

Val Asp Tyr Tyr Asn Lys Ile Ile Asp Leu Leu Thr Asn Gly Val
                100                 105                 110

Thr Pro Val Val Thr Leu Tyr His Phe Asp Leu Pro Gln Ala Leu Glu
                115                 120                 125

Asp Gln Gly Gly Trp Leu Ser Glu Ala Ile Ile Glu Val Phe Asp Lys
            130                 135                 140

Tyr Ala Gln Phe Cys Phe Ser Thr Phe Gly Asn Arg Val Arg Gln Trp
145                 150                 155                 160

Ile Thr Ile Asn Glu Pro Asn Val Leu Cys Ala Met Gly Tyr Asp Leu
                165                 170                 175

Gly Phe Phe Ala Pro Gly Val Ser Gln Ile Gly Thr Gly Gly Tyr Gln
                180                 185                 190

Ala Ala His Asn Met Ile Lys Ala His Ala Arg Ala Trp His Ser Tyr
            195                 200                 205

Asp Ser Leu Phe Arg Glu Lys Gln Lys Gly Met Val Ser Leu Ser Leu
210                 215                 220

Phe Cys Ile Trp Pro Gln Pro Glu Asn Pro Asn Ser Val Leu Asp Gln
225                 230                 235                 240

Lys Ala Ala Glu Arg Ala Ile Asn Phe Gln Phe Asp Phe Phe Ala Lys
                245                 250                 255

Pro Ile Phe Ile Asp Gly Asp Tyr Pro Glu Leu Val Lys Ser Gln Ile
                260                 265                 270

Ala Ser Met Ser Glu Lys Gln Gly Tyr Pro Ser Ser Arg Leu Ser Lys
            275                 280                 285

Phe Thr Glu Glu Glu Lys Lys Met Ile Lys Gly Thr Ala Asp Phe Phe
290                 295                 300

Ala Val Gln Tyr Tyr Thr Thr Arg Phe Ile Arg His Lys Glu Asn Lys
305                 310                 315                 320

Glu Ala Glu Leu Gly Ile Leu Gln Asp Ala Glu Ile Glu Leu Phe Ser
                325                 330                 335

Asp Pro Ser Trp Lys Gly Val Trp Val Arg Val Pro Trp Gly
                340                 345                 350

Ile Arg Lys Leu Leu Asn Tyr Ile Lys Asp Thr Tyr Asn Asn Pro Val
            355                 360                 365

Ile Tyr Ile Thr Glu Asn Gly Phe Pro Gln Asp Pro Pro Ser Ile
370                 375                 380

Asp Asp Thr Gln Arg Trp Glu Cys Phe Arg Gln Thr Phe Glu Glu Leu
385                 390                 395                 400

Phe Lys Ala Ile His Val Asp Lys Val Asn Leu Gln Leu Tyr Cys Ala
                405                 410                 415

Trp Ser Leu Leu Asp Asn Phe Glu Trp Asn Asp Gly Tyr Ser Lys Arg
                420                 425                 430

Phe Gly Leu Phe His Val Asp Phe Glu Asp Pro Ala Lys Pro Arg Val
            435                 440                 445

Pro Tyr Thr Ser Ala Lys Glu Tyr Ala Lys Ile Ile Arg Asn Asn Gly
450                 455                 460

Leu Glu Arg Pro Gln
465
```

<210> SEQ ID NO 45
<211> LENGTH: 469
<212> TYPE: PRT
<213> ORGANISM: Homo sapiens

<400> SEQUENCE: 45

```
Met Ala Phe Pro Ala Gly Phe Gly Trp Ala Ala Thr Ala Ala Tyr
1               5                   10                  15

Gln Val Glu Gly Gly Trp Asp Ala Asp Gly Lys Gly Pro Cys Val Trp
            20                  25                  30

Asp Thr Phe Thr His Gln Gly Gly Glu Arg Val Phe Lys Asn Gln Thr
            35                  40                  45

Gly Asp Val Ala Cys Gly Ser Tyr Thr Leu Trp Glu Glu Asp Leu Lys
        50                  55                  60

Cys Ile Lys Gln Leu Gly Leu Thr His Tyr Arg Phe Ser Leu Ser Trp
65                  70                  75                  80

Ser Arg Leu Leu Pro Asp Gly Thr Thr Gly Phe Ile Asn Gln Lys Gly
                85                  90                  95

Ile Asp Tyr Tyr Asn Lys Ile Ile Asp Asp Leu Leu Lys Asn Gly Val
            100                 105                 110

Thr Pro Ile Val Thr Leu Tyr His Phe Asp Leu Pro Gln Thr Leu Glu
        115                 120                 125

Asp Gln Gly Gly Trp Leu Ser Glu Ala Ile Ile Glu Ser Phe Asp Lys
    130                 135                 140

Tyr Ala Gln Phe Cys Phe Ser Thr Phe Gly Asp Arg Val Lys Gln Trp
145                 150                 155                 160

Ile Thr Ile Asn Glu Ala Asn Val Leu Ser Val Met Ser Tyr Asp Leu
                165                 170                 175

Gly Met Phe Pro Pro Gly Ile Pro His Phe Gly Thr Gly Gly Tyr Gln
            180                 185                 190

Ala Ala His Asn Leu Ile Lys Ala His Ala Arg Ser Trp His Ser Tyr
        195                 200                 205

Asp Ser Leu Phe Arg Lys Lys Gln Lys Gly Met Val Ser Leu Ser Leu
    210                 215                 220

Phe Ala Val Trp Leu Glu Pro Ala Asp Pro Asn Ser Val Ser Asp Gln
225                 230                 235                 240

Glu Ala Ala Lys Arg Ala Ile Thr Phe His Leu Asp Leu Phe Ala Lys
                245                 250                 255

Pro Ile Phe Ile Asp Gly Asp Tyr Pro Glu Val Val Lys Ser Gln Ile
            260                 265                 270

Ala Ser Met Ser Gln Lys Gln Gly Tyr Pro Ser Ser Arg Leu Pro Glu
        275                 280                 285

Phe Thr Glu Glu Glu Lys Lys Met Ile Lys Gly Thr Ala Asp Phe Phe
    290                 295                 300

Ala Val Gln Tyr Tyr Thr Thr Arg Leu Ile Lys Tyr Gln Glu Asn Lys
305                 310                 315                 320

Lys Gly Glu Leu Gly Ile Leu Gln Asp Ala Glu Ile Glu Phe Phe Pro
                325                 330                 335

Asp Pro Ser Trp Lys Asn Val Asp Trp Ile Tyr Val Val Pro Trp Gly
            340                 345                 350

Val Cys Lys Leu Leu Lys Tyr Ile Lys Asp Thr Tyr Asn Asn Pro Val
        355                 360                 365

Ile Tyr Ile Thr Glu Asn Gly Phe Pro Gln Ser Asp Pro Ala Pro Leu
```

```
                370                 375                 380
Asp Asp Thr Gln Arg Trp Glu Tyr Phe Arg Gln Thr Phe Gln Glu Leu
385                 390                 395                 400

Phe Lys Ala Ile Gln Leu Asp Lys Val Asn Leu Gln Val Tyr Cys Ala
                405                 410                 415

Trp Ser Leu Leu Asp Asn Phe Glu Trp Asn Gln Gly Tyr Ser Ser Arg
                420                 425                 430

Phe Gly Leu Phe His Val Asp Phe Glu Asp Pro Ala Arg Pro Arg Val
                435                 440                 445

Pro Tyr Thr Ser Ala Lys Glu Tyr Ala Lys Ile Ile Arg Asn Asn Gly
                450                 455                 460

Leu Glu Ala His Leu
465

<210> SEQ ID NO 46
<211> LENGTH: 469
<212> TYPE: PRT
<213> ORGANISM: Pongo pygmaeus

<400> SEQUENCE: 46

Met Ala Phe Pro Val Gly Phe Gly Trp Ala Ala Thr Ala Ala Tyr
1               5                   10                  15

Gln Val Glu Gly Gly Trp Asp Ala Asp Gly Lys Gly Pro Cys Val Trp
                20                  25                  30

Asp Thr Phe Thr His Gln Gly Gly Glu Arg Val Phe Lys Asn Gln Thr
                35                  40                  45

Gly Asp Val Ala Cys Gly Ser Tyr Thr Leu Trp Glu Glu Asp Leu Lys
50                  55                  60

Cys Ile Lys Gln Leu Gly Leu Thr His Tyr Arg Phe Ser Leu Ser Trp
65                  70                  75                  80

Ser Arg Leu Leu Pro Asp Gly Thr Thr Gly Phe Ile Asn Gln Lys Gly
                85                  90                  95

Ile Asp Tyr Tyr Asn Lys Ile Ile Asp Asp Leu Leu Lys Asn Gly Val
                100                 105                 110

Thr Pro Ile Val Thr Leu Tyr His Phe Asp Leu Pro Gln Ala Leu Glu
                115                 120                 125

Asp Gln Gly Gly Trp Leu Ser Glu Ala Ile Ile Glu Ser Phe Asp Lys
130                 135                 140

Tyr Ala Gln Phe Cys Phe Ser Thr Phe Gly Asp Arg Val Lys Lys Trp
145                 150                 155                 160

Ile Thr Ile Asn Glu Ala Asn Val Leu Ser Val Met Ser Tyr Asp Leu
                165                 170                 175

Gly Met Phe Pro Pro Gly Ile Pro His Phe Gly Thr Gly Gly Tyr Gln
                180                 185                 190

Ala Ala His Asn Leu Ile Lys Ala His Ala Arg Ser Trp His Ser Tyr
                195                 200                 205

Asn Ser Leu Phe Arg Lys Glu Gln Lys Gly Met Val Ser Leu Ser Leu
                210                 215                 220

Phe Ala Val Trp Leu Glu Pro Ala Asp Pro Asn Ser Val Ser Asp Gln
225                 230                 235                 240

Glu Ala Ala Lys Arg Ala Ile Thr Phe His Leu Asp Leu Phe Ala Lys
                245                 250                 255

Pro Ile Phe Ile Asp Gly Asp Tyr Pro Glu Ile Val Lys Ser Gln Ile
                260                 265                 270
```

-continued

```
Ala Ser Met Ser Gln Lys Gln Gly Tyr Pro Ser Ser Arg Leu Pro Glu
        275                 280                 285

Phe Thr Glu Glu Glu Lys Lys Met Ile Lys Gly Thr Ala Asp Phe Phe
    290                 295                 300

Ala Val Gln Tyr Tyr Thr Thr Arg Leu Ile Lys Tyr Gln Glu Asn Lys
305                 310                 315                 320

Lys Gly Glu Leu Gly Ile Leu Gln Asp Ala Glu Ile Glu Phe Phe Pro
                325                 330                 335

Asp Pro Ser Trp Lys Asn Val Asp Trp Ile Tyr Val Val Pro Trp Gly
            340                 345                 350

Val Arg Lys Leu Leu Lys Tyr Ile Lys Asp Thr Tyr Asn Asn Pro Val
        355                 360                 365

Ile Tyr Ile Thr Glu Asn Gly Phe Pro Gln Ser Asp Pro Ala Pro Leu
    370                 375                 380

Asp Asp Thr Gln Arg Trp Glu Tyr Phe Arg Gln Thr Phe Gln Glu Leu
385                 390                 395                 400

Phe Lys Ala Ile Gln Leu Asp Lys Val Asn Leu Gln Val Tyr Cys Ala
                405                 410                 415

Trp Ser Leu Leu Asp Asn Phe Glu Trp Asn Gln Gly Tyr Ser Ser Arg
            420                 425                 430

Phe Gly Leu Phe His Val Asp Phe Glu Asp Pro Ala Arg Pro Arg Val
        435                 440                 445

Pro Tyr Thr Ser Ala Lys Glu Tyr Ala Lys Val Ile Arg Asn Asn Gly
    450                 455                 460

Leu Glu Ala His Leu
465
```

```
<210> SEQ ID NO 47
<211> LENGTH: 918
<212> TYPE: DNA
<213> ORGANISM: Ajellomyces capsulatus

<400> SEQUENCE: 47
atgattacca ggctgatcgg gaacgagcga gatgatgaag caagggccat attggtcaaa      60
taccacgcaa acggtgactc caaccatccg ctggttaaac ttgaaatggc cgaaatggtc     120
gaatctctga gaaaagaagg catgttgact tggcggaact tttttgatct ccgggttctc     180
tttaagtctc gttcccgtcg atataggatg atgctcaatg tctccttttc gtggtttggg     240
caattctccg gtaacaacat tgcatcttat tacctacctt acctccttga aaacgttgga     300
gtagccgata ccaacaccaa gctcctcctc aacatcattt atgccatcac aggctggatc     360
ccagcaatgg ctggggcacg ctgccacgat ataatcgggc ggcgcaagat gttgctaggc     420
tgtaccgtgg gcatggcagt ctgtcttgca attgctgcag gtacggctgc cggctacatc     480
aacactggaa gcagatcgtc ctcatccgcc tcgatcgcat ttatctattt atttggctcg     540
gtgtttgcgt tcgcgttcac ctcgatgcaa ccagtgtatc ccggggaggt tatgtcaaat     600
gatatgagag gcaagggcat gggcgtttcc cagcttactt ctggcctagc gggctttgtc     660
aacacctttg cggcaccagt tgcgttaaag aatatcagat attggttcta tgtattcttc     720
gtcttttggg acctgttcga gtttgcgttt atctacttct tctacgtgga aacgaaggga     780
cgcacgctgg aagaacttga tgaggtgttt gaagcgccta atccgcgcaa agctagtacg     840
acccctatag cattgcggcg gcaacttccc gttggccaaa ttgacgaaga agagccgaag     900
cacgagactg ttgtttag                                                   918
```

<210> SEQ ID NO 48
<211> LENGTH: 305
<212> TYPE: PRT
<213> ORGANISM: Ajellomyces capsulatus

<400> SEQUENCE: 48

```
Met Ile Thr Arg Leu Ile Gly Asn Glu Arg Asp Asp Glu Ala Arg Ala
1               5                   10                  15

Ile Leu Val Lys Tyr His Ala Asn Gly Asp Ser Asn His Pro Leu Val
            20                  25                  30

Lys Leu Glu Met Ala Glu Met Val Glu Ser Leu Arg Lys Glu Gly Met
        35                  40                  45

Leu Thr Trp Arg Asn Phe Phe Asp Leu Arg Val Leu Phe Lys Ser Arg
    50                  55                  60

Ser Arg Arg Tyr Arg Met Met Leu Asn Val Ser Phe Ser Trp Phe Gly
65                  70                  75                  80

Gln Phe Ser Gly Asn Asn Ile Ala Ser Tyr Tyr Leu Pro Tyr Leu Leu
                85                  90                  95

Glu Asn Val Gly Val Ala Asp Thr Asn Thr Lys Leu Leu Leu Asn Ile
            100                 105                 110

Ile Tyr Ala Ile Thr Gly Trp Ile Pro Ala Met Ala Gly Ala Arg Cys
        115                 120                 125

His Asp Ile Ile Gly Arg Arg Lys Met Leu Leu Gly Cys Thr Val Gly
    130                 135                 140

Met Ala Val Cys Leu Ala Ile Ala Ala Gly Thr Ala Ala Gly Tyr Ile
145                 150                 155                 160

Asn Thr Gly Ser Arg Ser Ser Ser Ser Ala Ser Ile Ala Phe Ile Tyr
                165                 170                 175

Leu Phe Gly Ser Val Phe Ala Phe Ala Phe Thr Ser Met Gln Pro Val
            180                 185                 190

Tyr Pro Gly Glu Val Met Ser Asn Asp Met Arg Gly Lys Gly Met Gly
        195                 200                 205

Val Ser Gln Leu Thr Ser Gly Leu Ala Gly Phe Val Asn Thr Phe Ala
    210                 215                 220

Ala Pro Val Ala Leu Lys Asn Ile Arg Tyr Trp Phe Tyr Val Phe Phe
225                 230                 235                 240

Val Phe Trp Asp Leu Phe Glu Phe Ala Phe Ile Tyr Phe Phe Tyr Val
                245                 250                 255

Glu Thr Lys Gly Arg Thr Leu Glu Glu Leu Asp Glu Val Phe Glu Ala
            260                 265                 270

Pro Asn Pro Arg Lys Ala Ser Thr Thr Pro Ile Ala Leu Arg Arg Gln
        275                 280                 285

Leu Pro Val Gly Gln Ile Asp Glu Glu Glu Pro Lys His Glu Thr Val
    290                 295                 300

Val
305
```

<210> SEQ ID NO 49
<211> LENGTH: 1674
<212> TYPE: DNA
<213> ORGANISM: Neosartorya fischeri

<400> SEQUENCE: 49

```
atgtcgtcga ccgatgagaa gcacggcatc tcggtagagc atggctcgcc cggctccgat      60
accgacacca agcctgccgt gcctgttggt catggcgagg cggccaaggt cgacggtgcg     120
```

```
aagacgagga aggtttacaa cgccgagttg tatgccgcca tcaacgacac tcctatcccc    180
agatggagca aggagtcgat ccacttgtac ttctgcatct tcgtcgcctt ctgctgtgct    240
tgtgccaacg gttacgatgg ttcgctcatg ggagccattc tcgccatgaa acactaccag    300
aataccttcc acaccggttt ggcgggcccc aaggtctccc tggtgacctc actctatact    360
gttggttcca tcgccgcgac ccccttagt gccgttattt ccgacaggct cggtcgccgc     420
aagtgtatgt tcgtaggcgc ttggatcatt atcgccggta ccatcattat cgcgactgcg    480
aaccatcttc cccagttcta cgtcggccgc gtggttcttg gtttcggtat ccaggtgatg    540
gtcgtgtctg cccccgctta cgctgttgag attgcgcctc cccactggcg tggacgtgcc    600
gtcggtttct acaactgcgg ctggttcggt ggttccatcc ccgctgcggc cgtcacctac    660
ggctgcaaca catcgacaa cgacttctcg tggcgtattc ctttcattct gcagtgcttt     720
gcctgtgtca ttgtcgtctg ttccatctgg ttcattcccg aatcgccccg ttggcagata    780
gcccacggcc aggaggagaa ggccatcgct tcctgacca agtaccacgg taatggcaac     840
cgtaatgccc gcctagtcct cctggagatc gaggaaatga gagagggtat tcgtttggat    900
ggtatcgaca agagatggtg ggattaccgc ccattcttct tcacccacag cggccgctgg    960
cgtttcctcc aggtcatgat gatctccgtc ttcggtcagt ggtctggtaa cggtctgggt   1020
tacttcaacg ccactatcta caacaccctg ggctacacct ccagctccat gcagctgctc   1080
atgaacttga tcaactccat cgtttcggcc attggggctc tgaccgccgt cgcccttacc   1140
gatcgcatgc cccgtcggaa ggttttggtc tggggtactt ttgcttgtgc catcaccatg   1200
gccgtcaacg ccggtgtctc cgagccctg atcaagcaga ccgccaccgg taacatcaac    1260
aaaacctacg ccaaaccgc cgtcgccttc tactacctct tcaacttcgt cttctccttc    1320
acctataccc ccctgcaggg cgtcattcct gccgaggccc tcgaaaccac cacccgtgcc   1380
aagggtctcg ccctctccgg tttcatggtc agctgcatca gtttcgtcag ccagtacgcc   1440
agcccgatcg gtctgcagaa tatctccacc cactacttt ggattttcgt cggctgggac    1500
ttgttcgagt ctctctgctg gtatctgttt ggtgtcgaat cccagggtcg tacgctcgag   1560
gaactcgagt gggtttacca gcagcccaag cccgtcaagg cctcgatcca ggtcgacaag   1620
gttgttgtcc agcccgatgg acacgtcatc gagaaaatca ccgacgaggc ttaa         1674
```

<210> SEQ ID NO 50
<211> LENGTH: 557
<212> TYPE: PRT
<213> ORGANISM: Neosartorya fischeri

<400> SEQUENCE: 50

```
Met Ser Ser Thr Asp Glu Lys His Gly Ile Ser Val Glu His Gly Ser
1               5                   10                  15

Pro Gly Ser Asp Thr Asp Thr Lys Pro Ala Val Pro Val Gly His Gly
            20                  25                  30

Glu Ala Ala Lys Val Asp Gly Ala Lys Thr Arg Lys Val Tyr Asn Ala
        35                  40                  45

Glu Leu Tyr Ala Ala Ile Asn Asp Thr Pro Ile Pro Arg Trp Ser Lys
    50                  55                  60

Glu Ser Ile His Leu Tyr Phe Cys Ile Phe Val Ala Phe Cys Cys Ala
65                  70                  75                  80

Cys Ala Asn Gly Tyr Asp Gly Ser Leu Met Gly Ala Ile Leu Ala Met
                85                  90                  95
```

-continued

Lys His Tyr Gln Asn Thr Phe His Thr Gly Leu Ala Gly Pro Lys Val
                100                 105                 110

Ser Leu Val Thr Ser Leu Tyr Thr Val Gly Ser Ile Ala Ala Thr Pro
            115                 120                 125

Phe Ser Ala Val Ile Ser Asp Arg Leu Gly Arg Arg Lys Cys Met Phe
        130                 135                 140

Val Gly Ala Trp Ile Ile Ile Ala Gly Thr Ile Ile Ala Thr Ala
145                 150                 155                 160

Asn His Leu Pro Gln Phe Tyr Val Gly Arg Val Leu Gly Phe Gly
                165                 170                 175

Ile Gln Val Met Val Val Ser Ala Pro Ala Tyr Ala Val Glu Ile Ala
            180                 185                 190

Pro Pro His Trp Arg Gly Arg Ala Val Gly Phe Tyr Asn Cys Gly Trp
        195                 200                 205

Phe Gly Gly Ser Ile Pro Ala Ala Ala Val Thr Tyr Gly Cys Asn Asn
        210                 215                 220

Ile Asp Asn Asp Phe Ser Trp Arg Ile Pro Phe Ile Leu Gln Cys Phe
225                 230                 235                 240

Ala Cys Val Ile Val Cys Ser Ile Trp Phe Ile Pro Glu Ser Pro
            245                 250                 255

Arg Trp Gln Ile Ala His Gly Gln Glu Glu Lys Ala Ile Ala Phe Leu
        260                 265                 270

Thr Lys Tyr His Gly Asn Gly Asn Arg Asn Ala Arg Leu Val Leu Leu
        275                 280                 285

Glu Ile Glu Glu Met Arg Glu Gly Ile Arg Leu Asp Gly Ile Asp Lys
290                 295                 300

Arg Trp Trp Asp Tyr Arg Pro Phe Phe Phe Thr His Ser Gly Arg Trp
305                 310                 315                 320

Arg Phe Leu Gln Val Met Met Ile Ser Val Phe Gly Gln Trp Ser Gly
            325                 330                 335

Asn Gly Leu Gly Tyr Phe Asn Ala Thr Ile Tyr Asn Thr Leu Gly Tyr
        340                 345                 350

Thr Ser Ser Ser Met Gln Leu Leu Met Asn Leu Ile Asn Ser Ile Val
        355                 360                 365

Ser Ala Ile Gly Ala Leu Thr Ala Val Ala Leu Thr Asp Arg Met Pro
370                 375                 380

Arg Arg Lys Val Leu Val Trp Gly Thr Phe Ala Cys Ala Ile Thr Met
385                 390                 395                 400

Ala Val Asn Ala Gly Val Ser Glu Pro Leu Ile Lys Gln Thr Ala Thr
            405                 410                 415

Gly Asn Ile Asn Lys Thr Tyr Gly Gln Thr Ala Val Ala Phe Tyr Tyr
        420                 425                 430

Leu Phe Asn Phe Val Phe Ser Phe Thr Tyr Thr Pro Leu Gln Gly Val
        435                 440                 445

Ile Pro Ala Glu Ala Leu Glu Thr Thr Arg Ala Lys Gly Leu Ala
        450                 455                 460

Leu Ser Gly Phe Met Val Ser Cys Ile Ser Phe Val Ser Gln Tyr Ala
465                 470                 475                 480

Ser Pro Ile Gly Leu Gln Asn Ile Ser Thr His Tyr Phe Trp Ile Phe
            485                 490                 495

Val Gly Trp Asp Leu Phe Glu Ser Leu Cys Trp Tyr Leu Phe Gly Val
        500                 505                 510

Glu Ser Gln Gly Arg Thr Leu Glu Glu Leu Glu Trp Val Tyr Gln Gln 515                 520                 525
Pro Lys Pro Val Lys Ala Ser Ile Gln Val Asp Lys Val Val Val Gln
        530                 535                 540

Pro Asp Gly His Val Ile Glu Lys Ile Thr Asp Glu Ala
545                 550                 555

<210> SEQ ID NO 51
<211> LENGTH: 1740
<212> TYPE: DNA
<213> ORGANISM: Neurospora crassa

<400> SEQUENCE: 51

| | |
|---|---|
| atgtcgtctc acggctccca tgacggggcc agcaccgaga agcatcttgc tactcatgac | 60 |
| attgcgccca cccacgacgc catcaagata gtgcccaagg ccatggcca gacagccaca | 120 |
| aagcccggtg cccaagagaa ggaggtccgc aacgccgccc tatttgcggc catcaaggag | 180 |
| tccaatatca agccctggag caaggagtcc atccacctct atttcgccat cttcgtcgcc | 240 |
| ttttgttgtg catgcgccaa cggttacgat ggttcactca tgaccggaat catcgctatg | 300 |
| gacaagttcc agaaccaatt ccacactggt gacactggtc ctaaagtctc tgtcatcttt | 360 |
| tctctctata ccgttggtgc catggttgga gctcccttcg ctgctatcct ctctgatcgt | 420 |
| tttggccgta gaagggcat gttcatcggt ggtatcttta tcattgtcgg ctccattatt | 480 |
| gttgctagct cctccaagct cgctcagttt gtcgttggcc gcttcgttct tggcctcggt | 540 |
| atcgccatca tgaccgttgc tgccccggcc tactccatcg aaatcgcccc tcctcactgg | 600 |
| cgcggccgct gcactggctt ctacaactgc ggttggttcg gaggttcgat tcctgccgcc | 660 |
| tgcatcacct atggctgcta cttcattaag agcaactggt catggcgtat cccccttgatc | 720 |
| cttcaggctt tcacgtgcct tatcgtcatg tcctccgtct tcttcctccc agaatcccct | 780 |
| cgcttcctat ttgccaacgg ccgcgacgct gaggctgttg cctttcttgt caagtatcac | 840 |
| ggcaacggcg atcccaattc caagctggtg ttgctcgaga ctgaggagat gagggacggt | 900 |
| atcaggaccg acggtgtcga aaggtctgg tgggattacc gcccgctctt catgacccac | 960 |
| agcggccgct ggcgcatggc ccaggtgctc atgatctcca tctttggcca gttctccggc | 1020 |
| aacggtctcg gttacttcaa taccgtcatc ttcaagaaca ttggtgtcac cagcacctcc | 1080 |
| caacagctcg cctacaacat cctcaactcc gtcatctccg ctatcggtgc cttgaccgcc | 1140 |
| gtctccatga ctgatcgtat gccccgccgc gcggtgctca ttatcggtac cttcatgtgc | 1200 |
| gccgctgctc ttgccaccaa ctcgggtctt tcggctactc tcgacaagca gactcaaaga | 1260 |
| ggcacgcaaa tcaacctgaa ccagggtatg aacgagcagg atgccaagga caacgcctac | 1320 |
| ctccacgtcg acagcaacta cgccaagggt gccctggccg cttacttcct cttcaacgtc | 1380 |
| atcttctcct tcacctacac tcccctccag ggtgttattc ccaccgaggc tctcgagacc | 1440 |
| accatccgtg gcaagggtct tgccctttcc ggcttcattg tcaacgccat gggcttcatc | 1500 |
| aaccagttcg ctggccccat cgctctccac aacattggc acaagtacat ctttgtcttt | 1560 |
| gtcggctggg atcttatcga ccgtcgct tggtacttct tggtgtcga atcccaaggc | 1620 |
| cgtaccctcg agcagctcga atgggtctac gaccagccca accccgtcaa ggcctcccta | 1680 |
| aaagtcgaaa aggtcgtcgt ccaggccgac ggccatgtgt ccgaagctat cgttgcttag | 1740 |

<210> SEQ ID NO 52
<211> LENGTH: 579
<212> TYPE: PRT
<213> ORGANISM: Neurospora crassa

<400> SEQUENCE: 52

```
Met Ser Ser His Gly Ser His Asp Gly Ala Ser Thr Glu Lys His Leu
1               5                   10                  15

Ala Thr His Asp Ile Ala Pro Thr His Asp Ala Ile Lys Ile Val Pro
            20                  25                  30

Lys Gly His Gly Gln Thr Ala Thr Lys Pro Gly Ala Gln Glu Lys Glu
        35                  40                  45

Val Arg Asn Ala Ala Leu Phe Ala Ile Lys Glu Ser Asn Ile Lys
    50                  55                  60

Pro Trp Ser Lys Glu Ser Ile His Leu Tyr Phe Ala Ile Phe Val Ala
65                  70                  75                  80

Phe Cys Cys Ala Cys Ala Asn Gly Tyr Asp Gly Ser Leu Met Thr Gly
                85                  90                  95

Ile Ile Ala Met Asp Lys Phe Gln Asn Gln Phe His Thr Gly Asp Thr
            100                 105                 110

Gly Pro Lys Val Ser Val Ile Phe Ser Leu Tyr Thr Val Gly Ala Met
        115                 120                 125

Val Gly Ala Pro Phe Ala Ala Ile Leu Ser Asp Arg Phe Gly Arg Lys
    130                 135                 140

Lys Gly Met Phe Ile Gly Gly Ile Phe Ile Ile Val Gly Ser Ile Ile
145                 150                 155                 160

Val Ala Ser Ser Lys Leu Ala Gln Phe Val Val Gly Arg Phe Val
                165                 170                 175

Leu Gly Leu Gly Ile Ala Ile Met Thr Val Ala Ala Pro Ala Tyr Ser
            180                 185                 190

Ile Glu Ile Ala Pro Pro His Trp Arg Gly Arg Cys Thr Gly Phe Tyr
        195                 200                 205

Asn Cys Gly Trp Phe Gly Gly Ser Ile Pro Ala Ala Cys Ile Thr Tyr
    210                 215                 220

Gly Cys Tyr Phe Ile Lys Ser Asn Trp Ser Trp Arg Ile Pro Leu Ile
225                 230                 235                 240

Leu Gln Ala Phe Thr Cys Leu Ile Val Met Ser Ser Val Phe Phe Leu
            245                 250                 255

Pro Glu Ser Pro Arg Phe Leu Phe Ala Asn Gly Arg Asp Ala Glu Ala
        260                 265                 270

Val Ala Phe Leu Val Lys Tyr His Gly Asn Gly Asp Pro Asn Ser Lys
    275                 280                 285

Leu Val Leu Leu Glu Thr Glu Glu Met Arg Asp Gly Ile Arg Thr Asp
290                 295                 300

Gly Val Asp Lys Val Trp Trp Asp Tyr Arg Pro Leu Phe Met Thr His
305                 310                 315                 320

Ser Gly Arg Trp Arg Met Ala Gln Val Leu Met Ile Ser Ile Phe Gly
            325                 330                 335

Gln Phe Ser Gly Asn Gly Leu Gly Tyr Phe Asn Thr Val Ile Phe Lys
        340                 345                 350

Asn Ile Gly Val Thr Ser Thr Ser Gln Gln Leu Ala Tyr Asn Ile Leu
    355                 360                 365

Asn Ser Val Ile Ser Ala Ile Gly Ala Leu Thr Ala Val Ser Met Thr
370                 375                 380

Asp Arg Met Pro Arg Arg Ala Val Leu Ile Ile Gly Thr Phe Met Cys
385                 390                 395                 400

Ala Ala Ala Leu Ala Thr Asn Ser Gly Leu Ser Ala Thr Leu Asp Lys
```

```
              405                 410                 415
Gln Thr Gln Arg Gly Thr Gln Ile Asn Leu Asn Gln Gly Met Asn Glu
            420                 425                 430

Gln Asp Ala Lys Asp Asn Ala Tyr Leu His Val Asp Ser Asn Tyr Ala
            435                 440                 445

Lys Gly Ala Leu Ala Ala Tyr Phe Leu Phe Asn Val Ile Phe Ser Phe
    450                 455                 460

Thr Tyr Thr Pro Leu Gln Gly Val Ile Pro Thr Glu Ala Leu Glu Thr
465                 470                 475                 480

Thr Ile Arg Gly Lys Gly Leu Ala Leu Ser Gly Phe Ile Val Asn Ala
                485                 490                 495

Met Gly Phe Ile Asn Gln Phe Ala Gly Pro Ile Ala Leu His Asn Ile
            500                 505                 510

Gly Tyr Lys Tyr Ile Phe Val Phe Val Gly Trp Asp Leu Ile Glu Thr
            515                 520                 525

Val Ala Trp Tyr Phe Phe Gly Val Glu Ser Gln Gly Arg Thr Leu Glu
    530                 535                 540

Gln Leu Glu Trp Val Tyr Asp Gln Pro Asn Pro Val Lys Ala Ser Leu
545                 550                 555                 560

Lys Val Glu Lys Val Val Gln Ala Asp Gly His Val Ser Glu Ala
                565                 570                 575

Ile Val Ala

<210> SEQ ID NO 53
<211> LENGTH: 1293
<212> TYPE: DNA
<213> ORGANISM: Aspergillus terreus

<400> SEQUENCE: 53
atgtgtggtg cactattcat ctggatgact gattggtacg gacgaacatg gcgcatcttc      60
tttgatgtc tgggggtctg cattggcaca atcatcacct ccgtggccac atctctcccg     120
atgttcatcg ctggccggtt tctgctgtcc ttcttcgcga cttgcgctca cactgctgct     180
cccctttatc tggttgagat cgccccgcct atttatcgcg ggacgattgc aggaatgtat     240
aacacatttt acaacgttgg ctccgttttc tcaacatcag ctgtgtatac atgtcacaaa     300
tacctatctc acgacagtga cctggattgg cgactccctc tgtggcttca gatagtgtgt     360
ccgggtctgg tttgtctgat catcaaattt tacccagaat cccctcgatg gcttgtttcc     420
aaagaccgcc atggcgaggc tcaggatatc attgccacat atcacgccaa tggcgacgcc     480
gagcatcctc ttgtggcact ccagatgagg gagatgcttg ctactgttga ccgcgagcac     540
cagtcctcct ggaaagacct ctttgacctc cgagtccttg ttgaatccag gtccagtcgt     600
tatcgcctga tgctgaacgt agctttctct tggttcggcc aattcagtgg aaacaacatt     660
gtatcctatt acctgcccat catgctcaat gggatcggta tcactgacac tgacctaaaa     720
ctgatactca acatcgtata tgcagtcatc ggctgggtgg cgtctatatt cggctctcgc     780
cttcacgatg tcgtggggcg tcgcaagatg ctcatgagca ctacggcggg tatgacggtt     840
tgcctggcta tcgtcgccgc gtgcgctgct gggtataccg aatatggcaa ccaaactgca     900
tcgaccgtca gcattgtgtt catcttcatg tttggtgcta tctttgcttg tggcttcacg     960
ccgatgcaac ccatctaccc ggcagaggtt gtgagtaata agatgcgagc caaggccatg    1020
gggacattca aattgacagc tggagcggcc gggttcttga atacatttgt cggccctatt    1080
gcattgtcca acatcggata ctggttctat gtgttcttcg ttttctggga cacttttgag    1140
```

```
ttggctttta tgtatttctt ctttgtggaa acgaaaggat cgaccttgga ggagctggat    1200 gtcttttca aagcgaaaaa cccacgaaag gctagcattg aagctgtcaa agcccgaaag    1260
cggattattc gaggacaaag agattctgtt tga                                 1293
```

<210> SEQ ID NO 54
<211> LENGTH: 526
<212> TYPE: PRT
<213> ORGANISM: Aspergillus terreus

<400> SEQUENCE: 54

```
Met Asn Ser Ser Asp Lys Pro Tyr Ile Met His Asp Glu Lys Glu Ser
1               5                   10                  15

Pro Glu Lys His Gly Glu Ser Thr Thr Ala Ile Glu Ser Asp Leu Thr
            20                  25                  30

Thr Ile Leu Lys Asn Gln Pro Ile Asn Thr Trp Gly Arg Gly Ser Leu
        35                  40                  45

His Leu Tyr Ala Val Cys Leu Val Tyr Leu Cys Ser Thr Met Asn
    50                  55                  60

Gly Tyr Asp Gly Ser Leu Met Gly Ser Ile Asn Ala Val Pro Ser Tyr
65                  70                  75                  80

Thr Ser Tyr Tyr Asn Leu Pro Lys Glu Gly Asn Ser Gly Thr Gly Ile
                85                  90                  95

Val Phe Ala Ile Phe Gln Ile Gly Gln Met Thr Gly Ala Phe Phe Cys
            100                 105                 110

Trp Val Ser Asp Trp His Gly Arg Arg Trp Pro Ile Phe Val Gly Cys
        115                 120                 125

Val Gly Thr Cys Ile Gly Ala Ile Val Thr Ser Val Ala Pro Thr Ile
    130                 135                 140

Pro Ala Phe Ile Gly Gly Arg Phe Leu Leu Ser Phe Phe Ser Thr Ile
145                 150                 155                 160

Ala Thr Thr Ala Ala Pro Leu Tyr Leu Ile Glu Ile Ala Pro Pro Gln
                165                 170                 175

Tyr Arg Gly Thr Val Ala Gly Met Tyr Asn Thr Leu Tyr Tyr Leu Gly
            180                 185                 190

Ser Ile Ile Ala Thr Ser Val Val Tyr Ala Ser Gln Lys Arg Trp Gly
        195                 200                 205

Asn Asp Gly Asn Ile Leu Ala Trp Arg Leu Ser Leu Trp Leu Gln Met
    210                 215                 220

Ile Cys Pro Ala Ile Val Ala Val Phe Ile Trp Leu Cys Pro Glu Ser
225                 230                 235                 240

Pro Arg Tyr Leu Met Ala Lys Asp Gln Pro Glu Lys Ala Arg Lys Val
                245                 250                 255

Leu Gly Thr Ile His Ala Asn Gly Asp Glu Thr His Pro Leu Val Glu
            260                 265                 270

Leu Glu Met Ala Glu Met Arg Arg Ala Ile Leu Glu Thr Gly Leu Met
        275                 280                 285

Ser Trp Lys Thr Tyr Phe Asp Val Arg Asp Leu Phe Lys Thr Gly Ala
    290                 295                 300

Arg Arg Tyr Arg Met Met Leu Asn Met Thr Phe Ala Trp Phe Gly Gln
305                 310                 315                 320

Phe Ser Asp Leu Pro Thr Leu Val Ala Tyr Val Gly Val Thr Asp Pro
                325                 330                 335

Ser Thr Gln Leu Leu Leu Asn Ile Ile Tyr Ala Ile Gly Gly Trp Ile
```

|  |  | 340 |  |  | 345 |  |  | 350 |  |  |  |
|---|---|---|---|---|---|---|---|---|---|---|---|

Pro Ala Ile Ile Gly Ala Arg Leu His Asp Val Val Gly Arg Arg Lys
        355                     360                    365

Met Leu Met Gly Val Thr Val Gly Met Ala Val Cys Leu Ala Ile Ala
   370                     375                     380

Ala Gly Thr Ala Ala Asp Phe Val Asn Thr Gly Ser Lys Thr Ala Ser
385                     390                     395                     400

Val Ala Ser Ile Ser Phe Ile Tyr Ile Phe Gly Ser Val Phe Ala Leu
               405                     410                     415

Ala Phe Thr Ser Met Gln Pro Ile Tyr Pro Gly Glu Val Leu Ser Asn
            420                     425                     430

Asp Met Arg Ala Lys Gly Met Gly Ile Phe Gln Leu Thr Ser Gly Cys
         435                     440                     445

Ala Gly Phe Val Asn Thr Phe Ala Ala Pro Ile Ala Leu Lys Asn Ile
   450                     455                     460

Gly Tyr Trp Phe Tyr Val Phe Val Phe Val Phe Trp Asp Leu Phe Glu Phe
465                     470                     475                     480

Val Phe Ile Tyr Phe Phe Tyr Val Glu Thr Lys Ser Ile Thr Leu Glu
               485                     490                     495

Glu Leu Asp Ala Ile Phe Glu Ala Pro Asn Pro Arg Lys Ala Ser Thr
            500                     505                     510

Arg Ala Val Arg Leu Met His Val Glu Asp Ala Pro Ser Ser
   515                     520                     525

<210> SEQ ID NO 55
<211> LENGTH: 1731
<212> TYPE: DNA
<213> ORGANISM: Aspergillus nidulans

<400> SEQUENCE: 55

```
atggctgacg agaagactgt ccagccttct gcagagcagg aggcagtagg agaagccgag      60
gaagtgaggg tcgcccacga tgcgctcaac gccaaataca gccccttgac ctggtcgatg     120
ttccgtctct acctgtgtct tatcattcca tacctgtgcg ggacccttaa tggatacgac     180
ggctccctca tgggaggact gaacgcgatg gagacgtacc tggacttctt caacatggag     240
acatcgggat ccagcaccgg gatcgtcttt gccctctaca atatcggttc gattccagcc     300
gtcttcttca cggggccggt caacgactac tggggccgac gatgcggcat gtttgttggc     360
gccctgatca tcgttatcgg gacctgcatc caaagtccgt ctgtaaacag agggatgttc     420
ctcgctgggc ggtttatcct tggatttggt gtcagctttt gctgtgtgtc tgcgccgtgc     480
tatgttagtg aaatggcaca tccggcgtgg aggtatgcac cgattttcga aggcctaagc     540
acgaaggaga tactgacggt tgtttctaga ggcacaatta cggggctcta taactgcacc     600
tggtacatcg gctccatcct cgctagctgg gttgtttacg gctgctcaca gctcgacaat     660
gccaactcct tccgcatccc gatcggtgc cagctgatat cgtccgccct tgtcgtgctc     720
ggagtctggt ttatccccga gtcccctcgc tggctgatgg cgcaggaccg tgcagaagac     780
gccgcaaaga ttcttaccag ataccacggg gagaacgacc ccgatcaccc tctcgtgcat     840
ctccagctca agagatgca gcagagcatc gccaccgatg catcagacaa gaaatggtgg     900
gactaccgcg agctctacac cggccactct gcacgtcgca ggctcatctg cgtgctcggc     960
atggcctgtt ttggccagat ctccggcaac agcgtcacca gctactacct cccggtcatg    1020
ctggagaacg ccggtattgt cagcgagagc aggaaactcc tcttcaacgg catctatccc    1080
```

```
ccactctcgc tcatcggggc tgtcgtcggc gcccgcatga cagacaccat cggccgacgc    1140
ccgctactca tctactccct cctcttctgc tctgtcgcct cgccatcat caccggaacc     1200 tcgaagctgg caaccgacga tcccaccaac accgccgctg ccaacaccac aatcgcttc     1260 atctaccttt ttggcatcgt cttctccttt ggctggaccc cgcttcagtc aatgtacatc    1320
gccgagaccc tcacaacaac gacccgcgcc aagggcaccg cagtggggaa tctggcctcg    1380
tccatcgcga gcacgatcat ccagtacagc tctggcccgg ctttcaagga tattcagtac    1440 tactttacc tcgtctttgt gttctgggac ctgattgaga tcgtcattat gtacttctac     1500
tttcctgaga ccaaagaccg cacgctcgag gagctggaag aagtcttttc ggccccgaat    1560
ccggtcaaga ggagtcttgt caagagagat gcggcgacgg tgttgaatac gatgcaggtg    1620
gagcagcggg aattggttta catacctgct actatgggca ctacttattc tcgtcggtca    1680
gagttcttgt ggcagtctct cagtagtgca acgatcttc gacctgcatg a             1731
```

<210> SEQ ID NO 56
<211> LENGTH: 576
<212> TYPE: PRT
<213> ORGANISM: Aspergillus nidulans

<400> SEQUENCE: 56

```
Met Ala Asp Glu Lys Thr Val Gln Pro Ser Ala Glu Gln Glu Ala Val
1               5                   10                  15

Gly Glu Ala Glu Glu Val Arg Val Ala His Asp Ala Leu Asn Ala Lys
                20                  25                  30

Tyr Ser Pro Leu Thr Trp Ser Met Phe Arg Leu Tyr Leu Cys Leu Ile
            35                  40                  45

Ile Pro Tyr Leu Cys Gly Thr Leu Asn Gly Tyr Asp Gly Ser Leu Met
        50                  55                  60

Gly Gly Leu Asn Ala Met Glu Thr Tyr Leu Asp Phe Phe Asn Met Glu
65                  70                  75                  80

Thr Ser Gly Ser Ser Thr Gly Ile Val Phe Ala Leu Tyr Asn Ile Gly
                85                  90                  95

Ser Ile Pro Ala Val Phe Phe Thr Gly Pro Val Asn Asp Tyr Trp Gly
            100                 105                 110

Arg Arg Cys Gly Met Phe Val Gly Ala Leu Ile Ile Val Ile Gly Thr
        115                 120                 125

Cys Ile Gln Ser Pro Ser Val Asn Arg Gly Met Phe Leu Ala Gly Arg
    130                 135                 140

Phe Ile Leu Gly Phe Gly Val Ser Phe Cys Cys Val Ser Ala Pro Cys
145                 150                 155                 160

Tyr Val Ser Glu Met Ala His Pro Ala Trp Arg Tyr Ala Pro Ile Phe
                165                 170                 175

Glu Gly Leu Ser Thr Lys Glu Ile Leu Thr Val Val Ser Arg Gly Thr
            180                 185                 190

Ile Thr Gly Leu Tyr Asn Cys Thr Trp Tyr Ile Gly Ser Ile Leu Ala
        195                 200                 205

Ser Trp Val Val Tyr Gly Cys Ser Gln Leu Asp Asn Ala Asn Ser Phe
    210                 215                 220

Arg Ile Pro Ile Trp Cys Gln Leu Ile Ser Ala Leu Val Val Leu
225                 230                 235                 240

Gly Val Trp Phe Ile Pro Glu Ser Pro Arg Trp Leu Met Ala Gln Asp
                245                 250                 255

Arg Ala Glu Asp Ala Ala Lys Ile Leu Thr Arg Tyr His Gly Glu Asn
```

```
                260                 265                 270
Asp Pro Asp His Pro Leu Val His Leu Gln Leu Lys Glu Met Gln Gln
                275                 280                 285

Ser Ile Ala Thr Asp Ala Ser Asp Lys Lys Trp Trp Asp Tyr Arg Glu
                290                 295                 300

Leu Tyr Thr Gly His Ser Ala Arg Arg Arg Leu Ile Cys Val Leu Gly
305                 310                 315                 320

Met Ala Cys Phe Gly Gln Ile Ser Gly Asn Ser Val Thr Ser Tyr Tyr
                325                 330                 335

Leu Pro Val Met Leu Glu Asn Ala Gly Ile Val Ser Glu Ser Arg Lys
                340                 345                 350

Leu Leu Phe Asn Gly Ile Tyr Pro Pro Leu Ser Leu Ile Gly Ala Val
                355                 360                 365

Val Gly Ala Arg Met Thr Asp Thr Ile Gly Arg Arg Pro Leu Leu Ile
                370                 375                 380

Tyr Ser Leu Leu Phe Cys Ser Val Ala Phe Ala Ile Ile Thr Gly Thr
385                 390                 395                 400

Ser Lys Leu Ala Thr Asp Asp Pro Thr Asn Thr Ala Ala Ala Asn Thr
                405                 410                 415

Thr Ile Ala Phe Ile Tyr Leu Phe Gly Ile Val Phe Ser Phe Gly Trp
                420                 425                 430

Thr Pro Leu Gln Ser Met Tyr Ile Ala Glu Thr Leu Thr Thr Thr Thr
                435                 440                 445

Arg Ala Lys Gly Thr Ala Val Gly Asn Leu Ala Ser Ser Ile Ala Ser
                450                 455                 460

Thr Ile Ile Gln Tyr Ser Ser Gly Pro Ala Phe Lys Asp Ile Gln Tyr
465                 470                 475                 480

Tyr Phe Tyr Leu Val Phe Val Phe Trp Asp Leu Ile Glu Ile Val Ile
                485                 490                 495

Met Tyr Phe Tyr Phe Pro Glu Thr Lys Asp Arg Thr Leu Glu Glu Leu
                500                 505                 510

Glu Glu Val Phe Ser Ala Pro Asn Pro Val Lys Arg Ser Leu Val Lys
                515                 520                 525

Arg Asp Ala Ala Thr Val Leu Asn Thr Met Gln Val Glu Gln Arg Glu
                530                 535                 540

Leu Val Tyr Ile Pro Ala Thr Met Gly Thr Thr Tyr Ser Arg Arg Ser
545                 550                 555                 560

Glu Phe Leu Trp Gln Ser Leu Ser Ser Ala Asn Asp Leu Arg Pro Ala
                565                 570                 575

<210> SEQ ID NO 57
<211> LENGTH: 1581
<212> TYPE: DNA
<213> ORGANISM: Phaeosphaeria nodorum

<400> SEQUENCE: 57
atgaacagct ccgataagcc gtacatcatg cacgatgaaa aggagtcacc tgagaagcat      60
ggcgagtcta cgactgcgat agagagtgat ctcacgacca tactcaagaa ccagccgata     120
aacacttggg gtcgtggctc cttgcatctc tatgctgtgt gcttgctggt gtacttgtgt     180
tccacgatga acggctatga cggatcactg atgggctcca tcaacgccgt cccaagctac     240
acttcctact acaatctccc caaggaaggc aacagtggta caggcattgt ctttgcaatt     300
tttcagatcg gtcagatgac tggagccttc ttctgttggg tatcgactg gcatggccgc     360
```

```
cggtggccta tcttcgtcgg atgtgtaggg acctgtattg gcgccattgt aacatctgtc    420
gctcccacga tccctgcgtt catcggcgga cgattcctgc tctctttctt ctcgaccatc    480
gcaacgaccg cagcaccgtt gtacctgatt gagattgcgc cgccgcagta ccgcggcact    540
gttgcaggga tgtacaatac attgtattat ttgggatcaa ttatcgcgac gtctgtcgtc    600
tacgcttcgc aaaagcgctg gggcaacgac ggcaacattc tagcttggag actttcactc    660
tggctgcaga tgatctgccc tgccatcgtg gccgtgttca tatggctttg ccagagtcg     720
ccacgatact taatggcaaa ggaccaaccc gaaaaggcac gcaaagtctt gggtacgatt    780
cacgcaaacg gcgatgaaac gcatccattg gtcgaactcg agatggctga gatgcgccgc    840
gcaattctgg agacaggact catgtcttgg aagacttact ttgatgtccg agacttgttc    900
aagacgggtg cacgccgcta ccggatgatg ttgaacatga cctttgcgtg gttcgggcag    960
ttttctgatc tccccacact cgtggcctac gttggggtca ccgaccccag cacacagcta   1020
ctcctcaaca tcatctacgc aatcggaggc tggatcccag ctataatcgg cgcgcgcctt   1080
cacgatgtcg tcggtcgccg aaagatgctt atgggtgtta cagtcggtat ggcagtttgt   1140
ctagccatcg cagcagggac cgcggccgac ttcgtcaaca ctggcagcaa gacagcttcc   1200
gtcgcttcga tctcattcat ctacatcttc ggttcggtct ttgcgctcgc gttcacttca   1260
atgcaaccca tttaccccgg cgaagtcctg tccaacgaca tgcgtgcgaa gggcatgggt   1320
atcttccaat tgacgtccgg atgtgcaggg ttcgtgaaca cgttcgctgc accaattgcc   1380
cttaagaata tcggctactg gttctatgtg ttcttcgtat tctgggacct gtttgagttc   1440
gtattcatct acttcttcta tgtcgagaca aagtcaatca ccttggaaga gctggatgcc   1500
atcttcgaag cgccgaaccc acggaaggca agcacgagag cggtgcgctt gatgcatgta   1560
gaggatgcgc catcgtcgtg a                                             1581

<210> SEQ ID NO 58
<211> LENGTH: 430
<212> TYPE: PRT
<213> ORGANISM: Phaeosphaeria nodorum

<400> SEQUENCE: 58

Met Cys Gly Ala Leu Phe Ile Trp Met Thr Asp Trp Tyr Gly Arg Thr
1               5                   10                  15

Trp Arg Ile Phe Phe Gly Cys Leu Gly Val Cys Ile Gly Thr Ile Ile
            20                  25                  30

Thr Ser Val Ala Thr Ser Leu Pro Met Phe Ile Ala Gly Arg Phe Leu
        35                  40                  45

Leu Ser Phe Phe Ala Thr Cys Ala His Thr Ala Ala Pro Leu Tyr Leu
    50                  55                  60

Val Glu Ile Ala Pro Pro Ile Tyr Arg Gly Thr Ile Ala Gly Met Tyr
65                  70                  75                  80

Asn Thr Phe Tyr Asn Val Gly Ser Val Phe Ser Thr Ser Ala Val Tyr
                85                  90                  95

Thr Cys His Lys Tyr Leu Ser His Asp Ser Asp Leu Asp Trp Arg Leu
            100                 105                 110

Pro Leu Trp Leu Gln Ile Val Cys Pro Gly Leu Val Cys Leu Ile Ile
        115                 120                 125

Lys Phe Tyr Pro Glu Ser Pro Arg Trp Leu Val Ser Lys Asp Arg His
    130                 135                 140

Gly Glu Ala Gln Asp Ile Ile Ala Thr Tyr His Ala Asn Gly Asp Ala
145                 150                 155                 160
```

| | | | | | | | | | | | |
|---|---|---|---|---|---|---|---|---|---|---|---|
| Glu | His | Pro | Leu | Val | Ala | Leu | Gln | Met | Arg | Glu | Met | Leu | Ala | Thr | Val |
| | | | 165 | | | | | 170 | | | | | 175 | | |

Glu His Pro Leu Val Ala Leu Gln Met Arg Glu Met Leu Ala Thr Val
                    165                    170                    175

Asp Arg Glu His Gln Ser Ser Trp Lys Asp Leu Phe Asp Leu Arg Val
                    180                    185                    190

Leu Val Glu Ser Arg Ser Ser Arg Tyr Arg Leu Met Leu Asn Val Ala
                    195                    200                    205

Phe Ser Trp Phe Gly Gln Phe Ser Gly Asn Asn Ile Val Ser Tyr Tyr
210                    215                    220

Leu Pro Ile Met Leu Asn Gly Ile Gly Ile Thr Asp Thr Asp Leu Lys
225                    230                    235                    240

Leu Ile Leu Asn Ile Val Tyr Ala Val Ile Gly Trp Val Ala Ser Ile
                    245                    250                    255

Phe Gly Ser Arg Leu His Asp Val Val Gly Arg Lys Met Leu Met
                    260                    265                    270

Ser Thr Thr Ala Gly Met Thr Val Cys Leu Ala Ile Val Ala Ala Cys
                    275                    280                    285

Ala Ala Gly Tyr Thr Glu Tyr Gly Asn Gln Thr Ala Ser Thr Val Ser
          290                    295                    300

Ile Val Phe Ile Phe Met Phe Gly Ala Ile Phe Ala Cys Gly Phe Thr
305                    310                    315                    320

Pro Met Gln Pro Ile Tyr Pro Ala Glu Val Val Ser Asn Lys Met Arg
                    325                    330                    335

Ala Lys Ala Met Gly Thr Phe Lys Leu Thr Ala Gly Ala Gly Phe
                    340                    345                    350

Leu Asn Thr Phe Val Gly Pro Ile Ala Leu Ser Asn Ile Gly Tyr Trp
          355                    360                    365

Phe Tyr Val Phe Phe Val Phe Trp Asp Thr Phe Glu Leu Ala Phe Met
370                    375                    380

Tyr Phe Phe Phe Val Glu Thr Lys Gly Ser Thr Leu Glu Glu Leu Asp
385                    390                    395                    400

Val Phe Phe Lys Ala Lys Asn Pro Arg Lys Ala Ser Ile Glu Ala Val
                    405                    410                    415

Lys Ala Arg Lys Arg Ile Ile Arg Gly Gln Arg Asp Ser Val
                    420                    425                    430

<210> SEQ ID NO 59
<211> LENGTH: 1635
<212> TYPE: DNA
<213> ORGANISM: Magnaporthe grisea

<400> SEQUENCE: 59

```
atggacaaga aggaagacat gaccatccac gacgacctgg cgagaagcc cgaggtcgtc      60 ggcaggacca aggagatgaa caccaccctcg ccgccctgg ctgctgccat tgctgccgag     120
ccgccacggc tcctctcggc cggtatgatc aagttgtatg ccatcatgtc ggttggctac     180
ttggtctcga ccatgaacgg tttttgacggt agtttgatgg gtgccatcaa cgacatgacg     240
acctaccaac aaacctttgg cctcagctcc gctggctctt cggccggcat tgtctttatc     300
gtatacaacc tcggccaaat cgccgctttc cccttttgcc cctttctcgc cgacggctac     360
ggacgccgct ggtgcatctt tatcggctgc gtcatcgtcc tcgtcggcac ggccatccag     420
ggcgcgtcgc acacgcagag catgttcatc ggcgggcgct tcgtgctggg cctggggcg     480 tcgatcgcgt cggcggcggc gcccgcgtac acggtggagc tcgcgcaccc ggcgtaccga     540
gggttcatgg cgggcatgta caacaacttt tggtggatcg gcaacatcct ggccgggtgg     600
```

```
actacgtacg gcaccaacct caactttgac aacgcgtggg cctggcgcat ccccaccatc    660
ctgcagtgcg cgctgccggc cgtggtcatg gtcatgatcc tcttcttccc cgagtcgccg    720
cgttggctga tcgcccagga ccgcgccgag gaggccctgg ccatctttgc aaagtaccac    780
ggcgacggca accccgacag cgccatcgtg cagctgcagt accgcgagat tgtcgaggag    840
cgggaggcca tgagggacga caacccctgg tgggatttcc gggagctggt caacacgcgc    900
tctgctcggt accgtctttc catggttgtc atgatggctt tctttggaca gtggtctggc    960
aacaatgtcg tttcctactt tatgcctgcc atggtcaagg aggccggcat caccgacggc   1020
aacacccgcc tgctcctcaa cgccatcaac ccgctctttg gcctcctcgc ctccatcttt   1080
ggcgcctaca tgctggaccg cgtgggccgg cgcttcatga tgctggcggg cctgagcggc   1140
gccctcttct tctacgtgct gctgacggcc ttcacggccg aggtcaagaa caacccgaac   1200
ctgtcgtacg gcgtcatcgt gtccatctac ctctttggca tcttcttcgc ggccggcttc   1260
acgccgctcc agacgctcta ctcgatggag tgcctcacga accgcacgcg cgccaagggc   1320
tccggcatca acttcctgtt cctcaacatc gccatgatcg tcaacacgta cggcatcgcc   1380
gtcggcatgg aggccatcca gtggaagctg tacattgtct acattggctg gatcgccatc   1440
gagatcgcca tcatctactt cttcgccgtc gagaccgccg gcaagaccct cgaggagctc   1500
ggcggcatct ttgaggcccc caacccgcgc aaggccagca cgcaaaagac caggatcgag   1560
gtcgacgagg ctggcaacat cctcagcatg tcgagcgggg acgggagggt gcgcgactcg   1620
gagagggcga tttga                                                    1635
```

```
<210> SEQ ID NO 60
<211> LENGTH: 544
<212> TYPE: PRT
<213> ORGANISM: Magnaporthe grisea

<400> SEQUENCE: 60

Met Asp Lys Lys Glu Asp Met Thr Ile His Asp Asp Leu Gly Glu Lys
1               5                   10                  15

Pro Glu Val Val Gly Arg Thr Lys Glu Met Asn Thr Thr Ser Ala Ala
            20                  25                  30

Leu Ala Ala Ala Ile Ala Ala Glu Pro Pro Arg Leu Leu Ser Ala Gly
        35                  40                  45

Met Ile Lys Leu Tyr Ala Ile Met Ser Val Gly Tyr Leu Val Ser Thr
    50                  55                  60

Met Asn Gly Phe Asp Gly Ser Leu Met Gly Ala Ile Asn Asp Met Thr
65                  70                  75                  80

Thr Tyr Gln Gln Thr Phe Gly Leu Ser Ser Ala Gly Ser Ser Ala Gly
                85                  90                  95

Ile Val Phe Ile Val Tyr Asn Leu Gly Gln Ile Ala Ala Phe Pro Phe
            100                 105                 110

Cys Pro Phe Leu Ala Asp Gly Tyr Gly Arg Arg Trp Cys Ile Phe Ile
        115                 120                 125

Gly Cys Val Ile Val Leu Val Gly Thr Ala Ile Gln Gly Ala Ser His
    130                 135                 140

Thr Gln Ser Met Phe Ile Gly Gly Arg Phe Val Leu Gly Leu Gly Ala
145                 150                 155                 160

Ser Ile Ala Ser Ala Ala Ala Pro Ala Tyr Thr Val Glu Leu Ala His
                165                 170                 175

Pro Ala Tyr Arg Gly Phe Met Ala Gly Met Tyr Asn Asn Phe Trp Trp
```

|       |       |       | 180   |       |       |       | 185   |       |       |       | 190   |       |       |
|-------|-------|-------|-------|-------|-------|-------|-------|-------|-------|-------|-------|-------|-------|
| Ile   | Gly   | Asn   | Ile   | Leu   | Ala   | Gly   | Trp   | Thr   | Thr   | Tyr   | Gly   | Thr   | Asn   | Leu   | Asn   |

Ile Gly Asn Ile Leu Ala Gly Trp Thr Thr Tyr Gly Thr Asn Leu Asn
            195                 200                 205

Phe Asp Asn Ala Trp Ala Trp Arg Ile Pro Thr Ile Leu Gln Cys Ala
        210                 215                 220

Leu Pro Ala Val Val Met Val Met Ile Leu Phe Phe Pro Glu Ser Pro
225                 230                 235                 240

Arg Trp Leu Ile Ala Gln Asp Arg Ala Glu Glu Ala Leu Ala Ile Phe
                245                 250                 255

Ala Lys Tyr His Gly Asp Gly Asn Pro Asp Ser Ala Ile Val Gln Leu
            260                 265                 270

Gln Tyr Arg Glu Ile Val Glu Glu Arg Glu Ala Met Arg Asp Asp Asn
        275                 280                 285

Pro Trp Trp Asp Phe Arg Glu Leu Val Asn Thr Arg Ser Ala Arg Tyr
    290                 295                 300

Arg Leu Ser Met Val Val Met Met Ala Phe Phe Gly Gln Trp Ser Gly
305                 310                 315                 320

Asn Asn Val Val Ser Tyr Phe Met Pro Ala Met Val Lys Glu Ala Gly
                325                 330                 335

Ile Thr Asp Gly Asn Thr Arg Leu Leu Leu Asn Ala Ile Asn Pro Leu
            340                 345                 350

Phe Gly Leu Leu Ala Ser Ile Phe Gly Ala Tyr Met Leu Asp Arg Val
        355                 360                 365

Gly Arg Arg Phe Met Met Leu Ala Gly Leu Ser Gly Ala Leu Phe Phe
    370                 375                 380

Tyr Val Leu Leu Thr Ala Phe Thr Ala Glu Val Lys Asn Asn Pro Asn
385                 390                 395                 400

Leu Ser Tyr Gly Val Ile Val Ser Ile Tyr Leu Phe Gly Ile Phe Phe
                405                 410                 415

Ala Ala Gly Phe Thr Pro Leu Gln Thr Leu Tyr Ser Met Glu Cys Leu
            420                 425                 430

Thr Asn Arg Thr Arg Ala Lys Gly Ser Gly Ile Asn Phe Leu Phe Leu
        435                 440                 445

Asn Ile Ala Met Ile Val Asn Thr Tyr Gly Ile Ala Val Gly Met Glu
    450                 455                 460

Ala Ile Gln Trp Lys Leu Tyr Ile Val Tyr Ile Gly Trp Ile Ala Ile
465                 470                 475                 480

Glu Ile Ala Ile Ile Tyr Phe Phe Ala Val Glu Thr Ala Gly Lys Thr
                485                 490                 495

Leu Glu Glu Leu Gly Gly Ile Phe Glu Ala Pro Asn Pro Arg Lys Ala
            500                 505                 510

Ser Thr Gln Lys Thr Arg Ile Glu Val Asp Glu Ala Gly Asn Ile Leu
        515                 520                 525

Ser Met Ser Ser Gly Asp Gly Arg Val Arg Asp Ser Glu Arg Ala Ile
    530                 535                 540

<210> SEQ ID NO 61
<211> LENGTH: 1608
<212> TYPE: DNA
<213> ORGANISM: Chaetomium globosum

<400> SEQUENCE: 61
atggattcca accgggagaa ggagaccgcg gctggagtcg aacacgccga tcttgcactt      60
gacaaacacg acgtgaccgt tcagcttgcc cacgatgtcg aaaacactgt gtactcgcca     120

-continued

```
tggtcgccgc cgatgctccg cctctatctc gtcttgtcga taagctatct ctgcggctgc    180
ctcaacggct acgacggcag tttgatgggc ggcctgaatg gaatgacgag ttatcaccat    240
tattttgaca tgaccacagc agggtccgct acagggctgg tcttcgccat gtacaacatc    300
ggctcggtgg ccgccgtctt cttcacgggg ccggtcaacg actactttgg ccggcgatgg    360
ggaatgtttg tcggcgcctt gattgtgatc attgggacgt gtgtccaggc gccgagcacc    420
acgaaaggac agttcctggg cggccggttc gtgctcggct cgggggtcag cttctgctgc    480
gtctcggcac cctgctacgt ctcggagatg gctcacccca gtggcgtgg cactctaaca    540
ggactgtaca acaccacttg gtacattggc tcgatcgtcg catcctgggt cgtctacggg    600
tgcgccttca tcgacaacct ggacgcctgg cgtatcccca tctggtgcca gatggtaact    660
tcgggtatcg tctgtctggg agtgctttgg ctgcccgaga gccccggtg gctcgtggcc    720
caagaccggc acgaggaagc cgccaaagtg ctagccacat accacggcga aggccgggcc    780
gaccacccga tggtccagct tcagatgcgc gagatgatga accagatctc caccgaagct    840
tccgacaaga atggtacgta ctaccacgag ctctggaaca cgcactcagc acgccgccgc    900
ctcatctgcg tcatcggcat ggccgtgttc ggccagatca gcggcaacag cctctcctcc    960
tactacatgg tcaccatgct ccaatccgcc ggcatcaccg aacagcacaa agtcctcgcc   1020
ctcaacggga tcaacccggc gctctccttt ctcggcgcca ttctcggcgc gcgcatgacc   1080
gacgtggtcg ggcgccggcc cctgctgctg tacaccatcg tgttcgcgtc ggtgtgcttc   1140
gccatcatca cgggcaccag caagatggcg accgacgacc cgacccaggt ggcggcggcc   1200
aacaccacca tcgccttcat cttcatcttc ggcatcgtgt tttcctttgg ttggaccccg   1260
ctgcagagca tgtacatcgc cgagaccctg cccacggcca cgcgcgcaaa gggcaccgcc   1320
gttggtaatt tttcgtcctc ggtcgcgtct accatcttgc agtacgcgtc gggcccggcg   1380
tttgagaaga ttgggtacta ctttatttg gtctttgtct tttgggatct gctcgagggt   1440
gtctttatgt attattactt ccctgaaacc aaggatagaa acttggaaga gctcgaggag   1500
gtatttgcgg cgccaaaccc ggtcaagaag agtctggaga agagaagcgc gctgactgtt   1560
ctgaataccg tggggggcgca gagggagaag ctgggtgatg aagtttga                1608
```

<210> SEQ ID NO 62
<211> LENGTH: 535
<212> TYPE: PRT
<213> ORGANISM: Chaetomium globosum

<400> SEQUENCE: 62

```
Met Asp Ser Asn Arg Glu Lys Glu Thr Ala Ala Gly Val Glu His Ala
1               5                   10                  15

Asp Leu Ala Leu Asp Lys His Asp Val Thr Val Gln Leu Ala His Asp
            20                  25                  30

Val Glu Asn Thr Val Tyr Ser Pro Trp Ser Pro Met Leu Arg Leu
        35                  40                  45

Tyr Leu Val Leu Ser Ile Ser Tyr Leu Cys Gly Cys Leu Asn Gly Tyr
    50                  55                  60

Asp Gly Ser Leu Met Gly Gly Leu Asn Gly Met Thr Ser Tyr His His
65                  70                  75                  80

Tyr Phe Asp Met Thr Thr Ala Gly Ser Ala Thr Gly Leu Val Phe Ala
                85                  90                  95

Met Tyr Asn Ile Gly Ser Val Ala Ala Val Phe Phe Thr Gly Pro Val
            100                 105                 110
```

-continued

Asn Asp Tyr Phe Gly Arg Arg Trp Gly Met Phe Val Gly Ala Leu Ile
        115                 120                 125

Val Ile Ile Gly Thr Cys Val Gln Ala Pro Ser Thr Thr Lys Gly Gln
130                 135                 140

Phe Leu Gly Gly Arg Phe Val Leu Gly Phe Gly Val Ser Phe Cys Cys
145                 150                 155                 160

Val Ser Ala Pro Cys Tyr Val Ser Glu Met Ala His Pro Lys Trp Arg
                165                 170                 175

Gly Thr Leu Thr Gly Leu Tyr Asn Thr Thr Trp Tyr Ile Gly Ser Ile
                180                 185                 190

Val Ala Ser Trp Val Val Tyr Gly Cys Ala Phe Ile Asp Asn Leu Asp
            195                 200                 205

Ala Trp Arg Ile Pro Ile Trp Cys Gln Met Val Thr Ser Gly Ile Val
        210                 215                 220

Cys Leu Gly Val Leu Trp Leu Pro Glu Ser Pro Arg Trp Leu Val Ala
225                 230                 235                 240

Gln Asp Arg His Glu Glu Ala Ala Lys Val Leu Ala Thr Tyr His Gly
                245                 250                 255

Glu Gly Arg Ala Asp His Pro Met Val Gln Leu Gln Met Arg Glu Met
            260                 265                 270

Met Asn Gln Ile Ser Thr Glu Ala Ser Asp Lys Lys Trp Tyr Asp Tyr
        275                 280                 285

His Glu Leu Trp Asn Thr His Ser Ala Arg Arg Leu Ile Cys Val
        290                 295                 300

Ile Gly Met Ala Val Phe Gly Gln Ile Ser Gly Asn Ser Leu Ser Ser
305                 310                 315                 320

Tyr Tyr Met Val Thr Met Leu Gln Ser Ala Gly Ile Thr Glu Gln His
                325                 330                 335

Lys Val Leu Ala Leu Asn Gly Ile Asn Pro Ala Leu Ser Phe Leu Gly
            340                 345                 350

Ala Ile Leu Gly Ala Arg Met Thr Asp Val Val Gly Arg Arg Pro Leu
        355                 360                 365

Leu Leu Tyr Thr Ile Val Phe Ala Ser Val Cys Phe Ala Ile Ile Thr
        370                 375                 380

Gly Thr Ser Lys Met Ala Thr Asp Asp Pro Thr Gln Val Ala Ala Ala
385                 390                 395                 400

Asn Thr Thr Ile Ala Phe Ile Phe Ile Phe Gly Ile Val Phe Ser Phe
                405                 410                 415

Gly Trp Thr Pro Leu Gln Ser Met Tyr Ile Ala Glu Thr Leu Pro Thr
            420                 425                 430

Ala Thr Arg Ala Lys Gly Thr Ala Val Gly Asn Phe Ser Ser Ser Val
        435                 440                 445

Ala Ser Thr Ile Leu Gln Tyr Ala Ser Gly Pro Ala Phe Glu Lys Ile
450                 455                 460

Gly Tyr Tyr Phe Tyr Leu Val Phe Val Phe Trp Asp Leu Leu Glu Gly
465                 470                 475                 480

Val Phe Met Tyr Tyr Phe Pro Glu Thr Lys Asp Arg Asn Leu Glu
                485                 490                 495

Glu Leu Glu Glu Val Phe Ala Ala Pro Asn Pro Val Lys Lys Ser Leu
                500                 505                 510

Glu Lys Arg Ser Ala Leu Thr Val Leu Asn Thr Val Gly Ala Gln Arg
            515                 520                 525

```
Glu Lys Leu Gly Asp Glu Val
    530                 535
```

<210> SEQ ID NO 63
<211> LENGTH: 1608
<212> TYPE: DNA
<213> ORGANISM: Gibberella zeae

<400> SEQUENCE: 63

```
atggattcca aggccgacga gaaggccggc tttgagcatg gtgctgagta ccaggattct    60
catgtagctg cccaggttgc gcatgatgtc cagaaccaga acctgtcgcc atggacacct   120
tccatgtttc gactgtatct cgttttggcg tgtgcttacc tttgcggttg tctgaatgga   180
tacgatggct ctgttatggg cggcattaat ggcatggatg cctatcagca ctacttcaac   240
atgtcctcgg aaggttcctc gaccggcatc gtatttgcca tgtacaacat cggttctatc   300
gccgccgtct tcttcacggc ccccgtaaac gattggttcg gtcgacggtg gggaatgttc   360
actggcgctg caatcgttat catcggtacc tgcgtccaag ctacatctac caaccgaggc   420
catttcctcg gtggacgctt catcttgggc ttcggtgtca gcttttgctg tgtctccgcg   480
ccttgctacg ttagtgagat ggcccatcct acctggcgag gaaccatcac cggtctttac   540
aactgtacct ggtacatcgg cagcatcatt gctggctggg tcgtcttugg ttgcagttac   600
ctaggcaaag agaatgacat cgcttggcga gttccatct ggtgtcagat ggtcacatca   660
ggctttgtgg taatcttcgt tctcttcttg cctgagtctc ctcgatggct catcgcccaa   720
gaccgtgttg aggatgctgt caaggtcctt gctaagtacc acggtgaagg tgaccccaac   780
catcccatgg tcatcatgca aatcaaggag atgacccacc agatcgcctc tgatgctact   840
gacaagtcgt ggtgggacta ccgcggactc tggaacagtc acagtgcacg acgtcgactt   900
attggtgtct gggtatggc tgtctttgga caggtcagcg gtaacagttt gagctcttac   960
tatctcctg tcatgatgaa gtacgccggc attgtggaag agaagaaggt tctggctctc  1020
aatggtgtca acccagttct tgcttcttc ggtgccattc ttggtgcccg tatgactgac  1080
gttatcggtc gtcgccctct tttgctctac tccatcatat tctgctcttg ctgtttcgcc  1140
atcatcactg gaaccagcaa gctctctctc gacgaccgtg acaactcctc tgctgccaac  1200
gccacagttg ccatgatctt catcttcgga attgtcttct ctttcggctg gactcctctc  1260
cagtccgcat acattgctga gtgtctgtcc accgacacca gagctaaggg aactgccgtt  1320
ggtaacttgg ccagctccat tgcttcaacc attattcagt acagcagcgg ccctgcattc  1380
cagaagatcg ttatcacttt ttacctcgtg tttgttttct gggatctttt tgaagcagtt  1440
atcatttggt tcttcttccc tgagacaaag gaccgtactc tggaggaact gtccgaggtg  1500
tttgaggccc ctaaccccgt caagaagagt ctccagaagc gagatgccaa tacggttatg  1560
aacaccatga acgtggcggg cgatgagaag ctcactggag atgtctaa            1608
```

<210> SEQ ID NO 64
<211> LENGTH: 535
<212> TYPE: PRT
<213> ORGANISM: Gibberella zeae

<400> SEQUENCE: 64

```
Met Asp Ser Lys Ala Asp Glu Lys Ala Gly Phe Glu His Gly Ala Glu
1               5                   10                  15

Tyr Gln Asp Ser His Val Ala Ala Gln Val Ala His Asp Val Gln Asn
            20                  25                  30
```

```
Gln Asn Leu Ser Pro Trp Thr Pro Ser Met Phe Arg Leu Tyr Leu Val
            35                  40                  45

Leu Ala Cys Ala Tyr Leu Cys Gly Cys Leu Asn Gly Tyr Asp Gly Ser
 50                  55                  60

Val Met Gly Gly Ile Asn Gly Met Asp Ala Tyr Gln His Tyr Phe Asn
 65                  70                  75                  80

Met Ser Ser Glu Gly Ser Ser Thr Gly Ile Val Phe Ala Met Tyr Asn
                 85                  90                  95

Ile Gly Ser Ile Ala Ala Val Phe Phe Thr Ala Pro Val Asn Asp Trp
            100                 105                 110

Phe Gly Arg Arg Trp Gly Met Phe Thr Gly Ala Ala Ile Val Ile Ile
            115                 120                 125

Gly Thr Cys Val Gln Ala Thr Ser Thr Asn Arg Gly His Phe Leu Gly
            130                 135                 140

Gly Arg Phe Ile Leu Gly Phe Gly Val Ser Phe Cys Cys Val Ser Ala
145                 150                 155                 160

Pro Cys Tyr Val Ser Glu Met Ala His Pro Thr Trp Arg Gly Thr Ile
                165                 170                 175

Thr Gly Leu Tyr Asn Cys Thr Trp Tyr Ile Gly Ser Ile Ile Ala Gly
            180                 185                 190

Trp Val Val Phe Gly Cys Ser Tyr Leu Gly Lys Glu Asn Asp Ile Ala
            195                 200                 205

Trp Arg Val Pro Ile Trp Cys Gln Met Val Thr Ser Gly Phe Val Val
            210                 215                 220

Ile Phe Val Leu Phe Leu Pro Glu Ser Pro Arg Trp Leu Ile Ala Gln
225                 230                 235                 240

Asp Arg Val Glu Asp Ala Val Lys Val Leu Ala Lys Tyr His Gly Glu
                245                 250                 255

Gly Asp Pro Asn His Pro Met Val Ile Met Gln Ile Lys Glu Met Thr
            260                 265                 270

His Gln Ile Ala Ser Asp Ala Thr Asp Lys Ser Trp Trp Asp Tyr Arg
            275                 280                 285

Gly Leu Trp Asn Ser His Ser Ala Arg Arg Arg Leu Ile Gly Val Leu
            290                 295                 300

Gly Met Ala Val Phe Gly Gln Val Ser Gly Asn Ser Leu Ser Ser Tyr
305                 310                 315                 320

Tyr Leu Pro Val Met Met Lys Tyr Ala Gly Ile Val Glu Glu Lys Lys
                325                 330                 335

Val Leu Ala Leu Asn Gly Val Asn Pro Val Leu Cys Phe Phe Gly Ala
            340                 345                 350

Ile Leu Gly Ala Arg Met Thr Asp Val Ile Gly Arg Arg Pro Leu Leu
            355                 360                 365

Leu Tyr Ser Ile Ile Phe Cys Ser Cys Phe Ala Ile Ile Thr Gly
            370                 375                 380

Thr Ser Lys Leu Ser Leu Asp Asp Arg Asp Asn Ser Ala Ala Asn
385                 390                 395                 400

Ala Thr Val Ala Met Ile Phe Ile Phe Gly Ile Val Phe Ser Phe Gly
                405                 410                 415

Trp Thr Pro Leu Gln Ser Ala Tyr Ile Ala Glu Cys Leu Ser Thr Asp
            420                 425                 430

Thr Arg Ala Lys Gly Thr Ala Val Gly Asn Leu Ala Ser Ser Ile Ala
            435                 440                 445

Ser Thr Ile Ile Gln Tyr Ser Ser Gly Pro Ala Phe Gln Lys Ile Gly
```

```
            450                 455                 460
Tyr His Phe Tyr Leu Val Phe Val Phe Trp Asp Leu Phe Glu Ala Val
465                 470                 475                 480

Ile Ile Trp Phe Phe Phe Pro Glu Thr Lys Asp Arg Thr Leu Glu Glu
                485                 490                 495

Leu Ser Glu Val Phe Glu Ala Pro Asn Pro Val Lys Lys Ser Leu Gln
                500                 505                 510

Lys Arg Asp Ala Asn Thr Val Met Asn Thr Met Asn Val Ala Gly Asp
            515                 520                 525

Glu Lys Leu Thr Gly Asp Val
    530                 535

<210> SEQ ID NO 65
<211> LENGTH: 1608
<212> TYPE: DNA
<213> ORGANISM: Podospora anserina

<400> SEQUENCE: 65
atggcggcga gcacagagaa ggcggcgtct ttcgccgacc atcacgatga caagttccgc      60
gacaccgacg ttgccgtgcg gctcgcccac gatgtcgacg acaccaaata ctccccttgg     120
tcggcaaaga tggcacgtct gtaccttgta cttgcaatag cctacctctg cggatgtctc     180
aatggctacg atgggagcct gatgggcggg ctgaacggga tgaagtcgta tcaacagtac     240
ttcaacatga aacagcagg atcgagtacc ggcctggtct tcgccatgta caacatcggc      300
tccgtcgcag cagtcttctt cactggtccc gtcaacgatt ggtttgggcg ccgctggggc     360
atgttcacag gggctataat catcatcatt ggtacttgtg tccaagcacc gagtacaact     420
cccggtcaat cctcgctgg acgcttcgtt ctcggattcg gggtgagctt ttgctgtgtt      480
tcagcaccgt gctacgtgtc tgaaatggct catccgaagt ggagaggtac tcttacgggc     540
ctctacaact gcacgtggta cattgggagt atcatcgcct catggacagt ctacggttgc     600
tcctacattg gcacgctcga tgcttggcgc attccgattt ggtgccagat ggtgacttct     660
ggtttagtct gtctgggtgt attctggttg ccagaaagtc caagatggct ggtggcccaa     720
gacagacacg aggatgcact ccacgtcttg gccgtttacc atggagaagg gcggaccgat     780
caccccattg tccagttaca aatcaaggag atgatgaacc aaatttcctc cgaggcgtcc     840
gataagaagt ggtacgatta tcatgaattg tggaacactc attccgcacg acggcgtctg     900
atttgcgttc tcgggatggg catctttggc cagatcagcg gcaattcgtt gtcgtcttat     960
tacatggtca caatgctgga gtccgcaggt attgtgcaag agcagcgagt gctggcgctc    1020
aacggtatca accccgtgct gtcgctcttc ggagctgttc ttggcgctcg catgtcagac    1080
gtcattggcc ggcgagcgct gctgctctac acgattgtgt tgcttctgt ttgctttgcc     1140 atcatcacag gcaccagcaa aatggctact gatgatccga cccaagtagc agctgccaac    1200
accaccatcg ccttcatctt catattcgga attgtcttct catttggttg acacccctt     1260 caaagcatgt acatttcaga gtgccttcct acatcgacac gagccaaagg aaccgccgtt    1320
gggaatttct cctcggctgc tgcatcaacg attttgcagt acgcttctgg ccctgccttt    1380
gagaagattg gttattactt ctacttggtt tttgtgttct gggatctttt tgaggcagca    1440
ttcatctact cctgtttcc agagaccaaa gacagaacat tggaggaatt ggaagaggtg    1500
ttttctgccc ctaacccggt caagaagagt ttggagaaga gaagtgccca aactgttctc    1560
aacacggtcg gcgcaaaccc agcatcggaa cttgatcatg aaccttag                 1608
```

<210> SEQ ID NO 66
<211> LENGTH: 535
<212> TYPE: PRT
<213> ORGANISM: Podospora anserina

<400> SEQUENCE: 66

```
Met Ala Ala Ser Thr Glu Lys Ala Ser Phe Ala Asp His His Asp
1               5                   10                  15

Asp Lys Phe Arg Asp Thr Asp Val Ala Val Arg Leu Ala His Asp Val
            20                  25                  30

Asp Asp Thr Lys Tyr Ser Pro Trp Ser Ala Lys Met Ala Arg Leu Tyr
            35                  40                  45

Leu Val Leu Ala Ile Ala Tyr Leu Cys Gly Cys Leu Asn Gly Tyr Asp
    50                  55                  60

Gly Ser Leu Met Gly Gly Leu Asn Gly Met Lys Ser Tyr Gln Gln Tyr
65                  70                  75                  80

Phe Asn Met Lys Thr Ala Gly Ser Ser Thr Gly Leu Val Phe Ala Met
                85                  90                  95

Tyr Asn Ile Gly Ser Val Ala Ala Val Phe Phe Thr Gly Pro Val Asn
            100                 105                 110

Asp Trp Phe Gly Arg Arg Trp Gly Met Phe Thr Gly Ala Ile Ile Ile
            115                 120                 125

Ile Ile Gly Thr Cys Val Gln Ala Pro Ser Thr Thr Pro Gly Gln Phe
130                 135                 140

Leu Ala Gly Arg Phe Val Leu Gly Phe Gly Val Ser Phe Cys Cys Val
145                 150                 155                 160

Ser Ala Pro Cys Tyr Val Ser Glu Met Ala His Pro Lys Trp Arg Gly
                165                 170                 175

Thr Leu Thr Gly Leu Tyr Asn Cys Thr Trp Tyr Ile Gly Ser Ile Ile
            180                 185                 190

Ala Ser Trp Thr Val Tyr Gly Cys Ser Tyr Ile Gly Thr Leu Asp Ala
            195                 200                 205

Trp Arg Ile Pro Ile Trp Cys Gln Met Val Thr Ser Gly Leu Val Cys
        210                 215                 220

Leu Gly Val Phe Trp Leu Pro Glu Ser Pro Arg Trp Leu Val Ala Gln
225                 230                 235                 240

Asp Arg His Glu Asp Ala Leu His Val Leu Ala Val Tyr His Gly Glu
                245                 250                 255

Gly Arg Thr Asp His Pro Ile Val Gln Leu Gln Ile Lys Glu Met Met
            260                 265                 270

Asn Gln Ile Ser Ser Glu Ala Ser Asp Lys Lys Trp Tyr Asp Tyr His
        275                 280                 285

Glu Leu Trp Asn Thr His Ser Ala Arg Arg Leu Ile Cys Val Leu
    290                 295                 300

Gly Met Gly Ile Phe Gly Gln Ile Ser Gly Asn Ser Leu Ser Ser Tyr
305                 310                 315                 320

Tyr Met Val Thr Met Leu Glu Ser Ala Gly Ile Val Gln Glu Gln Arg
                325                 330                 335

Val Leu Ala Leu Asn Gly Ile Asn Pro Val Leu Ser Leu Phe Gly Ala
            340                 345                 350

Val Leu Gly Ala Arg Met Ser Asp Val Ile Gly Arg Arg Ala Leu Leu
        355                 360                 365

Leu Tyr Thr Ile Val Phe Ala Ser Val Cys Phe Ala Ile Ile Thr Gly
370                 375                 380
```

```
Thr Ser Lys Met Ala Thr Asp Asp Pro Thr Gln Val Ala Ala Asn
385                 390                 395                 400

Thr Thr Ile Ala Phe Ile Phe Ile Phe Gly Ile Val Phe Ser Phe Gly
            405                 410                 415

Trp Thr Pro Leu Gln Ser Met Tyr Ile Ser Glu Cys Leu Pro Thr Ser
            420                 425                 430

Thr Arg Ala Lys Gly Thr Ala Val Gly Asn Phe Ser Ala Ala Ala
            435                 440                 445

Ser Thr Ile Leu Gln Tyr Ala Ser Gly Pro Ala Phe Glu Lys Ile Gly
450                 455                 460

Tyr Tyr Phe Tyr Leu Val Phe Val Phe Trp Asp Leu Phe Glu Ala Ala
465                 470                 475                 480

Phe Ile Tyr Phe Leu Phe Pro Glu Thr Lys Asp Arg Thr Leu Glu Glu
            485                 490                 495

Leu Glu Glu Val Phe Ser Ala Pro Asn Pro Val Lys Lys Ser Leu Glu
            500                 505                 510

Lys Arg Ser Ala Gln Thr Val Leu Asn Thr Val Gly Ala Asn Pro Ala
            515                 520                 525

Ser Glu Leu Asp His Glu Pro
            530                 535

<210> SEQ ID NO 67
<211> LENGTH: 1572
<212> TYPE: DNA
<213> ORGANISM: Sclerotinia sclerotiorum

<400> SEQUENCE: 67
atgttggccg acgaaaaaat aggtgcggag gagacacacc aagaacatgt aggtgccatt      60
gcgaaggacg agagtaatat agctcaagtc aaggttgtga ccggcgatga ggcttttgcg     120
caagcgatgt tgaaggagcc accaaaaacg tggtcggctc gatcctttat actatacgcc     180
tgtgccgtgg tagcttttct tctgcagtaca tgcaacggat tcgatggctc tatgttcaac    240
tccctcctcg caatggagca gtttagaaag tactttaacg ttcaaaacga tggtgcttgg     300
acgggcatag ttacatcgat gtattcgatc ggaagcgttg tttctattcc attcattgga    360
ccagcgattg atacttgggg aagaaaagtc ggtatttata ttggagcatc gtcgattgtc    420
ttgggaacga taatccagtc caccacactc cactcgagta atgcgatcgg acaatttatg   480
ggcggcagat ttttgcttgg atttggtgtg ggaatagttg catcggcagg accaacgttt  540
gttggctcaa ttcttgcttc tggagctgca cgaggaagtg caaatctaac tggcaatatg   600
gcttggcaag ttccagtctg gctgcaaatg gcatttccgg actttgcat ctgcttggca    660 tgggctcttc ccgaaagtcc acgctggcaa tatgtacacg ccagcgaga aaaggcgaaa     720 gcaatgctta cacgatatca tggcgaaggg aatccgaata gcgtttgggt cgaaatgcag    780
cttaatgagt atgaagagtt tttggagttg atggcgccg ataaaagatg gtgggattat    840
cgagcgctgt tcaaagacag ggcttcaaga tatcgtttag cttgcaactg cacaatcgct    900
atatttgggc agtgggccgg aaatggtcca ctttcgtact ttatttcagc tgttcttgac    960
acggcaggaa tcacgaactc gataacacaa cttaacctca acctgggtct aaatgtcatg   1020
caatttgcgc ttgctctat cggtgctacg ctcgtggata agttgggcg ccgtccatta    1080 ttattattcg caaacatcgg atgcgccata gtctggatcg gagccaccgt ctcatcgtcc    1140
atcaattcca gcacaggtag caagagcagt ggcggagctg ttgtggccat gatattcctc    1200
```

-continued

```
ttcgatgcca tcttcagcat aggttttaca cctttacaag cattgtatcc agtcgaagtc   1260
ctgagttttg agatgagagc caaaggaatg gcattcagca actttgctgt gtcagcagcg   1320
actcttgtaa atcaatttgc ataccctgtg gctctggaaa agatcaaatg gaagacatat   1380
cttgtttttg tgatttggtg tccaatccaa gctcttgtga tttacttctt tatccctgag   1440
acgaagaacc gtactttgga agaattggat aacatcttcc gagccaagaa cccgaggaaa   1500
gcatctctgg agaaaaagaa gttagctgtt gacgatggtg caaacgtttt gaaagtggaa   1560
gaagtcattt ga                                                       1572
```

<210> SEQ ID NO 68
<211> LENGTH: 523
<212> TYPE: PRT
<213> ORGANISM: Sclerotinia sclerotiorum

<400> SEQUENCE: 68
```
Met Leu Ala Asp Glu Lys Ile Gly Ala Glu Glu Thr His Gln Glu His
1               5                   10                  15

Val Gly Ala Ile Ala Lys Asp Glu Ser Asn Ile Ala Gln Val Lys Val
            20                  25                  30

Val Thr Gly Asp Glu Ala Phe Ala Gln Ala Met Leu Lys Glu Pro Pro
        35                  40                  45

Lys Thr Trp Ser Ala Arg Ser Phe Ile Leu Tyr Ala Cys Ala Val Val
    50                  55                  60

Ala Phe Phe Cys Ser Thr Cys Asn Gly Phe Asp Gly Ser Met Phe Asn
65                  70                  75                  80

Ser Leu Leu Ala Met Glu Gln Phe Arg Lys Tyr Phe Asn Val Gln Asn
                85                  90                  95

Asp Gly Ala Trp Thr Gly Ile Val Thr Ser Met Tyr Ser Ile Gly Ser
            100                 105                 110

Val Val Ser Ile Pro Phe Ile Gly Pro Ala Ile Asp Thr Trp Gly Arg
        115                 120                 125

Lys Val Gly Ile Tyr Ile Gly Ala Ser Ser Ile Val Leu Gly Thr Ile
    130                 135                 140

Ile Gln Ser Thr Thr Leu His Ser Ser Asn Ala Ile Gly Gln Phe Met
145                 150                 155                 160

Gly Gly Arg Phe Leu Leu Gly Phe Gly Val Gly Ile Val Ala Ser Ala
                165                 170                 175

Gly Pro Thr Phe Val Gly Ser Ile Leu Ala Ser Gly Ala Ala Arg Gly
            180                 185                 190

Ser Ala Asn Leu Thr Gly Asn Met Ala Trp Gln Val Pro Val Trp Leu
        195                 200                 205

Gln Met Ala Phe Pro Gly Leu Cys Ile Cys Leu Ala Trp Ala Leu Pro
    210                 215                 220

Glu Ser Pro Arg Trp Gln Tyr Val His Gly Gln Arg Glu Lys Ala Lys
225                 230                 235                 240

Ala Met Leu Thr Arg Tyr His Gly Glu Gly Asn Pro Asn Ser Val Trp
                245                 250                 255

Val Glu Met Gln Leu Asn Glu Tyr Glu Glu Phe Leu Glu Leu Asp Gly
            260                 265                 270

Ala Asp Lys Arg Trp Trp Asp Tyr Arg Ala Leu Phe Lys Asp Arg Ala
        275                 280                 285

Ser Arg Tyr Arg Leu Ala Cys Asn Cys Thr Ile Ala Ile Phe Gly Gln
    290                 295                 300
```

```
Trp Ala Gly Asn Gly Pro Leu Ser Tyr Phe Ile Ser Ala Val Leu Asp
305                 310                 315                 320

Thr Ala Gly Ile Thr Asn Ser Ile Thr Gln Leu Asn Leu Asn Leu Gly
            325                 330                 335

Leu Asn Val Met Gln Phe Ala Leu Ala Leu Phe Gly Ala Thr Leu Val
        340                 345                 350

Asp Lys Val Gly Arg Arg Pro Leu Leu Leu Phe Ala Asn Ile Gly Cys
    355                 360                 365

Ala Ile Val Trp Ile Gly Ala Thr Val Ser Ser Ser Ile Asn Ser Ser
370                 375                 380

Thr Gly Ser Lys Ser Ser Gly Gly Ala Val Val Ala Met Ile Phe Leu
385                 390                 395                 400

Phe Asp Ala Ile Phe Ser Ile Gly Phe Thr Pro Leu Gln Ala Leu Tyr
            405                 410                 415

Pro Val Glu Val Leu Ser Phe Glu Met Arg Ala Lys Gly Met Ala Phe
        420                 425                 430

Ser Asn Phe Ala Val Ser Ala Ala Thr Leu Val Asn Gln Phe Ala Tyr
    435                 440                 445

Pro Val Ala Leu Glu Lys Ile Lys Trp Lys Thr Tyr Leu Val Phe Val
450                 455                 460

Ile Trp Cys Pro Ile Gln Ala Leu Val Ile Tyr Phe Phe Ile Pro Glu
465                 470                 475                 480

Thr Lys Asn Arg Thr Leu Glu Glu Leu Asp Asn Ile Phe Arg Ala Lys
            485                 490                 495

Asn Pro Arg Lys Ala Ser Leu Gly Lys Lys Lys Leu Ala Val Asp Asp
        500                 505                 510

Gly Ala Asn Val Leu Lys Val Glu Glu Val Ile
            515                 520

<210> SEQ ID NO 69
<211> LENGTH: 302
<212> TYPE: PRT
<213> ORGANISM: Thermobifida fusca

<400> SEQUENCE: 69

Met Thr Glu Arg Glu Arg Arg Gln Ile Phe Trp Thr Arg Met Asp Leu
1               5                   10                  15

Arg Val Thr Pro Tyr Leu Phe Ile Ala Pro Phe Phe Ile Leu Phe Ala
            20                  25                  30

Ile Phe Gly Leu Phe Pro Leu Leu Tyr Thr Val Trp Val Ser Leu His
        35                  40                  45

Asp Trp Thr Leu Leu Gly Gly Asn Gln Gly Phe Asn Trp Phe Ala His
    50                  55                  60

Tyr Thr Arg Leu Val Gln Asp Ala Lys Phe Trp Asn Ser Leu Tyr Asn
65                  70                  75                  80

Thr Phe Gly Ile Phe Val Val Ala Val Val Pro Gln Leu Leu Leu Ala
            85                  90                  95

Met Tyr Leu Ala Asp Thr Leu Ser Arg Arg Ile Arg Ala Val Asn Phe
        100                 105                 110

Phe Arg Met Gly Leu Leu Leu Pro Tyr Leu Thr Ser Ile Ala Ala Val
    115                 120                 125

Ala Ile Val Phe Ser Gln Leu Phe Gly Thr Gln Phe Gly Leu Ile Asn
130                 135                 140

Tyr Val Leu Gly Phe Phe Gly Ile Asp Pro Ile Asn Trp Gln Ala Gly
145                 150                 155                 160
```

-continued

```
Arg Phe Ser Ser Trp Val Ala Ile Ala Val Met Ile Asp Trp Arg Trp
            165                 170                 175

Thr Gly Tyr Asn Ala Leu Ile Tyr Leu Ala Ala Met Ser Ala Ile Pro
        180                 185                 190

Arg Glu Ile Tyr Glu Ala Ala Ile Asp Gly Ala Ser Arg Met Arg
        195                 200                 205

Gln Phe Trp Gln Ile Thr Ile Pro Met Leu Arg Pro Thr Ile Ile Phe
    210                 215                 220

Thr Val Ile Val Ser Thr Ile Gly Gln Met Gln Leu Phe Thr Glu Pro
225                 230                 235                 240

Val Ile Phe Gly Asp Val Ala Gly Gly Thr Gln Gly Gln Phe Gln Thr
                245                 250                 255

Thr Met Met Leu Ile Phe Glu Glu Ala Phe Arg Phe Asn Asn Tyr Gly
                260                 265                 270

Tyr Gly Ser Ala Ile Ala Trp Thr Leu Phe Met Ile Ile Val Val Leu
        275                 280                 285

Ser Ala Leu Asn Ala Leu Leu Thr Ser Lys Ile Lys Gly Ala
        290                 295                 300
```

<210> SEQ ID NO 70
<211> LENGTH: 305
<212> TYPE: PRT
<213> ORGANISM: Thermobifida fusca

<400> SEQUENCE: 70

```
Met Met Ala Ala Thr Ser Thr Pro Ser Ser Pro Ser Val Ser Ala Val
1               5                   10                  15

Pro Gln Ser Ala Lys Lys Arg Lys Arg Lys Asn Gly Gly Ser Ile Gly
                20                  25                  30

Met Arg Glu Ala Thr Pro Leu Thr Tyr Ile Gly Leu Ser Leu Thr Ile
            35                  40                  45

Leu Leu Ser Val Phe Pro Leu Trp Trp Met Phe Val Val Ala Ser Arg
    50                  55                  60

Asp Thr Ala Ala Ser Ala Arg Pro Pro Tyr Leu Trp Pro Gly Gly
65                  70                  75                  80

Asn Phe Leu Glu Asn Leu Glu Arg Leu Phe Ala Asn Thr Thr Ala Asn
                85                  90                  95

Phe Thr Leu Gly Leu Leu Asn Ser Thr Ile Ser Ala Thr Ala Val Ala
            100                 105                 110

Leu Ser Val Val Phe Phe Ser Ser Leu Ala Gly Phe Ser Leu Ala Lys
        115                 120                 125

Leu Arg Phe Lys Gly Arg Asn Val Ala Ala Val Gly Val Val Leu Thr
    130                 135                 140

Met Ala Val Pro Val Gln Met Gly Ile Ile Pro Leu Leu Met Leu Met
145                 150                 155                 160

Glu Trp Phe Gly Trp Arg Gly Gln Ile Thr Ala Ile Ile Val Pro Phe
                165                 170                 175

Met Val Ser Gly Phe Gly Val Phe Met Met Arg Gln Tyr Cys Ile Gln
                180                 185                 190

Ala Ile Pro Asp Glu Leu Leu Glu Ala Ala Arg Met Asp Gly Cys Ser
            195                 200                 205

Thr Phe Arg Ile Tyr Trp Asn Val Val Leu Pro Ala Leu Arg Pro Ala
        210                 215                 220

Met Val Val Leu Gly Leu Leu Thr Phe Met Thr Gln Trp Asn Glu Phe
```

```
            225                 230                 235                 240

Thr Trp Ala Leu Ala Val Leu Thr Pro Ala Asn Pro Thr Val Gln Ile
                245                 250                 255

Ala Ile Asn Gln Leu Asn Gln Ser Ala Tyr Ser Arg Asp Phe Ala Leu
                260                 265                 270

Met Phe Thr Gly Ser Val Val Ala Thr Leu Pro Leu Leu Ile Leu Phe
                275                 280                 285

Phe Val Leu Gly Arg Gln Leu Ile Gly Arg Ile Met Glu Gly Ala Ile
                290                 295                 300

Lys
305

<210> SEQ ID NO 71
<211> LENGTH: 338
<212> TYPE: PRT
<213> ORGANISM: Streptomyces avermitilis

<400> SEQUENCE: 71

Met Ala Thr Arg His Asp Thr Ala Ala Pro Val Lys Glu Gly Gly
1               5                   10                  15

Ala Ala Pro Ala Arg Ala Ser Ala Asp Ala Ala Pro Thr Glu Ala Glu
                20                  25                  30

Gln Arg His Arg Ala Arg Leu Ser Arg Arg Trp Gln Arg Asp Ile Arg
            35                  40                  45

Trp Ser Pro Tyr Ala Phe Val Ser Pro Phe Phe Leu Leu Phe Leu Ala
        50                  55                  60

Phe Gly Leu Phe Pro Leu Ile Tyr Thr Gly Trp Ala Ser Leu His Gln
65                  70                  75                  80

Val Glu Leu Thr Ala Pro Thr Asp Met Glu Trp Val Gly Leu Arg Asn
                85                  90                  95

Tyr Thr Arg Ile Phe Asp Asp Asp Phe Phe Trp Asn Ala Ala Lys Asn
                100                 105                 110

Thr Leu Thr Ile Gly Ile Ile Ala Thr Val Pro Gln Leu Leu Met Ala
                115                 120                 125

Met Gly Leu Ala His Ile Leu Asn Tyr Lys Leu Arg Ala Ser Thr Phe
            130                 135                 140

Tyr Arg Val Ala Met Leu Ala Pro Tyr Ala Thr Ser Ile Ala Ala Ala
145                 150                 155                 160

Ser Leu Val Phe Val Leu Leu Phe Gly Arg Asp Tyr Gly Met Ile Asn
                165                 170                 175

Trp Ala Leu His Gln Val Gly Ile Gly Ala Val Asp Trp Gln Asn Asp
                180                 185                 190

Lys Trp Pro Ser Gln Phe Ala Val Ser Ser Ile Ile Trp Arg Trp
                195                 200                 205

Thr Gly Tyr Asn Ala Leu Ile Tyr Leu Ala Ala Met Gln Ala Ile Pro
        210                 215                 220

Gln Asp Leu Tyr Glu Ser Ala Ala Leu Asp Gly Ala Ser Arg Trp Arg
225                 230                 235                 240

Gln Phe Leu His Val Thr Leu Pro Ala Leu Arg Pro Thr Ile Leu Phe
                245                 250                 255

Thr Val Val Ser Thr Ile Gly Ala Ser Gln Val Phe Gly Glu Pro
                260                 265                 270

Leu Leu Phe Asp Ala Asn Lys Gly Ala Ser Gly Gly Ala Glu His Gln
                275                 280                 285
```

```
Phe Gln Thr Leu Gly Leu Tyr Leu Tyr Glu Gln Gly Trp Val Asn Gln
290                 295                 300
His Leu Gly Arg Ala Ser Ala Ile Ala Trp Thr Met Phe Leu Ile Leu
305                 310                 315                 320
Ile Leu Val Gly Ile Val Asn Tyr Val Ile Ser Arg Arg Leu Arg Ala
                325                 330                 335
Ser Ser

<210> SEQ ID NO 72
<211> LENGTH: 306
<212> TYPE: PRT
<213> ORGANISM: Streptomyces reticuli

<400> SEQUENCE: 72

Met Ala Pro Asp Pro Gly Ala Ala Gly Leu Tyr Arg Trp Asp Met Lys
1               5                   10                  15
Ala Ser Pro Tyr Ala Phe Val Ala Pro Phe Leu Leu Phe Gly Ala
                20                  25                  30
Phe Ser Leu Val Pro Leu Leu Tyr Thr Ala Trp Tyr Ser Leu His Asn
                35                  40                  45
Val Gln Leu Ser Ala Leu Asp His Lys Thr Trp Ala Gly Leu Asp Asn
    50                  55                  60
Tyr Glu Asn Leu Leu Ser Ser Asp Phe Phe Trp Asn Ala Leu Lys Asn
65                  70                  75                  80
Thr Leu Thr Ile Gly Ile Ile Ser Thr Val Pro Gln Leu Leu Ala Ala
                85                  90                  95
Leu Ala Leu Ala His Leu Leu Asn Tyr Lys Leu Arg Gly Ser Thr Ala
                100                 105                 110
Trp Arg Val Val Met Leu Thr Pro Tyr Ala Thr Ser Val Ala Ala Ala
                115                 120                 125
Thr Leu Val Phe Thr Leu Leu Tyr Ser Trp Asp Gly Gly Met Val Asn
130                 135                 140
Trp Ile Leu Asp Phe Phe Gly Val Asp Pro Val Asn Trp Arg Glu Ser
145                 150                 155                 160
Asp Trp Gly Ser Gln Phe Ala Val Ser Ser Ile Val Ile Trp Arg Trp
                165                 170                 175
Thr Gly Tyr Asn Ala Leu Ile Tyr Leu Ala Ala Met Gln Ala Ile Pro
                180                 185                 190
Ala Asp Leu Tyr Glu Ser Ala Ala Leu Asp Gly Ala Asn Arg Trp Gln
                195                 200                 205
Gln Phe Arg His Val Thr Val Pro Gln Leu Arg Pro Thr Ile Leu Phe
                210                 215                 220
Thr Val Val Val Ser Thr Ile Gly Ala Thr Gln Leu Phe Gly Glu Pro
225                 230                 235                 240
Leu Leu Phe Gly Gly Val Ser Gly Ser Lys Gly Gly Ser Glu His Gln
                245                 250                 255
Tyr Gln Thr Leu Gly Leu Tyr Met Tyr Asp Gln Gly Trp Ile Ile Gly
                260                 265                 270
Asn Leu Gly Lys Ala Ser Ala Ile Ala Trp Ser Met Phe Leu Ile Leu
                275                 280                 285
Leu Ile Val Ala Ala Val Asn Leu Leu Leu Thr Arg Arg Leu Arg Lys
                290                 295                 300
Ser Gln
305
```

<210> SEQ ID NO 73
<211> LENGTH: 4308
<212> TYPE: DNA
<213> ORGANISM: Streptomyces reticuli

<400> SEQUENCE: 73

```
ggatcccacg cgggcagtta acaggccgat aactgaacgc ggttcgcccc gtccgctccc      60
ttgacacccc gccgggaacc gacgactctt caacacatca cttgtgggag cgctcccaca     120
gtacctgaca cctacacatc ccgcacgttc cccgcccgag ccgcagcgag tacgaacggg     180
cccgattcca tgcagttggc cgggggggtcg gcacgtcagg caacaggagg acgcaatgcg     240
cacgagcatc cgccggtccc agcggctgat ggccctcgcg gccgtggccg cactgaccac     300
cgggctgctg gccggctgcg ccagcgactc ggacgacggc tcgtccgaca actccggcgg     360
cgacggcggt ggcggcaagg gcaagatcac gctgaccatc gggaccttcg gcgtcttcgg     420
ttacaagcag gccggcctct atgacgagta catgaggctc cacaaggaca tcaacatcaa     480
ggagaacgtc accaccagaa cagacgtgta ctggccgaag gtgctcaccc gcctccaggc     540
cggctccggc accgacgaca ttcaggccat cgaggtcatg aacatcaccg aggccgtgca     600
gacgcaggcc ggcaagttcg tcgacctcgg caaggaggtc gacaagtccc agtggctgga     660
ctggaagaac gcccaggcca ccagccagga cggcaagctg atcgggctcg gcaccgacat     720
cggcccgatg gcgatctgct accgcaagga cctgttcgag aaggcgggcc tggagaccga     780
ccgcaccaag ctcgccgagc agtggaaggg cgactggagc aagtacgtcg acctcggcaa     840
gcagtacatg aagaaggcgc ccggcggcac caagttcgtg gactcggcct cctcggtcta     900
caacgcggcc ctcggcggcg gggacgagcg gtactacaag gaggacggca ccgtcatctg     960
ggactcgtcc ccgagcgtca agaaggcctg ggacaccgcc atggaggtgg ccaccagcga    1020
catgtcggcg aagctgaagc agttcgacaa gccgtgggac cagggcttcg ccaacggcac    1080
cttcgccacg gtggcctgcc cggcctggat gctcggccag atccaggaga aggccggtga    1140
ctccggcaag ggcaagtggg acgtggcggc ggcgccgacc gcgtccaact ggggcggctc    1200
cttcctcggc gtgccgacgg cgaggaagca ccagaaggag gccatcgagc tggtgaagtg    1260
gctgaccgcg ccggagcagc aggcgcccaa ggtcttcgcc aagcaggcaa gcttcccgtc    1320
caccccgtcg gcgtacgcga gcctgaagcc ggccgcggac accacggcgt acttctcgaa    1380
cgcgccgatc acgcagatct tctccgactc ggcgaagacc atcccgacgc agtacttcgg    1440
catcaaggac cagccgatca acaccgcgct caccgacgtc ggcatcctcc aggtcgagca    1500
gaagggcaag tcgcccgagc agggctggga cgccgcgaac aacgagatca aggacgtgct    1560
cggccagtga gcagctccaa gcaggctctc gcgcattccg cgtcgagtgc cgaggccgcg    1620
cccggcagca cgccgggcgc ggccccgggg cgctcgcggt cgcggtgcgc cggatggcgc    1680
cggatcctgg cgcagccggg ctgtaccgct gggacatgaa ggcgtcgccg tacgccttcg    1740
tcgccccctt cttcctgctc ttcggggcct tctccctggt cccgctgctc tacacggcct    1800
ggtactcgct gcacaacgtg cagctgtcgg ccctcgacca caagacctgg gcgggtctgg    1860
acaactacga gaacctgctg tcctcggact tcttctggaa cgccctgaag aacaccctca    1920
ccatcggcat catctcgacc gtgccgcagc tgctggccgc gctggcactc gcgcacctgc    1980
tcaactacaa gctgcgcggc tcgaccgcgt ggcgcgtggt gatgctgacc ccgtacgcca    2040
cctcggtggc ggcggccacc ctggtgttca cgctgctgta ctcgtgggac ggcggcatgg    2100
tcaactggat cctcgacttc ttcggcgtcg acccggtcaa ctggcgggag tcggactggg    2160
```

```
gttcgcagtt cgcggtgtcg tcgatcgtga tctggcggtg gaccgggtac aacgcgctga    2220
tctacctggc cgccatgcag gcgatcccgg ccgacctgta cgagtcggcg gcgctcgacg    2280
gcgccaaccg ctggcagcag ttccggcatg tgaccgttcc gcagctgcgg ccgacgatcc    2340
tgttcacggt ggtcgtctcc accatcggcg cgacccagct gttcggtgag ccgctgctgt    2400
tcggcggggt cagcgggtcc aagggcggct cggagcacca gtaccagacg ctcggcctgt    2460
acatgtacga ccaggctgg atcatcggca acctcggcaa ggcgtccgcg atcgcctggt    2520
cgatgttcct gatcctgctg atcgtcgccg cggtcaacct gctgctcacc cgacggctga    2580
ggaagtccca atgaccacca ctgaactgac cccgccccgc aagggcggcg ggcgcccggg    2640
gccggatggg tgcgggcagg caactgcacg cgggcccggt gacctacgtc gtgctgaccg    2700
tgttcgccct ggtctccctg gccccgctgg tgtggacggc gatcgccgcc tcccgcacca    2760
accaccggct ggccgagacc ccgccgccgc tgtggttcgg cggcaacctg ttcaagaacc    2820
tggaagcggc ctgggagcag gccgggctcg gcaccgcgat gctcaactcg gtgatcgtcg    2880
cgggcacgat cacggtgagc acggtgctgt tctccacgct ggccggcttc gccttcgcca    2940
agctgcggtt ccggttctcg ggcctgctgt tgctgctgac catcggcacg atgatgatcc    3000
cgccgcagct cgccgtcgta ccgctgtatc tgtggatgtc ggacctgggc tggtcgaacc    3060
agctgcacac ggtgatcctg cccagcctgg tgaccgcgtt cggtacgttc ttcatgcggc    3120
agtacctggt gcaggcgctg ccgaccgagc tgatcgaggc ggcccgggtg gacggggcga    3180
gcagtctgcg gatcgtctgg cacgtggtct tccggcggc gcgccccgcg atggcggtgc    3240
tgggtctgct gacgttcgtg ttcgcctgga acgacttcct gtggccgatc atcgccctga    3300
accagcagaa cccgaccgtg caggtaggcc ctgaactcgc tcggcaccgg gtactccccg    3360
accaggcggt gatcatggcg ggcgcgctgc tcggcacgct gccgctgctg gtcgccttcc    3420
tgctgttcgg caagcagatc gtgggcggga tcatgcaggg cgcgatcaag ggctgatccg    3480
cccgtccggt ttcccggggg ccgggctccg ccgtcccggc ccgtccccc actcacccgt    3540
cggcttctcc ggaactcacc cgtcgacttt tccgaccctt catgggagcg cttccatgcc    3600
tgactccgtt tcgtccctga cctttcctcc cgccttcctc tggggcgccg cgacctcggc    3660
gtaccagatc gagggtgcgg tgcgggagga cggccgcacc ccctcgatct gggacacctt    3720
cagccatacg ccgggcaaga cggccggcgg cgagaccggg gacatcgccg tcgaccacta    3780
ccaccgctac cgcgacgacg tggcgctgat ggcggagctg ggcctgaccg cgtaccgctt    3840
ctccgtctcc tggtcccggg tgcagcccac gggccggggg ccggtggtcc agcggggcct    3900
ggacttctac cgccgcctgg tcgacgagct gctggcgcgg ggcatcaagc cggcgctcac    3960
cctgtaccac tgggacctgc cgcaggagct ggaggacgcg ggcggctggc cggtgcggga    4020
caccgcgttc cggttcgccg agtacgcgca gctcgtcggc gaggcgctgg gcgaccgggt    4080
ggagcactgg atcacccctca acgagccgtg gtgcagcgcc ttcctgggct acggctccgg    4140
ggtgcacgcg cccggccgca ccgacccggc ggcctccgtg cgcgcggccc accatctcaa    4200
cctggggcac gggctggccg tctcggccct ccgcgcggcc ctgccggccc gcaaccagat    4260
cgcgatcagc ctcaactcgt ccgtcgtgcg gcccctgtcc caggatcc                 4308
```

<210> SEQ ID NO 74
<211> LENGTH: 303
<212> TYPE: PRT
<213> ORGANISM: Streptomyces coelicolor

<400> SEQUENCE: 74

```
Met Thr Thr Thr Met Thr Lys Pro Pro Ala Asp Ala Ala Pro Glu Pro
1               5                   10                  15

Pro Arg Arg Gly Arg Arg Ser Lys Ala Ser Arg Ala Gly Gly Thr
            20                  25                  30

Leu His Ala Gly Pro Val Ala Tyr Ile Ile Leu Ala Leu Phe Thr Ile
            35                  40                  45

Gly Ser Leu Phe Pro Leu Val Trp Thr Ala Ile Ala Ala Ser Arg Asp
    50                  55                  60

Asn Gln Arg Leu Ala Gln Thr Pro Pro Leu Trp Phe Gly Gly Asn
65                  70                  75                  80

Leu Phe Asp Lys Leu Glu Ile Ala Trp Asn Asp Ala Asn Leu Gly Glu
                85                  90                  95

Ala Phe Leu Asn Thr Thr Ile Val Ala Gly Ile Ser Ala Cys Thr Ile
                100                 105                 110

Val Phe Leu Ser Thr Val Ala Gly Phe Ala Phe Ala Lys Leu Arg Phe
            115                 120                 125

Arg Gly Arg Asn Ala Leu Met Leu Ile Val Val Gly Thr Met Met Val
    130                 135                 140

Pro Pro Gln Leu Ser Ile Ile Pro Leu Tyr Met Met Val Ala Lys Leu
145                 150                 155                 160

Asp Trp Ser Asp Gln Leu Gln Ala Val Ile Leu Pro Ser Leu Val Asn
                165                 170                 175

Ala Phe Gly Val Phe Phe Met Arg Gln Tyr Leu Leu Gln Ala Leu Pro
            180                 185                 190

Asp Glu Ile Ile Glu Ala Ala Arg Val Asp Gly Ala Ser Ser Trp Arg
    195                 200                 205

Val Met Trp His Val Val Phe Pro Ala Ala Arg Pro Ala Met Ala Val
            210                 215                 220

Leu Gly Met Leu Met Phe Val Gln Ser Trp Asn Asp Phe Leu Trp Pro
225                 230                 235                 240

Phe Leu Val Leu Thr Gln Asn Gly Ser Pro Thr Val Gln Val Ala Leu
                245                 250                 255

Ala Gly Leu Gly Arg Gly Tyr Thr Pro Asp Gln Ser Leu Ile Met Ala
            260                 265                 270

Gly Ala Leu Leu Gly Thr Leu Pro Leu Leu Val Phe Ala Ile Phe
    275                 280                 285

Gly Lys Gln Ile Val Gly Gly Ile Met Gln Gly Ala Val Lys Gly
    290                 295                 300
```

<210> SEQ ID NO 75
<211> LENGTH: 306
<212> TYPE: PRT
<213> ORGANISM: Streptomyces griseus

<400> SEQUENCE: 75

```
Met Thr Leu Thr Ser Pro Thr His Pro Ala Pro Val Lys Leu Ala Pro
1               5                   10                  15

Ala Pro Gln Gly Gly Ala Pro Arg Arg Pro Ser Arg Phe Arg Met Gly
            20                  25                  30

Ala Gly Gln Gln Leu Lys Gly Gly Pro Phe Ala Tyr Ile Ala Leu Ala
            35                  40                  45

Val Val Gly Phe Gly Ser Leu Leu Pro Leu Tyr Trp Thr Leu Val Ala
    50                  55                  60
```

```
Ala Ser Arg Thr Gln Asp Glu Val Leu Ala Thr Pro Pro Phe Leu
 65                  70                  75                  80

Pro Gly Gly Lys Leu Leu Glu Asn Leu Gln Thr Ala Trp Glu Gln Ala
                 85                  90                  95

Asn Leu Gly Thr Ala Ile Leu Asn Ser Val Ile Val Ser Ser Ser Ile
            100                 105                 110

Thr Leu Ala Thr Leu Phe Phe Cys Thr Leu Ala Gly Tyr Ala Phe Ala
        115                 120                 125

Lys Met Arg Phe Arg Gly Arg Gly Trp Leu Met Thr Ala Val Ile Ala
    130                 135                 140

Thr Leu Thr Ile Pro Pro Gln Leu Ser Val Val Pro Leu Phe Met Met
145                 150                 155                 160

Met Ser Gly Leu Gly Trp Gly Gly Gln Leu Glu Ser Val Ile Phe Pro
                165                 170                 175

Thr Leu Val Ser Ala Phe Gly Val Phe Met Arg Gln Tyr Leu Ile
            180                 185                 190

Glu Ala Leu Pro Tyr Glu Leu Ile Glu Ala Ala Lys Ile Asp Gly Ala
        195                 200                 205

Asn Asn Leu Arg Ile Val Val Ser Val Val Leu Pro Val Ala Arg Pro
210                 215                 220

Ala Met Met Val Leu Gly Met Leu Thr Phe Val Gln Ala Trp Asn Asp
225                 230                 235                 240

Phe Phe Trp Pro Tyr Leu Ala Leu Asn Gln Gln Asn Pro Thr Leu Gln
                245                 250                 255

Val Ala Leu Gly Gln Leu Ser Ala Ser Tyr Thr Pro Asp Gln Ser Ile
            260                 265                 270

Val Met Ala Gly Ala Leu Ile Ser Thr Leu Pro Leu Leu Val Val Phe
        275                 280                 285

Val Val Phe Gly Lys Lys Ile Val Gly Gly Ile Met Ser Gly Ala Val
    290                 295                 300

Lys Gly
305

<210> SEQ ID NO 76
<211> LENGTH: 322
<212> TYPE: PRT
<213> ORGANISM: Saccharopolyspora erythraea

<400> SEQUENCE: 76

Met Ser Pro Leu Pro Ala Arg Glu Pro Ala Gln Arg Arg Gly Gln
 1               5                  10                  15

His Pro Gly Trp Arg Pro Gly Leu Arg Leu Ala Trp Leu Asp Ile Arg
                 20                  25                  30

Leu Thr Pro Phe Leu Phe Ile Ala Pro Phe Phe Val Leu Phe Ala Val
             35                  40                  45

Phe Gly Leu Phe Pro Leu Leu Tyr Thr Ala Trp Met Ser Leu His Asp
         50                  55                  60

Trp Asn Leu Val Asp Gly Asp Gln Gly Phe Val Gly Phe Ala Asn Tyr
 65                  70                  75                  80

Thr Glu Leu Phe Ala Asp Pro Asn Phe Tyr Asn Ala Leu Phe Asn Thr
                 85                  90                  95

Val Ser Ile Phe Val Val Ser Thr Val Pro Gln Leu Leu Ala Ala Leu
            100                 105                 110

Gly Ile Ala Tyr Leu Leu Asp Arg Pro Leu Arg Ala Ala Thr Ala Trp
        115                 120                 125
```

-continued

```
Arg Ala Gly Val Leu Leu Pro Asn Val Val Ser Val Val Ala Val Ala
    130                 135                 140
Leu Val Phe Gly Gln Leu Phe Gly Arg Asp Phe Gly Val Val Asn Trp
145                 150                 155                 160
Val Leu Gly Leu Val Gly Val Glu Pro Val Asp Trp Gly Gln Glu Arg
                165                 170                 175
Trp Ser Ser His Leu Ala Val Ala Ala Met Val Met Trp Arg Trp Thr
                180                 185                 190
Gly Tyr Asn Ser Leu Leu Tyr Leu Ala Ala Met Arg Asn Val Pro Ala
            195                 200                 205
Glu Leu His Glu Ala Ala Ala Leu Asp Gly Ala Ser Arg Trp Arg Thr
    210                 215                 220
Phe Trp Ser Val Thr Val Pro Ala Ile Arg Pro Thr Ile Ile Phe Thr
225                 230                 235                 240
Val Val Val Ser Thr Ile Gly Gly Leu Gln Leu Phe Ala Glu Pro Gln
                245                 250                 255
Leu Phe Asp Ala Ala Gly Thr Ala Gly Val Gly Gly Ser Asp Arg Gln
            260                 265                 270
Phe Gln Thr Leu Ala Met Tyr Leu Tyr Glu Lys Gly Phe Asn Leu Phe
            275                 280                 285
Asp Ala Gly Tyr Ala Ala Ala Ile Ala Trp Val Leu Phe Val Val Cys
    290                 295                 300
Leu Leu Ser Ala Leu Val Asn Phe Val Leu Val Arg Arg Ile Arg Gly
305                 310                 315                 320
Arg Glu
```